(12) United States Patent
Simari et al.

(10) Patent No.: US 9,132,166 B2
(45) Date of Patent: *Sep. 15, 2015

(54) METHOD OF TREATMENT OF RENAL DYSFUNCTIONS WITH CHIMERIC NATRIURETIC PEPTIDES

(71) Applicant: Mayo Foundation for Medical Education and Research, Rochester, MN (US)

(72) Inventors: Robert D. Simari, Rochester, MN (US); Shuchong Pan, Rochester, MN (US); John C. Burnett, Jr., Rochester, MN (US); Horng H. Chen, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 85 days.

This patent is subject to a terminal disclaimer.

(21) Appl. No.: 13/683,291

(22) Filed: Nov. 21, 2012

(65) Prior Publication Data

US 2013/0143820 A1    Jun. 6, 2013

Related U.S. Application Data

(63) Continuation of application No. 12/376,880, filed as application No. PCT/US2007/075465 on Aug. 8, 2007, now Pat. No. 8,324,162.

(60) Provisional application No. 60/934,584, filed on Jun. 13, 2007, provisional application No. 60/836,581, filed on Aug. 8, 2006.

(51) Int. Cl.
| | |
|---|---|
| *A61K 38/22* | (2006.01) |
| *A61K 38/16* | (2006.01) |
| *A61K 38/12* | (2006.01) |
| *C07K 14/58* | (2006.01) |
| *A61K 38/00* | (2006.01) |

(52) U.S. Cl.
CPC ............... *A61K 38/16* (2013.01); *C07K 14/58* (2013.01); *A61K 38/00* (2013.01)

(58) Field of Classification Search
CPC ............. A61K 38/00; A61K 2300/00; A61K 47/48246; C07K 14/47; C07K 2319/00; C07K 14/4702; C07K 14/575; C07K 14/72; C07K 14/58; A01K 2227/105; A01K 2267/03; G01N 2500/00; C12N 9/6486; C12Y 304/23015; Y10S 530/86; Y10S 530/834

See application file for complete search history.

(56) References Cited

U.S. PATENT DOCUMENTS

| | | | |
|---|---|---|---|
| 4,034,074 | A | 7/1977 | Miles |
| 4,098,876 | A | 7/1978 | Piasio et al. |
| 4,233,402 | A | 11/1980 | Maggio et al. |
| 4,496,544 | A | 1/1985 | Needleman |
| 4,996,143 | A | 2/1991 | Heller et al. |
| 5,114,923 | A | 5/1992 | Seilhamer et al. |
| 5,212,286 | A | 5/1993 | Lewicki et al. |
| 5,296,347 | A | 3/1994 | LaMotte, III |
| 5,434,133 | A | 7/1995 | Tanaka et al. |
| 5,565,322 | A | 10/1996 | Heller |
| 5,580,859 | A | 12/1996 | Felgner et al. |
| 5,583,108 | A | 12/1996 | Wei et al. |
| 5,589,466 | A | 12/1996 | Felgner et al. |
| 5,665,704 | A | 9/1997 | Lowe et al. |
| 5,674,710 | A | 10/1997 | Seilhamer |
| 5,846,932 | A | 12/1998 | Lowe et al. |
| 5,849,489 | A | 12/1998 | Heller |
| 5,948,761 | A | 9/1999 | Seilhamer et al. |
| 6,124,430 | A | 9/2000 | Mischak et al. |
| 6,162,603 | A | 12/2000 | Heller |
| 6,376,207 | B1 | 4/2002 | Mischak et al. |
| 6,551,795 | B1 | 4/2003 | Rubenfield et al. |
| 6,586,396 | B1 | 7/2003 | Seilhamer |
| 6,812,339 | B1 | 11/2004 | Venter et al. |
| 6,818,619 | B2 | 11/2004 | Burnett, Jr. et al. |
| 6,828,107 | B2 | 12/2004 | Asada et al. |
| 6,849,714 | B1 | 2/2005 | Bridon et al. |
| 6,887,470 | B1 | 5/2005 | Bridon et al. |
| 6,887,481 | B1 | 5/2005 | Chan et al. |
| 6,897,030 | B2 | 5/2005 | Seilhamer et al. |
| 6,974,861 | B2 | 12/2005 | Seilhamer et al. |
| 7,179,790 | B2 | 2/2007 | Seilhamer |
| 7,214,786 | B2 | 5/2007 | Kovalic et al. |

(Continued)

FOREIGN PATENT DOCUMENTS

| | | |
|---|---|---|
| WO | WO 84/03285 | 8/1984 |
| WO | WO 84/03825 | 10/1984 |

(Continued)

OTHER PUBLICATIONS

Supplementary European Search Report and Annex in European Application No. 07 81 3886, Completed Jan. 26, 2010, 7 pages.
International Search Report and Written Opinion in International Application No. PCT/US2004/017554, mailed Oct. 18, 2007, 12 pages.
International Preliminary Report on Patentability in International Application No. PCT/US2004/017554, mailed Nov. 15, 2007, 6 pages.

(Continued)

*Primary Examiner* — Elly-Gerald Stoica
(74) *Attorney, Agent, or Firm* — Fish & Ricahrdson P.C.

(57) ABSTRACT

This document provides diuretic and natriuretic polypeptides. For example, this document provides polypeptides having diuretic and/or natriuretic activities. In some cases, a polypeptide provided herein can have diuretic and natriuretic activities, while lacking the ability to lower blood pressure. This document also provides methods and materials for inducing diuretic and/or natriuretic activities within a mammal.

6 Claims, 39 Drawing Sheets

(56) References Cited

U.S. PATENT DOCUMENTS

| | | | |
|---|---|---|---|
| 7,332,569 B2 | 2/2008 | Cojocaru | |
| 8,324,162 B2 | 12/2012 | Simari et al. | |
| 8,354,496 B2 | 1/2013 | Pan et al. | |
| 8,357,656 B2 | 1/2013 | Simari et al. | |
| 2004/0123343 A1 | 6/2004 | Rosa et al. | |
| 2007/0281887 A1 | 12/2007 | Pan | |
| 2013/0143816 A1 | 6/2013 | Pan et al. | |

FOREIGN PATENT DOCUMENTS

| | | |
|---|---|---|
| WO | WO 95/24419 | 9/1995 |
| WO | WO 00/71576 | 11/2000 |
| WO | WO 01/44284 | 6/2001 |
| WO | WO 02/24895 | 3/2002 |
| WO | WO 2005/00095 | 1/2005 |
| WO | WO 2005/072055 | 8/2005 |

OTHER PUBLICATIONS

Authorized Officer A. Nickitas-Etienne. International Preliminary Report on Patentability in International Application No. PCT/US2008/076434, issued Mar. 16, 2010, 6 pages.
Authorized Officer H. K. Cho. International Search Report and Written Opinion of the International Searching Authority in International Application No. PCT/US2008/076434, mailed May 19, 2009, 8 pages.
Authorized Officer S. Baharlou. International Preliminary Reprt on Patentability in International Application No. PCT/US2007/075465, mailed Feb. 19, 2009, 8 pages.
Authorized Officer W. H. Shin. International Search Report in International Application No. PCT/US2007/075465,mailed Dec. 18, 2007, 15 pages.
Extended European search report from European Application No. 10187879.1, dated Mar. 9, 2011, 7 pages.
Office action from Chinese Application No. 200480020964.7, dated Aug. 9, 2010, 16 pages.
Office action from European Application No. 04754213.9, dated Jan. 20, 2009, 7 pages.
Office action from European Application No. 04754213.9, dated May 29, 2009, 6 pages.
Office action from Israel Application No. 172674, dated Apr. 5, 2009, 2 pages.
Office action from Israel Application No. 172674, dated Aug. 8, 2010, 2 pages.
Office action from Japanese Application No. 2006-517173, dated Feb. 16, 2010, 6 pages.
Japanese Office Action in Japanese Application No. 2009-523978, dated Jul. 25, 2012, 15 pages.
Non-Final Office Action in U.S. Appl. No. 10/561,014, mailed Sep. 5, 2008, 23 pages.
Final Office Action in U.S. Appl. No. 10/561,014, mailed Jun. 12, 2009, 18 pages.
Non-Final Office Action in U.S. Appl. No. 10/561,014, mailed Dec. 29, 2009, 13 pages.
Final Office Action in U.S. Appl. No. 10/561,014, mailed Jul. 21, 2010, 11 pages.
Non-Final Office Action in U.S. Appl. No. 10/561,014, mailed Oct. 12, 2011, 14 pages.
Non-Final Office Action in U.S. Appl. No. 12/376,880, mailed Feb. 27, 2012, 16 pages.
Non-Final Office Action in U.S. Appl. No. 12/677,838, mailed Apr. 19, 2012, 9 pages.
Abbey and Potter, "Vasopressin-dependent inhibition of the C-type natriuretic peptide receptor, NPR-B/GC-B, requires elevated intracellular calcium concentrations," 277:42423-42430 peptide receptor, *J. Biol. Chem.*, 2002, 277:42423-42430.
Abdelhafiz, "Heart failure in older people: causes, diagnosis and treatment," *Age Ageing*, 2002, 31(1):29-36.
Anand-Srivastava, "Natriuretic peptide receptor-C signaling and regulation," *Peptides*, 2005, 26:1044-1059.

Ausubel et al. (eds.), *Short Protocols in Molecular Biology*, 1992, Chapters 8 and 11, Green Publishing Associates and John Wiley & Sons.
Best et al., "Dendroaspis natriuretic peptide relaxes isolated human arteries and veins," *Cardiovas. Res.*, 2002, 55:375-384.
Bowie et al., "Deciphering the Message in Protein Sequences: Tolerance to Amino Acid Substitutions," *Science*, 1990, 247:1306-1310.
Bryan and Potter, "The atrial natriuretic peptide receptor (NPR-A/GC-A) distinct microcystin-sensitive and magnesium-dependent protein phosphatases," *J. Biol. Chem.*, 2002, 277:16041-16047.
Burger and Burger, BNP in decompensated heart failure: heart failure: Diagnostic, prognostic and therapeutic potential, *Curr. Opin. Investig. Drugs*, 2001, 2(7):929-35.
Burgess et al., "Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue," *J of Cell Biol.*, 1990, 111:2129-2138.
Chaurand et al., "Peptide and Protein Identification by Matrix-Assisted (MALDI) and MALDI-Post-Source Decay Time-of-Flight Mass Spectrometry," *J. Am. Soc. Mass Spectrom.*, 1999, 10(2):91-103.
Chen et al. "A novel designer natriuretic and diuretic peptide based upon an alternatively spliced BNP without vascular vasodilatory actions," *Circulation*, 2006, 114(18):270 (Abstract 1412).
Chen et al., "Equimolar doses of atrial renal actions in overt experimental heart 2005, 288:R1093-R1097 and brain natriuretic peptides and urodilatin have differential failure," *Am. J. Physiol. Regul. Integr. Comp. Physiol.*, 2005, 288:R1093-R1097.
Chen et al., "Renal response to acute neutral endopeptidase inhibition in mild and severe experimental heart failure," *Circulation*, 1999, 100:2443-2448.
Cole et al., "The EBV-Hybridoma Technique and Its Application to Human Lung Cancer," *Monoclonal Antibodies and Cancer Therapy*, 1985, Alan R. Liss, Inc., pp. 77-96.
Costello-Boerrigter et al., "Vasopressin-2-receptor antagonism augments water excretion without changes in renal hemodynamics or sodium and potassium excretion in human heart failure," *Am. J. Physiol. Renal Physiol.*, 2006, 290:F273-F278.
Cote et al., "Generation of human monoclonal antibodies reactive with cellular antigens," *Proc. Natl. Acad. Sci. USA*, 1983, 80:2026-2030.
Cowie and Mendez, "BNP and congestive heart failure," *Prog. Cardiovasc. Dis.*, 2002, 44(4):293-321.
Fan et al., "Down-regulation does not mediate natriuretic peptide-dependent desensitization of natriuretic peptide receptor (NPR)-A or NPR-B: guanylyl cyclase-linked natriuretic peptide receptors do not internalize," *Mol. Pharmacol.*, 2005, 67:174-183.
Genbank Accession No. ADW08083, dated Jan. 30, 2011, 1 page.
Genbank Accession No. AEB63460, dated Jun. 17, 2011, 1 page.
GenBank Accession No. BQ130005 dated Jul. 15, 2003.
GenBank Accession No. BQ130258 dated Jul. 15, 2003.
GenBank Accession No. M25296 dated Apr. 27, 1993.
Gevaert et al., "Protein identification based on matrix assisted laser desorption/ionization-post source decay-mass spectrometry," *Electrophoresis*, 2001, 22(9):1645-51.
Guatelli et al., "Isothermal, in vitro amplification of nucleic acids by a multienzyme reaction modeled after retroviral replication," *Proc. Natl. Acad. Sci. USA*, 1990, 87:1874-1878.
Haber et al., "Application of a radioimmunoassay for angiotensin I to the physiologic measurements of plasma renin activity in normal human subjects," *J. Clin. Endocrinol.*, 1969, 29:1349-1355.
Huse et al., "Generation of a Large Combinatorial Library of the Immunoglobulin Repertoire in Phage Lambda," *Science*, 1989, 246:1275-1281.
Hyrup and Nielsen, "Peptide Nucleic Acids (PNA): Synthesis, Properties and Potential Applications," *Bioorgan. Med. Chem.*, 1996, 4:5-23.
Köhler and Milstein, "Continuous cultures of fused cells secreting antibody of predefined specificity," *Nature*, 1975, 256:495-497.
Kozbor and Roder, "The production of monoclonal antibodies from human lymphocytes," *Immunology Today*, 1983, 4:72-79.

(56) References Cited

OTHER PUBLICATIONS

Lewis, "PCR's Competitors Are Alive and Well and Moving Rapidly Towards Commercialization," *Genetic Engineering News*, 1992, 12(9):1-3.
Margulies et al., "Induction and prevention of radiocontrast-induced nephropathy in dogs with heart failure," *Kidney International*, 1990, 38(6):1101-1108.
Mathur et al., "Nesiritide—A new agent for acute decompensated heart failure," MJAFI, 2005, 61(4):375-376.
McCurley et al., "Furosemide and the progression of left ventricular dysfunction in experimental heart failure," *J. Am. Coll. Cardiol.*, 2004, 44(6):1301-1307.
Ogawa et al., "Molecular cloning of the complementary DNA and gene that encode mouse brain natriuretic peptide and generation of transgenic mice that overexpress the brain natriuretic peptide gene," *J. Clin. Invest.*, 1994, 93(5):1911-1921.
Pan et al., "Biodesign of a renal-protective peptide based on alternative splicing of B-type natriuretic peptide," *Proc. Natl. Acad. Sci. USA*, 2009, 106(27):11282-11287.
Pawson and Nash, "Assembly of Cell Regulatory Systems through Protein Interaction Domains," *Science*, 2003, 300:445-452.
Peacock, "The B-type natriuretic peptide assay: a rapid test for heart failure," *Cleve. Clin. J. Med.*, 2002, 69(3):243-251.
Richards et al., "BNP in hormone-guided treatment of heart failure," *Trends Endocrinol. Metab.*, 2002, (5):151-155.
Rose et al., "C-type natriuretic peptide activates a non-selective cation current in acutely isolated rat cardiac fibroblasts via natriuretic peptide C receptor-mediated signaling," *J. Physiol.*, 2007, 580(Pt. 1):255-274.
Sabbatini et al., "Atrial natriuretic factor stimulates exocrine pancreatic secretion in the rat through NPR-C receptors," *Am. J. Physiol. Gastrointest. Liver Physiol.*, 2003, G929-G937.
Sabbatini et al., "C-type natriuretic peptide stimulates pancreatic exocrine secretion in the rat: Role of vegal afferent and efferent pathways," *Eur. J. Pharmacol.*, 2007, 577:192-202.
Sackner-Bernstein et al., Risk of worsening renal function with nesiritide in patients with acutely decompensated heart failure, *Circulation*, 2005, 111:1487-1491.
Sagnella, "Practical implications of current natriuretic peptide research," *J. Renin. Angiotensin Aldosterone Syst.*, 2000, 1(4):304-315
Summerton and Weller, "Morpholino Antisense Oligomers: Design, Preparation, and Properties," *Antisense Nucleic Acid Drug Dev.*, 1997, 7:187-195.
Suzuki et al., "The role of the natriuretic peptides in the cardiovascular system," *Cardiovascular Res.*, 2001, 51:489-494.
Tremblay et al., "Biochemistry and physiology of the natriuretic peptide receptor guanylyl cyclases," *Mol. Cell. Biochem.*, 2002, 230(1-2):31-47.
Valli et al., "Review of 10 years of the clinical use of brain peptide in cardiology," *J. Lab. Clin. Med.*, 1999, 134(5):437-444
Walther et al., "Natriuretic peptide system in fetal heart and circulation," *J. Hypertens.*, 2002, 20(5):786-791.
Wei et al., "Atrial and pulmonary endothelin mRNA is increased in a canine model of chronic low cardiac output," *Am. J. Physiol.*, 1997, 273:R838-844.
Weiss, "Hot Prospect for New Gene Amplifier," *Science*, 1991, 254:1292-1293.
Office action for Canadian Application No. 2660294 dated May 8, 2014, 3 pages.
Non-final office action in U.S. Appl. No. 13/616,244, mailed May 23, 2014, 7 pages.
Pan et al., "Alternatively spliced forms of human BNP: Discovery, localization, and function," Circulation, vol. 110, No. 17, Suppl. III, p. III-96, Abstract 452, Oct. 26, 2004.
Office action from Japanese Application No. 2009/523978, mailed May 22, 2014, 6 pages.
Office action from Chinese Application No. 200480020964.7 mailed Mar. 2, 2011, 6 pages.
European Search Report for European Application No. 04754213 mailed Sep. 5, 2008, 6 pages.
Office action from European Application No. 10187879.1 dated Nov. 27, 2013, 7 pages.
Office action in Japanese Application No. 2006-517173, mailed Jul 26, 2011, 3 pages.
Office action in Chinese Application No. 200780029445.0, mailed Apr. 19, 2011, 10 pages.
Office action in Chinese Application No. 200780029445.0, mailed Mar. 7, 2012, 8 pages.
Office action in European Application No. 07813886.4 dated Apr. 16, 2010, 1 page.
Office action in European Application No. 07813886.4 dated Oct. 11, 2011, 6 pages.
Office action from European Application No. 07813886.4, dated Sep. 26, 2013, 5 pages.
Office action in Israeli Application No. 196931, dated Mar. 3, 2011, 3 pages.
Office action from Israeli Application No. 196931, dated Apr. 12, 2013, 2 pages.
Office action from Japanese Application No. 2009-523978, mailed Jul. 31, 2013, 6 pages.

Figure 14 agccc caagatggtg caagggtctg gctgctttgg gaggaagatg gaccggatca gctcctccag tggcctgggc tgcaaag gtaagcaccc cctgccaccc cggccgcctt cccccattcc agtg (SEQ ID NO:5)

agccc caagatggtg caagggtctg gctgctttgg gaggaagatg gaccggatca gctcctccag tggcctgggc tgcaaag gtaagcaccc cctgccaccc cggccgcctt cccccattcc agtggcNgac actgttagag tcactttggg gtttgttgtc tctgggaacc acactctttg a (SEQ ID NO:6)

N = t, c, a, or g

SEQUENCE LISTING

```
<160> NUMBER OF SEQ ID NOS: 6

<210> SEQ ID NO 1
<211> LENGTH: 42
<212> TYPE: PRT
<213> ORGANISM: Artificial Sequence
<220> FEATURE:
<223> OTHER INFORMATION: synthetic polypeptide

<400> SEQUENCE: 1

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Gly Lys His Pro Leu
```

```
                    20                  25                  30

Pro Pro Arg Pro Pro Ser Pro Ile Pro Val
        35                  40

<210> SEQ ID NO 2
<211> LENGTH: 18
<212> TYPE: PRT
<213> ORGANISM: Artificial Sequence
<220> FEATURE:
<223> OTHER INFORMATION: synthetic polypeptide

<400> SEQUENCE: 2

Ala Asp Thr Val Arg Val Thr Leu Gly Phe Val Val Ser Gly Asn His
 1               5                  10                  15

Thr Leu

<210> SEQ ID NO 3
<211> LENGTH: 60
<212> TYPE: PRT
<213> ORGANISM: Artificial Sequence
<220> FEATURE:
<223> OTHER INFORMATION: synthetic polypeptide

<400> SEQUENCE: 3

Ser Pro Lys Met Val Gln Gly Ser Gly Cys Phe Gly Arg Lys Met Asp
 1               5                  10                  15

Arg Ile Ser Ser Ser Gly Leu Gly Cys Lys Gly Lys His Pro Leu
                20                  25                  30

Pro Pro Arg Pro Pro Ser Pro Ile Pro Val Ala Asp Thr Val Arg Val
        35                  40                  45

Thr Leu Gly Phe Val Val Ser Gly Asn His Thr Leu
        50                  55                  60

<210> SEQ ID NO 4
<211> LENGTH: 60
<212> TYPE: PRT
<213> ORGANISM: Artificial Sequence
<220> FEATURE:
<223> OTHER INFORMATION: synthetic polypeptide

<400> SEQUENCE: 4

Ser Pro Lys Met Val Gln Gly Ser Gly Cys Phe Gly Arg Lys Met Asp
 1               5                  10                  15

Arg Ile Ser Ser Ser Gly Leu Gly Cys Lys Gly Lys His Pro Leu
                20                  25                  30

Pro Pro Arg Pro Pro Ser Pro Ile Pro Val Cys Asp Thr Val Arg Val
        35                  40                  45

Thr Leu Gly Phe Val Val Ser Gly Asn His Thr Leu
        50                  55                  60

<210> SEQ ID NO 5
<211> LENGTH: 126
<212> TYPE: DNA
<213> ORGANISM: Artificial Sequence
<220> FEATURE:
<223> OTHER INFORMATION: synthetic oligonucleotide

<400> SEQUENCE: 5
agccccaaga tggtgcaagg gtctggctgc tttgggagga agatggaccg gatcagctcc      60
tccagtggcc tgggctgcaa aggtaagcac ccctgccac cccggccgcc ttcccccatt     120
ccagtg                                                                126
```

```
<210> SEQ ID NO 6
<211> LENGTH: 183
<212> TYPE: DNA
<213> ORGANISM: Artificial Sequence
<220> FEATURE:
<223> OTHER INFORMATION: synthetic oligonucleotide
<221> NAME/KEY: misc_feature
<222> LOCATION: 129
<223> OTHER INFORMATION: n = A, C, T, or G

<400> SEQUENCE: 6
agccccaaga tggtgcaagg gtctggctgc tttgggagga agatggaccg gatcagctcc      60
tccagtggcc tgggctgcaa aggtaagcac ccctgccac cccggccgcc ttcccccatt      120
ccagtggcng acactgttag agtcactttg gggtttgttg tctctgggaa ccacactctt     180
tga                                                                   183
```

US 9,132,166 B2

METHOD OF TREATMENT OF RENAL DYSFUNCTIONS WITH CHIMERIC NATRIURETIC PEPTIDES

CROSS-REFERENCE TO RELATED APPLICATIONS

This application is a continuation of U.S. application Ser. No. 12/376,880, filed on Apr. 15, 2010, now U.S. Patent No. 8,324,162, which is a National Stage application under 35U.S.C. §371 of International Application No. PCT/US2007/075465 having an International Filing Date of Aug. 8, 2007, which claims priority from U.S. Provisional Application No. 60/934,584, filed on Jun. 13, 2007, and U.S. Provisional Application Serial No. 60/836,581, filed on Aug. 8, 2006.

BACKGROUND

1. Technical Field

This document relates to methods and materials such as diuretic and natriuretic polypeptides. For example, this document relates to polypeptides having diuretic and natriuretic activities while lacking the ability to lower blood pressure.

2. Background Information

Members of the natriuretic polypeptide family are hormones that regulate body fluid homeostasis. Atrial natriuretic peptide (ANP) is secreted by atrial myocytes in response to increased intravascular volume. Once ANP is in the circulation, its effects are primarily on the kidney, vascular tissue, and adrenal gland, in which its actions lead to the excretion of sodium and water by the kidneys and a decrease in intravascular volume and blood pressure. BNP also is of myocardial cell origin, and like ANP, it circulates in human plasma. BNP is natriuretic, rennin inhibiting, vasodilating, and lusitropic. The main circulating and storage form of BNP is a 32 amino acid polypeptide with a ring structure. Physiological actions of BNP are mediated through a guanylate cyclase-linked receptor, natriuretic peptide receptor A (NPR-A). Clearance of BNP is promoted by a NPR-C receptor that removes it from the circulation. BNP also is degraded through enzymatic cleavage by neutral endopeptidase. C-type natriuretic peptide (CNP) is of endothelial cell origin and functions as a vasodilating and growth-inhibiting polypeptide. *Dendroaspis* natriuretic peptide (DNP) is similar in structure to ANP, BNP, and CNP, and is isolated from the venom of *Dendoaspis angusticeps* or green mamba snake.

SUMMARY

This document relates to diuretic and natriuretic polypeptides. For example, this document provides polypeptides having diuretic and natriuretic activities. Polypeptides having diuretic activity can be used medically to treat hypertension, kidney disease, cirrhosis, congestive heart failure, or any fluid overload state. Polypeptides having natriuretic activity can increase the removal of sodium from the body and can be used medically to treat hypertension, kidney disease, cirrhosis, congestive heart failure, or any sodium overload state.

In some cases, a polypeptide provided herein can have diuretic and natriuretic activities, while lacking the ability to lower blood pressure. In some cases, a polypeptide provided herein can be administered to a mammal having congestive heart failure under conditions that induce a detectable diuretic effect, without inducing a detectable natriuretic effect, and while affecting glomerular filtration rate.

In general, one aspect of this document features a substantially pure polypeptide between 37 and 47 amino acid residues in length, wherein the polypeptide comprises, or consists essentially of, an amino acid sequence (a) set forth in SEQ ID NO:1 or (b) that aligns to the sequence set forth in SEQ ID NO:1 with five or less amino acid additions, deletions, substitutions, or combinations thereof. The length of the polypeptide can be between 38 and 46 amino acid residues. The length of the polypeptide can be between 39 and 45 amino acid residues. The length of the polypeptide can be between 40 and 44 amino acid residues. The length of the polypeptide can be between 41 and 43 amino acid residues. The length of the polypeptide can be 42 amino acid residues. The length of the polypeptide can be 37 amino acid residues. The length of the polypeptide can be 47 amino acid residues. The amino acid sequence can be the sequence set forth in SEQ ID NO:1. The amino acid sequence can align to the sequence set forth in SEQ ID NO:1 with four or less amino acid additions, deletions, substitutions, or combinations thereof. The amino acid sequence can align to the sequence set forth in SEQ ID NO:1 with three or less amino acid additions, deletions, substitutions, or combinations thereof. The amino acid sequence can align to the sequence set forth in SEQ ID NO:1 with two or less amino acid additions, deletions, substitutions, or combinations thereof. The amino acid sequence can align to the sequence set forth in SEQ ID NO:1 with one or less amino acid additions, deletions, substitutions, or combinations thereof. The amino acid sequence can align to the sequence set forth in SEQ ID NO:1 with five or less amino acid additions. The amino acid sequence can align to the sequence set forth in SEQ ID NO:1 with five or less amino acid deletions. The amino acid sequence can align to the sequence set forth in SEQ ID NO:1 with five or less amino acid substitutions. The length of the polypeptide can be 42 amino acid residues, and wherein the amino acid sequence is the sequence set forth in SEQ ID NO:1. The polypeptide can have diuretic and natriuretic activity. The polypeptide can lack the ability to lower blood pressure in a mammal. The mammal can be a human or dog.

In another aspect, this document features a substantially pure polypeptide between 45 and 65 amino acid residues in length, wherein the polypeptide comprises, or consists essentially of, a first amino acid sequence: (a) set forth in SEQ ID NO:1 or (b) that aligns to the sequence set forth in SEQ ID NO:1 with five or less amino acid deletions, substitutions, or combinations thereof, and wherein the polypeptide comprises a second amino acid sequence: (a) set forth in SEQ ID NO:2 or (b) that aligns to the sequence set forth in SEQ ID NO:2 with (i) five or less amino acid additions, substitutions, or combinations thereof provided that the addition or substitution does not result in the presence of a cysteine residue or (ii) fifteen or less amino acid deletions. The length of the polypeptide can be between 58 and 63 amino acid residues. The length of the polypeptide can be 60 amino acid residues. The length of the polypeptide can be 45 amino acid residues. The polypeptide can be 65 amino acid residues. The sequence of the polypeptide can be the sequence set forth in SEQ ID NO:3. The polypeptide can have diuretic and natriuretic activity.

In another aspect, this document features an isolated nucleic acid encoding a polypeptide between 37 and 47 amino acid residues in length, wherein the polypeptide comprises, or consists essentially of, an amino acid sequence (a) set forth in SEQ ID NO:1 or (b) that aligns to the sequence set forth in SEQ ID NO:1 with five or less amino acid additions, deletions, substitutions, or combinations thereof. The length of the polypeptide can be between 38 and 46 amino acid residues. The length of the polypeptide can be between 39 and 45 amino acid residues. The length of the polypeptide can be between 40 and 44 amino acid residues. The length of the polypeptide can be between 41 and 43 amino acid residues. The length of the polypeptide can be 42 amino acid residues. The length of the polypeptide can be 37 amino acid residues. The length of the polypeptide can be 47 amino acid residues. The amino acid sequence can be the sequence set forth in SEQ ID NO:1. The amino acid sequence can align to the sequence set forth in SEQ ID NO:1 with four or less amino acid additions, deletions, substitutions, or combinations thereof. The amino acid sequence can align to the sequence set forth in SEQ ID NO:1 with three or less amino acid additions, deletions, substitutions, or combinations thereof. The amino acid sequence can align to the sequence set forth in SEQ ID NO:1 with two or less amino acid additions, deletions, substitutions, or combinations thereof. The amino acid sequence can align to the sequence set forth in SEQ ID NO:1 with one or less amino acid additions, deletions, substitutions, or combinations thereof. The amino acid sequence can align to the sequence set forth in SEQ ID NO:1 with five or less amino acid additions. The amino acid sequence can align to the sequence set forth in SEQ ID NO:1 with five or less amino acid deletions. The amino acid sequence can align to the sequence set forth in SEQ ID NO:1 with five or less amino acid substitutions. The length of the polypeptide can be 42 amino acid residues, and wherein the amino acid sequence is the sequence set forth in SEQ ID NO:1. The polypeptide can have diuretic and natriuretic activity. The polypeptide can lack the ability to lower blood pressure in a mammal. The mammal can be a human or dog.

In another aspect, this document features an isolated nucleic acid encoding a polypeptide between 45 and 65 amino acid residues in length, wherein the polypeptide comprises, or consists essentially of, a first amino acid sequence: (a) set forth in SEQ ID NO:1 or (b) that aligns to the sequence set forth in SEQ ID NO:1 with five or less amino acid deletions, substitutions, or combinations thereof, and wherein the polypeptide comprises a second amino acid sequence: (a) set forth in SEQ ID NO:2 or (b) that aligns to the sequence set forth in SEQ ID NO:2 with (i) five or less amino acid additions, substitutions, or combinations thereof provided that the addition or substitution does not result in the presence of a cysteine residue or (ii) fifteen or less amino acid deletions. The length of the polypeptide can be between 58 and 63 amino acid residues. The length of the polypeptide can be 60 amino acid residues. The length of the polypeptide can be 45 amino acid residues. The polypeptide can be 65 amino acid residues. The sequence of the polypeptide can be the sequence set forth in SEQ ID NO:3. The polypeptide can have diuretic and natriuretic activity.

In another aspect, this document features a vector comprising a nucleic acid encoding a polypeptide between 37 and 47 amino acid residues in length, wherein the polypeptide comprises, or consists essentially of, an amino acid sequence (a) set forth in SEQ ID NO:1 or (b) that aligns to the sequence set forth in SEQ ID NO:1 with five or less amino acid additions, deletions, substitutions, or combinations thereof. The length of the polypeptide can be between 38 and 46 amino acid residues. The length of the polypeptide can be between 39 and 45 amino acid residues. The length of the polypeptide can be between 40 and 44 amino acid residues. The length of the polypeptide can be between 41 and 43 amino acid residues. The length of the polypeptide can be 42 amino acid residues. The length of the polypeptide can be 37 amino acid residues. The length of the polypeptide can be 47 amino acid residues. The amino acid sequence can be the sequence set forth in SEQ ID NO:1. The amino acid sequence can align to the sequence set forth in SEQ ID NO:1 with four or less amino acid additions, deletions, substitutions, or combinations thereof. The amino acid sequence can align to the sequence set forth in SEQ ID NO:1 with three or less amino acid additions, deletions, substitutions, or combinations thereof. The amino acid sequence can align to the sequence set forth in SEQ ID NO:1 with two or less amino acid additions, deletions, substitutions, or combinations thereof. The amino acid sequence can align to the sequence set forth in SEQ ID NO:1 with one or less amino acid additions, deletions, substitutions, or combinations thereof. The amino acid sequence can align to the sequence set forth in SEQ ID NO:1 with five or less amino acid additions. The amino acid sequence can align to the sequence set forth in SEQ ID NO:1 with five or less amino acid deletions. The amino acid sequence can align to the sequence set forth in SEQ ID NO:1 with five or less amino acid substitutions. The length of the polypeptide can be 42 amino acid residues, and wherein the amino acid sequence is the sequence set forth in SEQ ID NO:1. The polypeptide can have diuretic and natriuretic activity. The polypeptide can lack the ability to lower blood pressure in a mammal. The mammal can be a human or dog.

In another aspect, this document features a vector comprising a nucleic acid encoding a polypeptide between 45 and 65 amino acid residues in length, wherein the polypeptide comprises, or consists essentially of, a first amino acid sequence: (a) set forth in SEQ ID NO:1 or (b) that aligns to the sequence set forth in SEQ ID NO:1 with five or less amino acid deletions, substitutions, or combinations thereof, and wherein the polypeptide comprises a second amino acid sequence: (a) set forth in SEQ ID NO:2 or (b) that aligns to the sequence set forth in SEQ ID NO:2 with (i) five or less amino acid additions, substitutions, or combinations thereof provided that the addition or substitution does not result in the presence of a cysteine residue or (ii) fifteen or less amino acid deletions. The length of the polypeptide can be between 58 and 63 amino acid residues. The length of the polypeptide can be 60 amino acid residues. The length of the polypeptide can be 45 amino acid residues. The polypeptide can be 65 amino acid residues. The sequence of the polypeptide can be the sequence set forth in SEQ ID NO:3. The polypeptide can have diuretic and natriuretic activity.

In another aspect, this document features a host cell comprising a nucleic acid encoding a polypeptide between 37 and 47 amino acid residues in length, wherein the polypeptide comprises, or consists essentially of, an amino acid sequence (a) set forth in SEQ ID NO:1 or (b) that aligns to the sequence set forth in SEQ ID NO:1 with five or less amino acid additions, deletions, substitutions, or combinations thereof. The length of the polypeptide can be between 38 and 46 amino acid residues. The length of the polypeptide can be between 39 and 45 amino acid residues. The length of the polypeptide can be between 40 and 44 amino acid residues. The length of the polypeptide can be between 41 and 43 amino acid residues. The length of the polypeptide can be 42 amino acid residues. The length of the polypeptide can be 37 amino acid residues. The length of the polypeptide can be 47 amino acid residues. The amino acid sequence can be the sequence set forth in SEQ ID NO:1. The amino acid sequence can align to the sequence set forth in SEQ ID NO:1 with four or less amino acid additions, deletions, substitutions, or combinations thereof. The amino acid sequence can align to the sequence set forth in SEQ ID NO:1 with three or less amino acid additions, deletions, substitutions, or combinations thereof. The amino acid sequence can align to the sequence set forth in SEQ ID NO:1 with two or less amino acid additions, deletions, substitutions, or combinations thereof. The amino acid sequence can align to the sequence set forth in SEQ ID NO:1 with one or less amino acid additions, deletions, substitutions, or combinations thereof. The amino acid sequence can align to the sequence set forth in SEQ ID NO:1 with five or less amino acid additions. The amino acid sequence can align to the sequence set forth in SEQ ID NO:1 with five or less amino acid deletions. The amino acid sequence can align to the sequence set forth in SEQ ID NO:1 with five or less amino acid substitutions. The length of the polypeptide can be 42 amino acid residues, and wherein the amino acid sequence is the sequence set forth in SEQ ID NO:1. The polypeptide can have diuretic and natriuretic activity. The polypeptide can lack the ability to lower blood pressure in a mammal. The mammal can be a human or dog. The host cell can be a eukaryotic host cell.

In another aspect, this document features a host cell comprising a nucleic acid encoding a polypeptide between 45 and 65 amino acid residues in length, wherein the polypeptide comprises, or consists essentially of, a first amino acid sequence: (a) set forth in SEQ ID NO:1 or (b) that aligns to the sequence set forth in SEQ ID NO:1 with five or less amino acid deletions, substitutions, or combinations thereof, and wherein the polypeptide comprises a second amino acid sequence: (a) set forth in SEQ ID NO:2 or (b) that aligns to the sequence set forth in SEQ ID NO:2 with (i) five or less amino acid additions, substitutions, or combinations thereof provided that the addition or substitution does not result in the presence of a cysteine residue or (ii) fifteen or less amino acid deletions. The length of the polypeptide can be between 58 and 63 amino acid residues. The length of the polypeptide can be 60 amino acid residues. The length of the polypeptide can be 45 amino acid residues. The polypeptide can be 65 amino acid residues. The sequence of the polypeptide can be the sequence set forth in SEQ ID NO:3. The polypeptide can have diuretic and natriuretic activity. The host cell can be a eukaryotic host cell.

In another aspect, this document features a pharmaceutical composition comprising a pharmaceutically acceptable carrier and a polypeptide between 37 and 47 amino acid residues in length, wherein the polypeptide comprises, or consists essentially of, an amino acid sequence (a) set forth in SEQ ID NO:1 or (b) that aligns to the sequence set forth in SEQ ID NO:1 with five or less amino acid additions, deletions, substitutions, or combinations thereof. The length of the polypeptide can be between 38 and 46 amino acid residues. The length of the polypeptide can be between 39 and 45 amino acid residues. The length of the polypeptide can be between 40 and 44 amino acid residues. The length of the polypeptide can be between 41 and 43 amino acid residues. The length of the polypeptide can be 42 amino acid residues. The length of the polypeptide can be 37 amino acid residues. The length of the polypeptide can be 47 amino acid residues. The amino acid sequence can be the sequence set forth in SEQ ID NO:1. The amino acid sequence can align to the sequence set forth in SEQ ID NO:1 with four or less amino acid additions, deletions, substitutions, or combinations thereof. The amino acid sequence can align to the sequence set forth in SEQ ID NO:1 with three or less amino acid additions, deletions, substitutions, or combinations thereof. The amino acid sequence can align to the sequence set forth in SEQ ID NO:1 with two or less amino acid additions, deletions, substitutions, or combinations thereof. The amino acid sequence can align to the sequence set forth in SEQ ID NO:1 with one or less amino acid additions, deletions, substitutions, or combinations thereof. The amino acid sequence can align to the sequence set forth in SEQ ID NO:1 with five or less amino acid additions. The amino acid sequence can align to the sequence set forth in SEQ ID NO:1 with five or less amino acid deletions. The amino acid sequence can align to the sequence set forth in SEQ ID NO:1 with five or less amino acid substitutions. The length of the polypeptide can be 42 amino acid residues, and wherein the amino acid sequence is the sequence set forth in SEQ ID NO:1. The polypeptide can have diuretic and natriuretic activity. The polypeptide can lack the ability to lower blood pressure in a mammal. The mammal can be a human or dog.

In another aspect, this document features a pharmaceutical composition comprising a pharmaceutically acceptable carrier and a polypeptide between 45 and 65 amino acid residues in length, wherein the polypeptide comprises, or consists essentially of, a first amino acid sequence: (a) set forth in SEQ ID NO:1 or (b) that aligns to the sequence set forth in SEQ ID NO:1 with five or less amino acid deletions, substitutions, or combinations thereof, and wherein the polypeptide comprises a second amino acid sequence: (a) set forth in SEQ ID NO:2 or (b) that aligns to the sequence set forth in SEQ ID NO:2 with (i) five or less amino acid additions, substitutions, or combinations thereof provided that the addition or substitution does not result in the presence of a cysteine residue or (ii) fifteen or less amino acid deletions. The length of the polypeptide can be between 58 and 63 amino acid residues. The length of the polypeptide can be 60 amino acid residues. The length of the polypeptide can be 45 amino acid residues. The polypeptide can be 65 amino acid residues. The sequence of the polypeptide can be the sequence set forth in SEQ ID NO:3. The polypeptide can have diuretic and natriuretic activity.

In another aspect, this document features a method for increasing diuretic and natriuretic activity within a mammal without lowering blood pressure. The method comprises, or consists essentially of, administering a polypeptide to the mammal, wherein the polypeptide is between 37 and 47 amino acid residues in length, wherein the polypeptide comprises, or consists essentially of, an amino acid sequence (a) set forth in SEQ ID NO:1 or (b) that aligns to the sequence set forth in SEQ ID NO:1 with five or less amino acid additions, deletions, substitutions, or combinations thereof. The length of the polypeptide can be between 38 and 46 amino acid residues. The length of the polypeptide can be between 39 and 45 amino acid residues. The length of the polypeptide can be between 40 and 44 amino acid residues. The length of the polypeptide can be between 41 and 43 amino acid residues. The length of the polypeptide can be 42 amino acid residues. The length of the polypeptide can be 37 amino acid residues. The length of the polypeptide can be 47 amino acid residues. The amino acid sequence can be the sequence set forth in SEQ ID NO:1. The amino acid sequence can align to the sequence set forth in SEQ ID NO:1 with four or less amino acid additions, deletions, substitutions, or combinations thereof. The amino acid sequence can align to the sequence set forth in SEQ ID NO:1 with three or less amino acid additions, deletions, substitutions, or combinations thereof. The amino acid sequence can align to the sequence set forth in SEQ ID NO:1 with two or less amino acid additions, deletions, substitutions, or combinations thereof. The amino acid sequence can align to the sequence set forth in SEQ ID NO:1 with one or less amino acid additions, deletions, substitutions, or combinations thereof. The amino acid sequence can align to the sequence set forth in SEQ ID NO:1 with five or less amino acid additions. The amino acid sequence can align to the sequence set forth in SEQ ID NO:1 with five or less amino acid deletions. The amino acid sequence can align to the sequence set forth in SEQ ID NO:1 with five or less amino acid substitutions. The length of the polypeptide can be 42 amino acid residues, and wherein the amino acid sequence is the sequence set forth in SEQ ID NO:1. The polypeptide can have diuretic and natriuretic activity. The polypeptide can lack the ability to lower blood pressure in a mammal. The mammal can be a human or dog.

In another aspect, this document features a method for increasing diuretic and natriuretic activity within a mammal without lowering blood pressure. The method comprises, or consist essentially of, administering a polypeptide to the mammal, wherein the polypeptide is between 45 and 65 amino acid residues in length, wherein the polypeptide comprises, or consists essentially of, a first amino acid sequence: (a) set forth in SEQ ID NO:1 or (b) that aligns to the sequence set forth in SEQ ID NO:1 with five or less amino acid deletions, substitutions, or combinations thereof, and wherein the polypeptide comprises a second amino acid sequence: (a) set forth in SEQ ID NO:2 or (b) that aligns to the sequence set forth in SEQ ID NO:2 with (i) five or less amino acid additions, substitutions, or combinations thereof provided that the addition or substitution does not result in the presence of a cysteine residue or (ii) fifteen or less amino acid deletions. The length of the polypeptide can be between 58 and 63 amino acid residues. The length of the polypeptide can be 60 amino acid residues. The length of the polypeptide can be 45 amino acid residues. The polypeptide can be 65 amino acid residues. The sequence of the polypeptide can be the sequence set forth in SEQ ID NO:3. The polypeptide can have diuretic and natriuretic activity.

In another aspect, this document features a method for treating a mammal having a renal dysfunction. The method comprises, or consists essentially of, administering, to the mammal, a polypeptide under conditions wherein the severity of a symptom of the renal dysfunction is reduced. The mammal can be a human. The renal dysfunction can comprise renal failure. The renal dysfunction can comprise renal failure accompanied with congestive heart failure. The polypeptide can be administered intravenously, orally, or intranasally. The polypeptide can be administered in a slow release formulation. The polypeptide can be between 37 and 47 amino acid residues in length and comprise an amino acid sequence set forth in SEQ ID NO:1. The polypeptide can be between 37 and 47 amino acid residues in length and comprises an amino acid sequence that aligns to the sequence set forth in SEQ ID NO:1 with five or less amino acid additions, deletions, substitutions, or combinations thereof. The polypeptide can be between 45 and 65 amino acid residues in length and comprise (i) a first amino acid sequence set forth in SEQ ID NO:1 and (ii) a second amino acid sequence set forth in SEQ ID NO:2. The polypeptide can be between 45 and 65 amino acid residues in length, comprise a first amino acid sequence that aligns to the sequence set forth in SEQ ID NO:1 with five or less amino acid deletions, substitutions, or combinations thereof, and comprise a second amino acid sequence set forth in SEQ ID NO:2. The polypeptide can be between 45 and 65 amino acid residues in length, comprises a first amino acid sequence set forth in SEQ ID NO:1, and comprise a second amino acid sequence that aligns to the sequence set forth in SEQ ID NO:2 with (i) five or less amino acid additions, substitutions, or combinations thereof provided that the addition or substitution does not result in the presence of a cysteine residue or (ii) fifteen or less amino acid deletions. The polypeptide can be between 45 and 65 amino acid residues in length, comprise a first amino acid sequence that aligns to the sequence set forth in SEQ ID NO:1 with five or less amino acid deletions, substitutions, or combinations thereof, and comprise a second amino acid sequence that aligns to the sequence set forth in SEQ ID NO:2 with (i) five or less amino acid additions, substitutions, or combinations thereof provided that the addition or substitution does not result in the presence of a cysteine residue or with (ii) fifteen or less amino acid deletions. The symptom can comprise an abnormal serum creatinine level, urine flow, renin level, glomerular filtration rate, urinary cGMP excretion rate, urinary ANP excretion rate, urinary BNP excretion rate, cardiac output, systemic vascular resistance, or aldosterone level. The symptom can comprise reduced urine flow, and wherein the urine flow of the mammal increases at least 50% after the administration step. The symptom can comprise reduced renin level, and wherein the renin level of the mammal increases at least 50% after the administration step. The symptom can comprise reduced glomerular filtration rate, and wherein the glomerular filtration rate of the mammal increases at least 50% after the administration step. The symptom can comprise reduced urinary cGMP excretion rate, and wherein the urinary cGMP excretion rate of the mammal increases at least 25% after the administration step. The symptom can comprise reduced urinary ANP excretion rate, and wherein the urinary ANP excretion rate of the mammal increases at least 25% after the administration step. The symptom can comprise reduced urinary BNP excretion rate, and wherein the urinary BNP excretion rate of the mammal increases at least 25% after the administration step. The symptom can comprise increased cardiac output, and wherein the cardiac output of the mammal decreased at least 2% after the administration step. The symptom can comprise reduced systemic vascular resistance, and wherein the systemic vascular resistance of the mammal increases at least 10% after the administration step. The symptom can comprise reduced aldosterone level, and wherein the aldosterone level of the mammal increases at least 10% after the administration step.

In another aspect, this document features a method for treating a mammal having an inflammatory condition. The method comprises, or consists essentially of, administering, to the mammal, a polypeptide under conditions wherein the severity of a symptom of the inflammatory condition is reduced. The mammal can be a human. The polypeptide can be administered intravenously, orally, or intranasally. The polypeptide can be administered in a slow release formulation. The polypeptide can be between 37 and 47 amino acid residues in length and comprise an amino acid sequence set forth in SEQ ID NO:1. The polypeptide can be between 37 and 47 amino acid residues in length and comprise an amino acid sequence that aligns to the sequence set forth in SEQ ID NO:1 with five or less amino acid additions, deletions, substitutions, or combinations thereof. The polypeptide can be between 45 and 65 amino acid residues in length and comprise (i) a first amino acid sequence set forth in SEQ ID NO:1 and (ii) a second amino acid sequence set forth in SEQ ID NO:2. The polypeptide can be between 45 and 65 amino acid residues in length, comprise a first amino acid sequence that aligns to the sequence set forth in SEQ ID NO:1 with five or less amino acid deletions, substitutions, or combinations thereof, and comprise a second amino acid sequence set forth in SEQ ID NO:2. The polypeptide can be between 45 and 65 amino acid residues in length, comprise a first amino acid sequence set forth in SEQ ID NO:1, and comprise a second amino acid sequence that aligns to the sequence set forth in SEQ ID NO:2 with (i) five or less amino acid additions, substitutions, or combinations thereof provided that the addition or substitution does not result in the presence of a cysteine residue or (ii) fifteen or less amino acid deletions. The polypeptide can be between 45 and 65 amino acid residues in length, comprise a first amino acid sequence that aligns to the sequence set forth in SEQ ID NO:1 with five or less amino acid deletions, substitutions, or combinations thereof, and comprise a second amino acid sequence that aligns to the sequence set forth in SEQ ID NO:2 with (i) five or less amino acid additions, substitutions, or combinations thereof provided that the addition or substitution does not result in the presence of a cysteine residue or with (ii) fifteen or less amino acid deletions.

In another aspect, this document features a method for treating a mammal having a heart dysfunction. The method comprises, or consists essentially of, administering, to the mammal, a polypeptide under conditions wherein the severity of a symptom of the heart dysfunction is reduced. The mammal can be a human. The heart dysfunction can comprise heart failure. The heart dysfunction can comprise congestive heart failure accompanied with renal failure. The polypeptide can be administered intravenously, orally, or intranasally. The polypeptide can be administered in a slow release formulation. The polypeptide can be between 37 and 47 amino acid residues in length and comprise an amino acid sequence set forth in SEQ ID NO:1. The polypeptide can be between 37 and 47 amino acid residues in length and comprise an amino acid sequence that aligns to the sequence set forth in SEQ ID NO:1 with five or less amino acid additions, deletions, substitutions, or combinations thereof. The polypeptide can be between 45 and 65 amino acid residues in length and comprise (i) a first amino acid sequence set forth in SEQ ID NO:1 and (ii) a second amino acid sequence set forth in SEQ ID NO:2. The polypeptide can be between 45 and 65 amino acid residues in length, comprise a first amino acid sequence that aligns to the sequence set forth in SEQ ID NO:1 with five or less amino acid deletions, substitutions, or combinations thereof, and comprise a second amino acid sequence set forth in SEQ ID NO:2. The polypeptide can be between 45 and 65 amino acid residues in length, comprise a first amino acid sequence set forth in SEQ ID NO:1, and comprise a second amino acid sequence that aligns to the sequence set forth in SEQ ID NO:2 with (i) five or less amino acid additions, substitutions, or combinations thereof provided that the addition or substitution does not result in the presence of a cysteine residue or (ii) fifteen or less amino acid deletions. The polypeptide can be between 45 and 65 amino acid residues in length, comprise a first amino acid sequence that aligns to the sequence set forth in SEQ ID NO:1 with five or less amino acid deletions, substitutions, or combinations thereof, and comprise a second amino acid sequence that aligns to the sequence set forth in SEQ ID NO:2 with (i) five or less amino acid additions, substitutions, or combinations thereof provided that the addition or substitution does not result in the presence of a cysteine residue or with (ii) fifteen or less amino acid deletions.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 14 contains a nucleic acid sequence (SEQ ID NO:5) that can encode an ASBNP.1 polypeptide and a nucleic acid sequence (SEQ ID NO:6) that can encode an ASBNP.2 polypeptide.

high is 10 pmol; super high is 100 pmol; rec 1 is recovery 1; and rec 2 is recovery 2.

Figure 32:
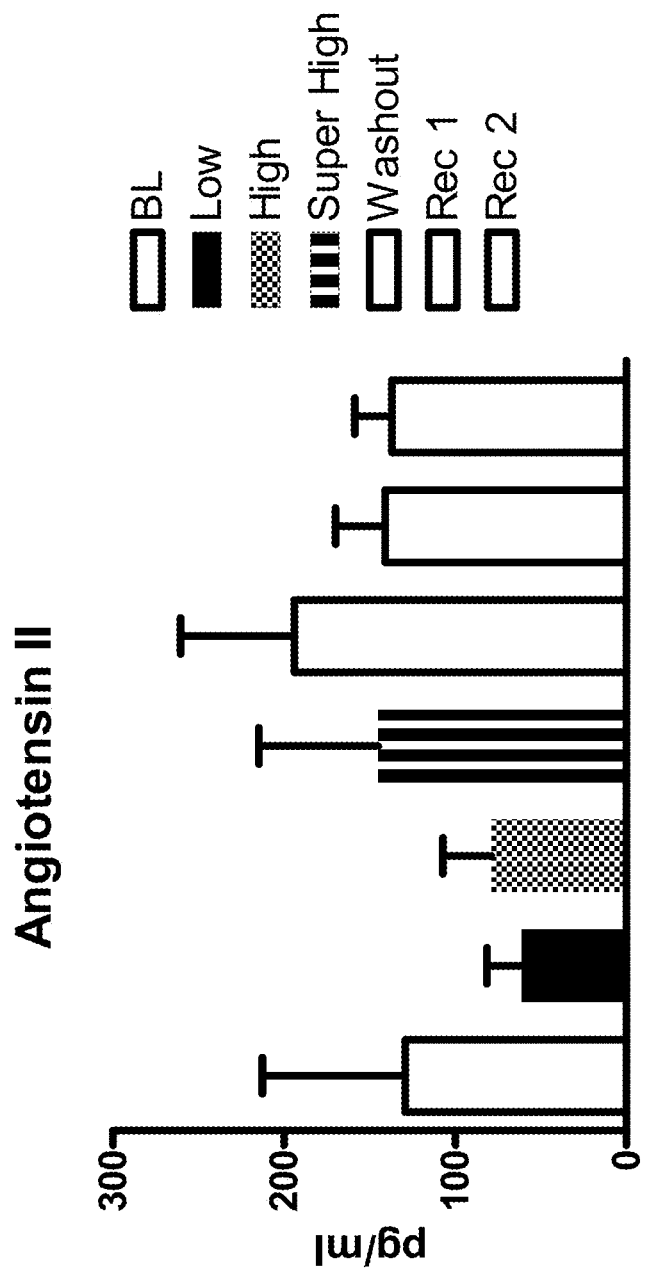

FIG. 32 is a bar graph plotting angiotensin II levels for paced dogs treated with ASBNP.1 as indicated. Baseline is prior to administration; low is 2 pmol; high is 10 pmol; super high is 100 pmol; rec 1 is recovery 1; and rec 2 is recovery 2.

Figure 33:
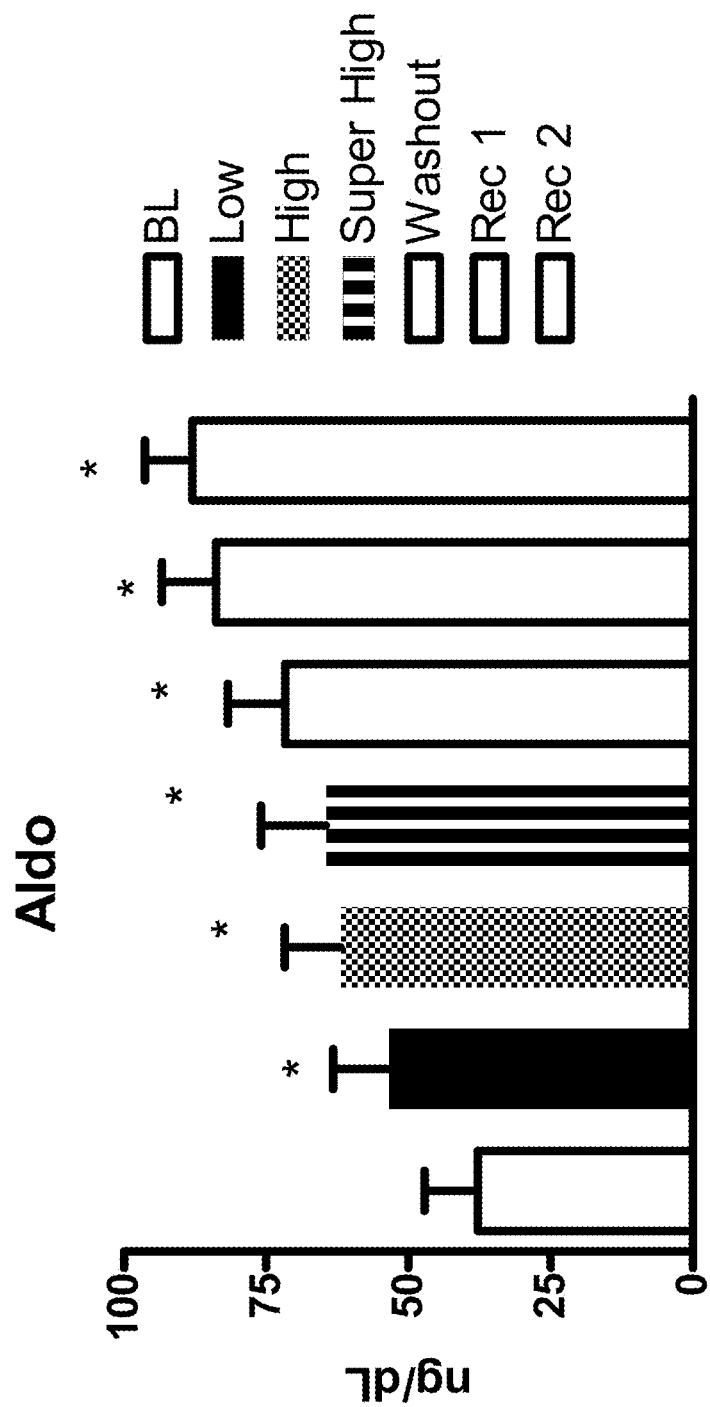

FIG. 33 is a bar graph plotting aldosterone levels for paced dogs treated with ASBNP.1 as indicated. Baseline is prior to administration; low is 2 pmol; high is 10 pmol; super high is 100 pmol; rec 1 is recovery 1; and rec 2 is recovery 2.

Figure 34:
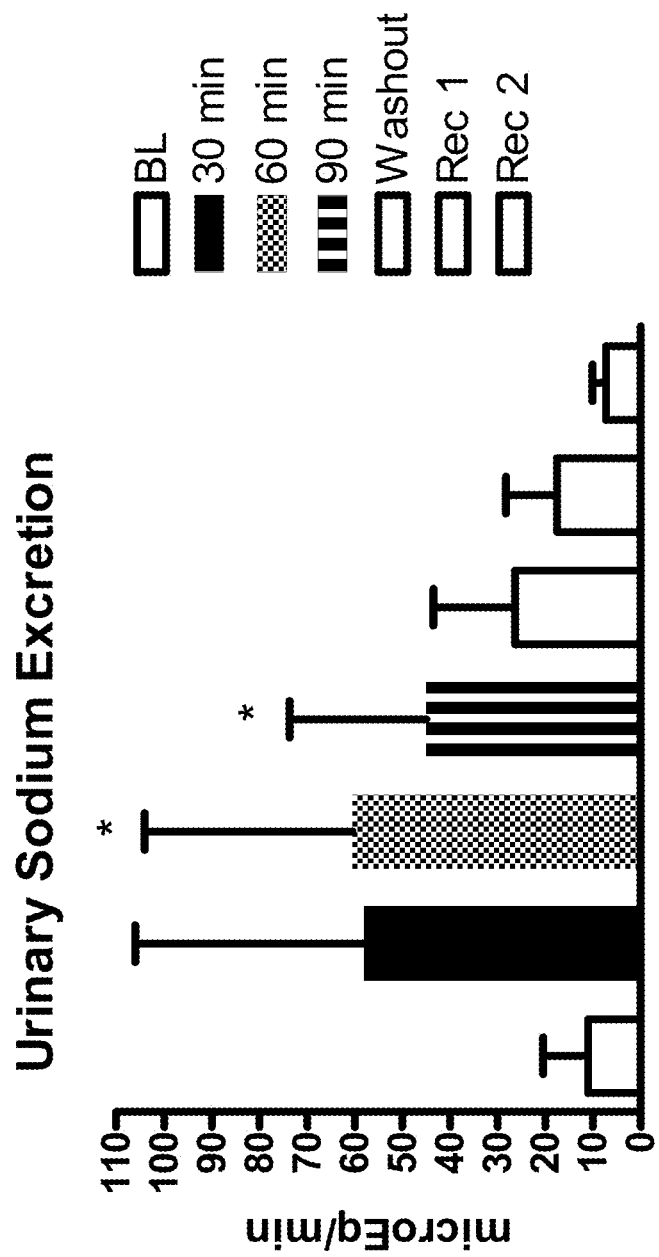

FIG. 34 is a graph plotting urinary sodium excretion (microEq/min) in paced dogs at the indicated times after beginning administration of ASBNP.1 polypeptide (100 pmol/kg/minute) for 90 minutes. BL=baseline; 30 min=30 minutes of ASBNP.1 polypeptide administration; 60 min=60 minutes of ASBNP.1 polypeptide administration; 90 min=90 minutes of ASBNP.1 polypeptide administration; Washout=after washout period at stop of infusion; Rec 1=30 minutes after stopping infusion; and Rec 2=60 minutes after stopping infusion.

Figure 35:
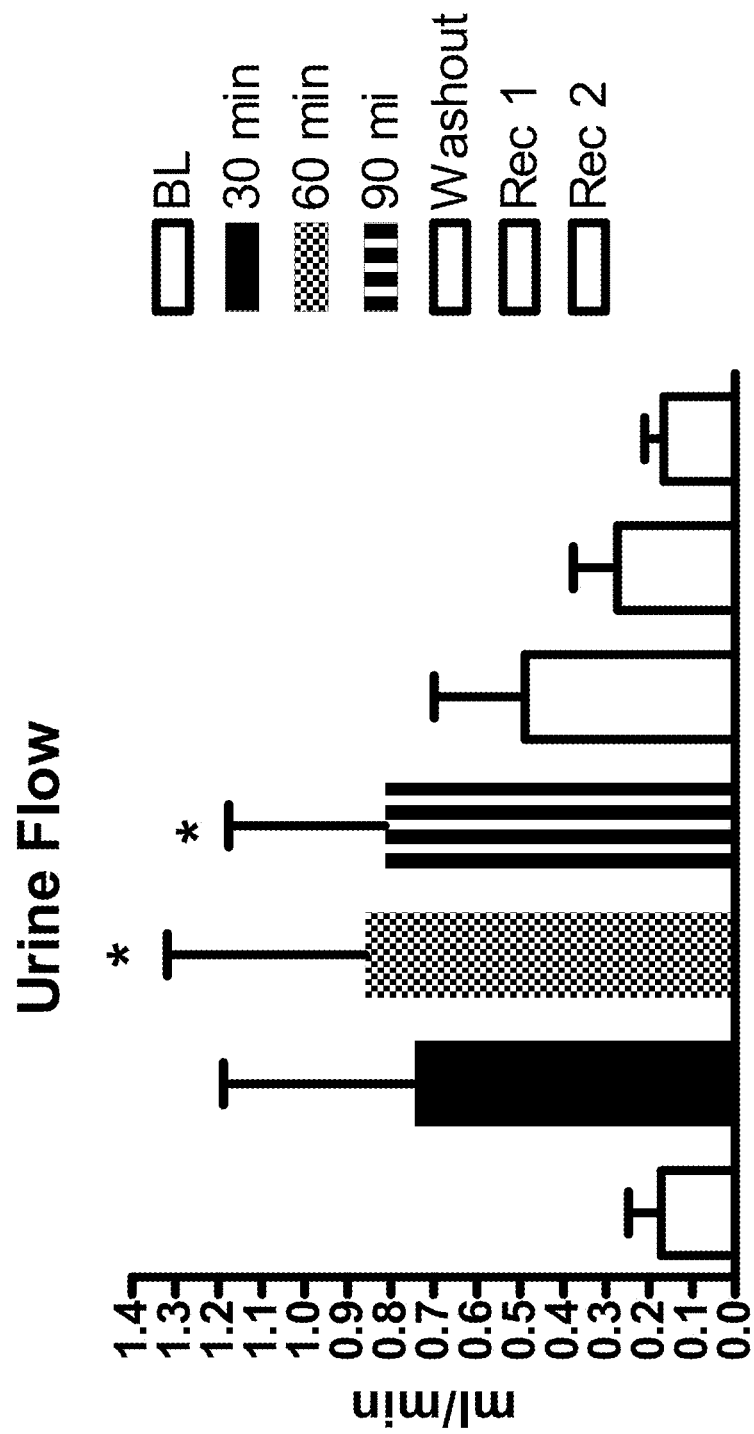

FIG. 35 is a graph plotting urine flow (mL/min) in paced dogs at the indicated times after beginning administration of ASBNP.1 polypeptide (100 pmol/kg/minute) for 90 minutes. BL=baseline; 30 min=30 minutes of ASBNP.1 polypeptide administration; 60 min=60 minutes of ASBNP.1 polypeptide administration; 90 min=90 minutes of ASBNP.1 polypeptide administration; Washout=after washout period at stop of infusion; Rec 1=30 minutes after stopping infusion; and Rec 2=60 minutes after stopping infusion.

Figure 36:
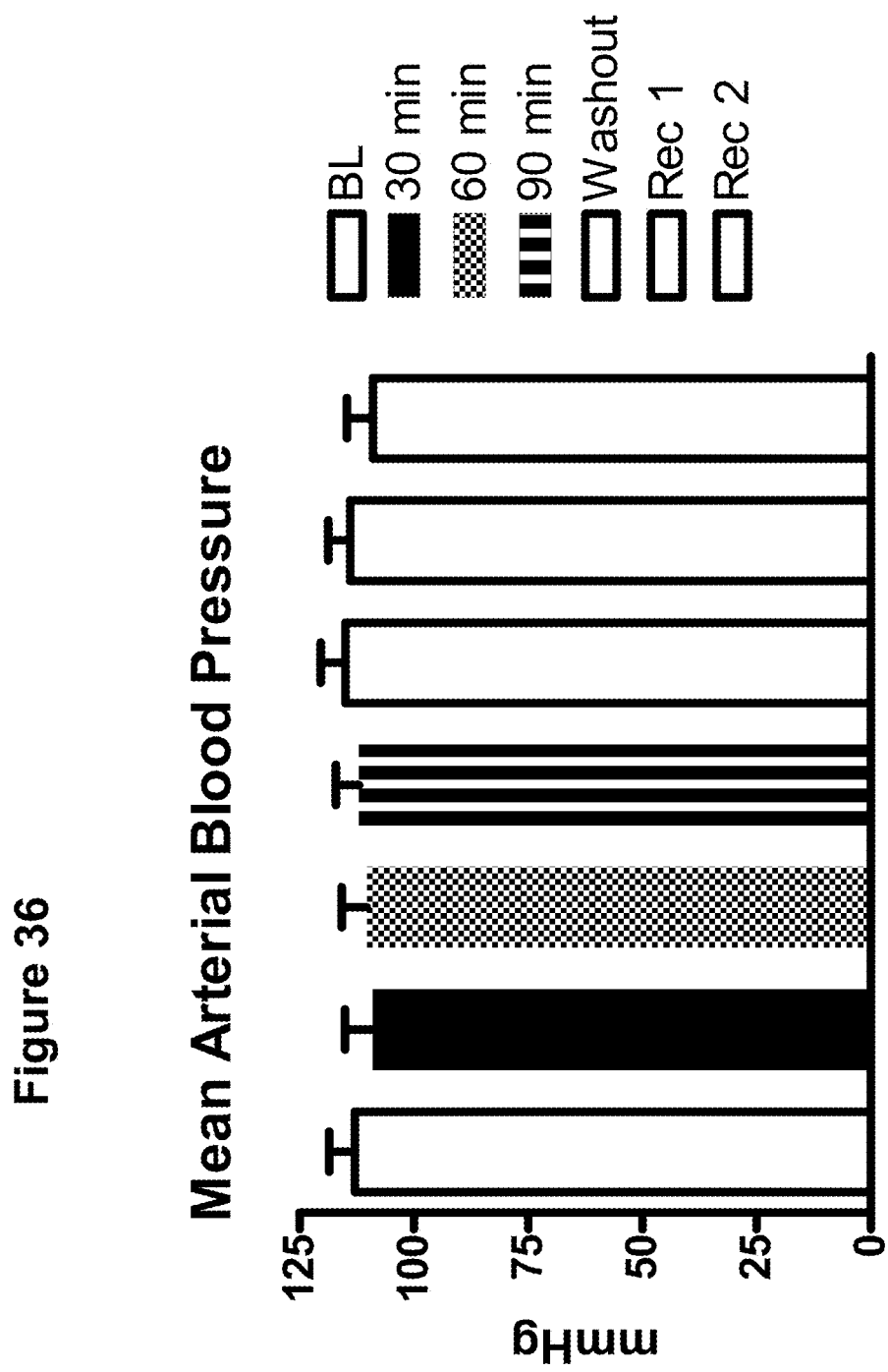

FIG. 36 is a graph plotting mean arterial blood pressure (mmHg) in paced dogs at the indicated times after beginning administration of ASBNP.1 polypeptide (100 pmol/kg/minute) for 90 minutes. BL=baseline; 30 min=30 minutes of ASBNP.1 polypeptide administration; 60 min=60 minutes of ASBNP.1 polypeptide administration; 90 min=90 minutes of ASBNP.1 polypeptide administration; Washout=after washout period at stop of infusion; Rec 1=30 minutes after stopping infusion; and Rec 2=60 minutes after stopping infusion.

Figure 37:
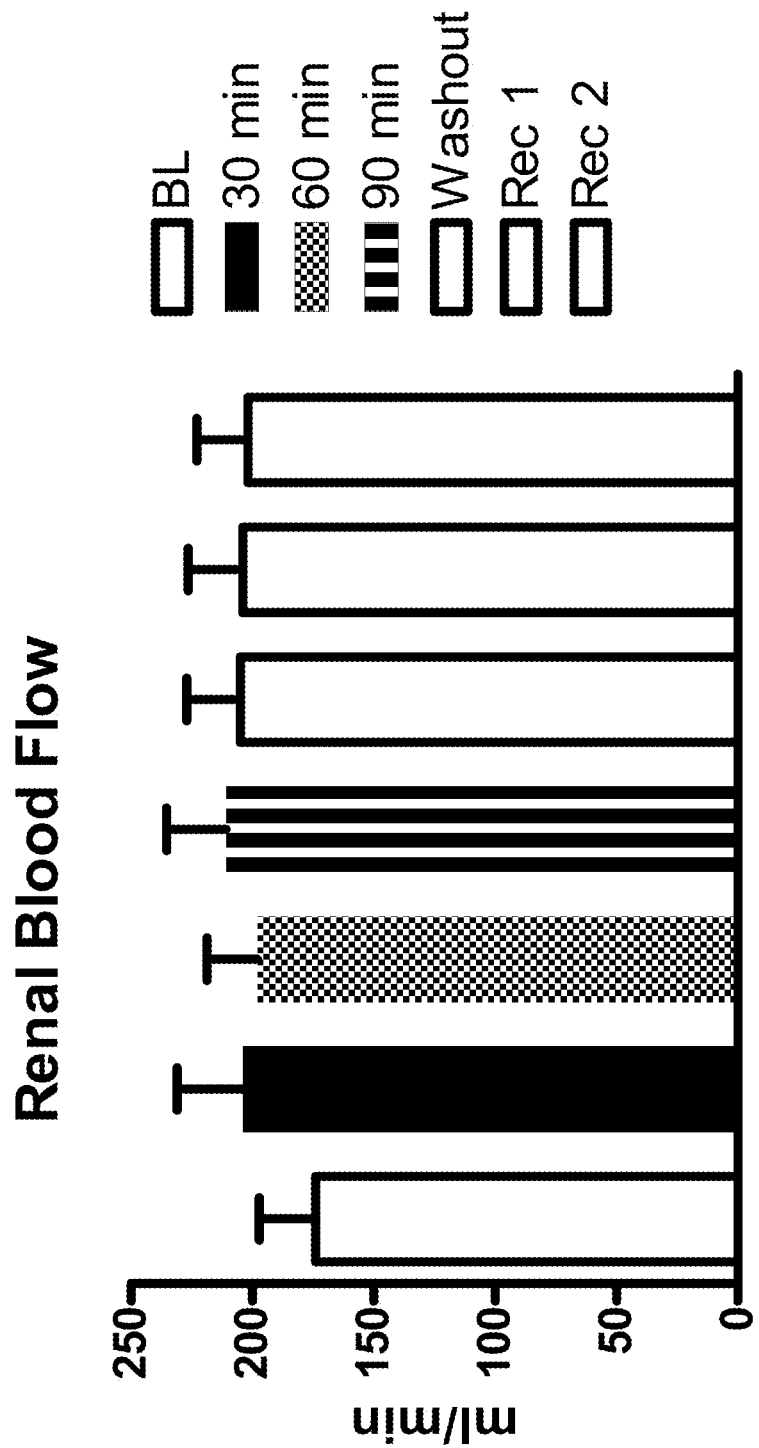

FIG. 37 is a graph plotting renal blood flow in paced dogs at the indicated times after beginning administration of ASBNP.1 polypeptide (100 pmol/kg/minute) for 90 minutes. BL=baseline; 30 min=30 minutes of ASBNP.1 polypeptide administration; 60 min=60 minutes of ASBNP.1 polypeptide administration; 90 min=90 minutes of ASBNP.1 polypeptide administration; Washout=after washout period at stop of infusion; Rec 1=30 minutes after stopping infusion; and Rec 2=60 minutes after stopping infusion.

Figure 38:
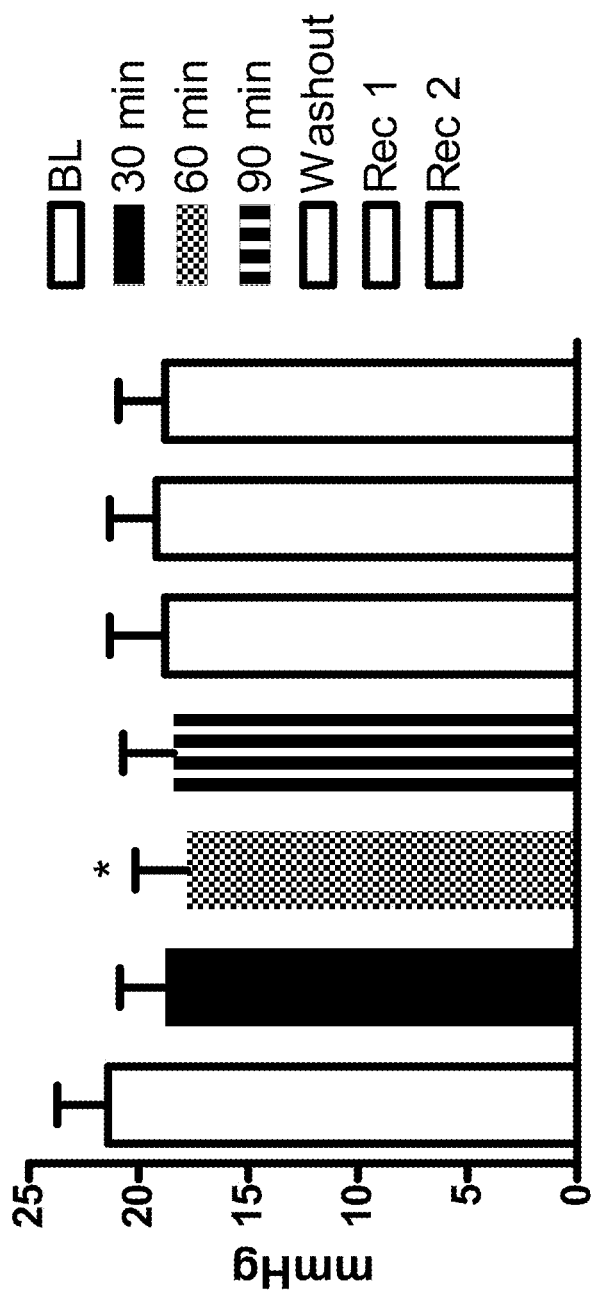

FIG. 38 is a graph plotting pulmonary capillary wedge pressure in paced dogs at the indicated times after beginning administration of ASBNP.1 polypeptide (100 pmol/kg/minute) for 90 minutes. BL=baseline; 30 min=30 minutes of ASBNP.1 polypeptide administration; 60 min=60 minutes of ASBNP.1 polypeptide administration; 90 min=90 minutes of ASBNP.1 polypeptide administration; Washout=after washout period at stop of infusion; Rec 1=30 minutes after stopping infusion; and Rec 2=60 minutes after stopping infusion.

Figure 39:
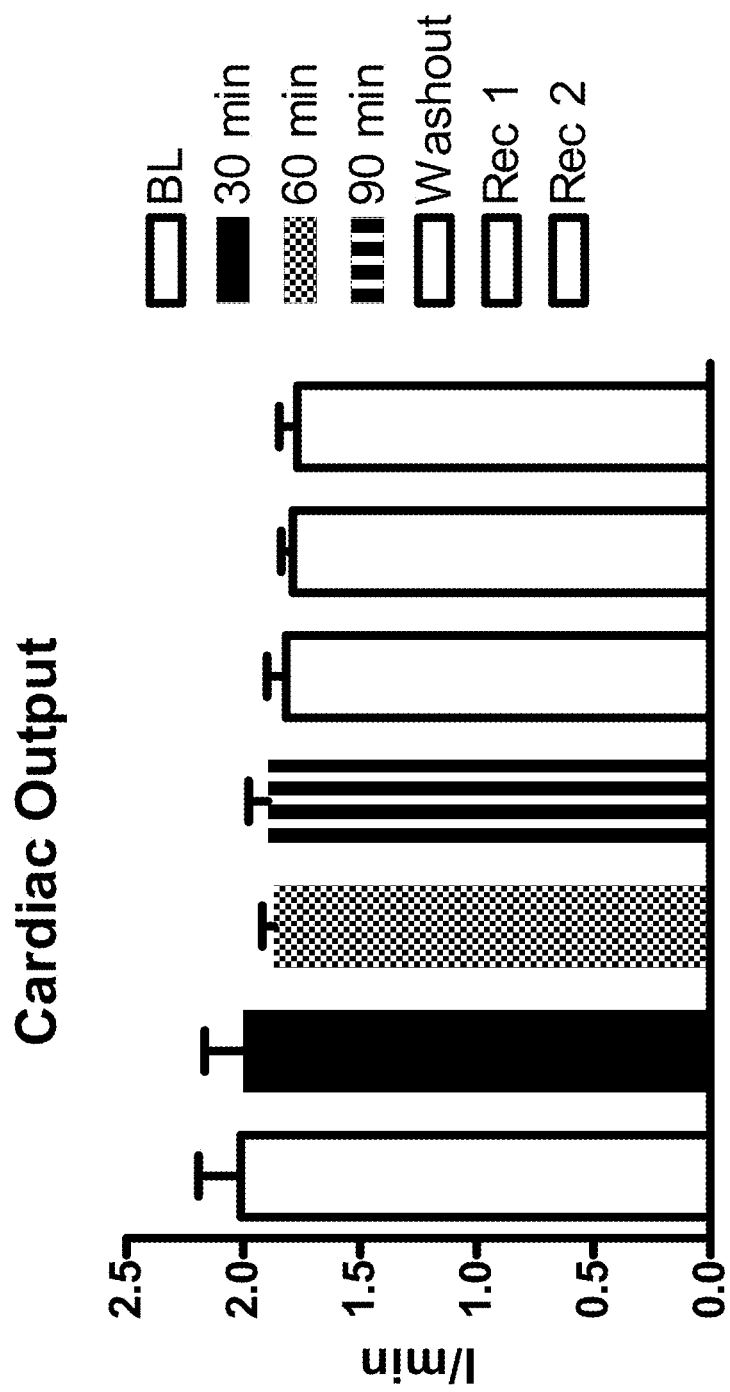

FIG. 39 is a graph plotting cardiac output (1/min) in paced dogs at the indicated times after beginning administration of ASBNP.1 polypeptide (100 pmol/kg/minute) for 90 minutes. BL=baseline; 30 min=30 minutes of ASBNP.1 polypeptide administration; 60 min=60 minutes of ASBNP.1 polypeptide administration; 90 min=90 minutes of ASBNP.1 polypeptide administration; Washout=after washout period at stop of infusion; Rec 1=30 minutes after stopping infusion; and Rec 2=60 minutes after stopping infusion.

DETAILED DESCRIPTION

This document relates to diuretic and natriuretic polypeptides. For example, this document provides polypeptides having diuretic and/or natriuretic activities. In some cases, a polypeptide provided herein can have diuretic and/or natriuretic activities, while lacking the ability to lower blood pressure. This document also provides methods and materials for inducing diuretic and/or natriuretic activities within a mammal.

A polypeptide provided herein can have any sequence and can have any length. For example, a polypeptide provided herein can include the sequence set forth in SEQ ID NO:1, SEQ ID NO:2, or SEQ ID NO:3. In some cases, a polypeptide provided herein can contain an amino acid sequence that aligns to the sequence set forth in SEQ ID NO:1, SEQ ID NO:2, or SEQ ID NO:3 with ten or less (e.g., nine or less, eight or less, seven or less, six or less, five or less, four or less, three or less, two or less, one, or zero) amino acid additions, deletions, substitutions, or combinations thereof For example, a polypeptide provided herein can contain the sequence set forth in SEQ ID NO:1 with the exception that first serine residue or the last valine residue of SEQ ID NO:1 is deleted or replaced with a different amino acid residue.

In some cases, a polypeptide provided herein can contain (a) a first amino acid sequence that either is set forth in SEQ ID NO:1 or aligns to the sequence set forth in SEQ ID NO:1 with ten or less (e.g., nine or less, eight or less, seven or less, six or less, five or less, four or less, three or less, two or less, one, or zero) amino acid deletions, substitutions, or combinations thereof and (b) a second amino acid sequence that either is set forth in SEQ ID NO:2 or aligns to the sequence set forth in SEQ ID NO:2 with either (i) ten or less (e.g., nine or less, eight or less, seven or less, six or less, five or less, four or less, three or less, two or less, one, or zero) amino acid additions, substitutions, or combinations thereof provided that the addition or substitution does not result in the presence of a cysteine residue or (ii) 15 or less (e.g., 14 or less, 13 or less, twelve or less, eleven or less, ten or less, nine or less, eight or less, seven or less, six or less, five or less, four or less, three or less, two or less, one, or zero) amino acid deletions. For example, a polypeptide provided herein can comprise or consist of the sequence set forth in SEQ ID NO:3 with the exception that the cysteine residue at position 43 of SEQ ID NO:3 is an amino acid other than cysteine (e.g., alanine, arginine, asparagines, aspartic acid, glutamine, glutamic acid, glycine, histidine, isoleucine, leucine, lysine, methionine, phenylalanine, praline, serine, threonine, tryptophan, tyrosine, or valine).

Polypeptides having one or more amino acid substitutions relative to a polypeptide sequence set forth in SEQ ID NO:1, SEQ ID NO:2, or SEQ ID NO:3 can be prepared and modified as described herein. Amino acid substitutions can be conservative or non-conservative amino acid substitutions. Conservative amino acid substitutions include, for example, substitution of an acidic amino acid residue (e.g., aspartic acid or glutamic acid) with another acidic amino acid residue, substitution of a basic amino acid residue (e.g., lysine, arginine, or histidine) with another basic amino acid residue, substitution of a hydrophobic amino acid residue with another hydrophobic amino acid residue (e.g., substitution of leucine with isoleucine, methionine with valine, or alanine with valine), and substitution of a hydrophilic amino acid residue (e.g., serine, glycine, or threonine) with another hydrophilic amino acid residue.

Conservative amino acid substitutions also include substitution of an amino acid residue having a particular type of side chain with another amino acid residue having a similar type of side chain. For example, conservative amino acid substitutions include substitution of an amino acid residue having an aliphatic side chain (e.g., glycine, alanine, valine, leucine, or isoleucine) with another amino acid residue having an aliphatic side chain, substitution of an amino acid residue having an aliphatic-hydroxyl side chain (e.g., serine or threonine) with another amino acid residue having an aliphatic-hydroxyl side chain, substitution of an amino acid residue having an amide-containing side chain (e.g., asparagine or glutamine) with another amino acid residue having an amide-containing side chain, substitution of an amino acid residue having an aromatic side chain (e.g., phenylalanine, tyrosine, or tryptophan) with another amino acid residue having an aromatic side chain, substitution of an amino acid residue having a basic side chain (e.g., lysine, arginine, or histidine) with another amino acid residue having a basic side chain, and substitution of an amino acid residue having a sulfur-containing side chain (e.g., cysteine or methionine) with another amino acid residue having a sulfur-containing side chain.

A polypeptide provided herein can have any length. For example, a polypeptide provided herein can be between 25 and 75 (e.g., between 30 and 70, between 32 and 60, between 32 and 57, between 32 and 50, between 32 and 45, between 35 and 43, or between 38 and 43) amino acid residues in length. It will be appreciated that a polypeptide with a length of 25 or 75 amino acid residues is a polypeptide with a length between 25 and 75 amino acid residues.

In some cases, a polypeptide provided herein can be between 37 and 47 amino acid residues in length and can comprise an amino acid sequence (a) set forth in SEQ ID NO:1 or (b) that aligns to the sequence set forth in SEQ ID NO:1 with five or less amino acid additions, deletions, substitutions, or combinations thereof. An example of such a polypeptide includes, without limitation, an ASBNP.1 polypeptide. In some cases, a polypeptide provided herein can be between 45 and 65 amino acid residues in length and can comprise (a) a first amino acid sequence that either is set forth in SEQ ID NO:1 or aligns to the sequence set forth in SEQ ID NO:1 with five or less amino acid deletions, substitutions, or combinations thereof and (b) a second amino acid sequence that either is set forth in SEQ ID NO:2 or aligns to the sequence set forth in SEQ ID NO:2 with (i) five or less amino acid additions, substitutions, or combinations thereof provided that the addition or substitution does not result in the presence of a cysteine residue or (ii) fifteen or less amino acid deletions. An example of such a polypeptide includes, without limitation, an ASBNP.2 polypeptide.

In some cases, a polypeptide provided herein can be a substantially pure polypeptide. As used herein, the term "substantially pure" with reference to a polypeptide means that the polypeptide is substantially free of other polypeptides, lipids, carbohydrates, and nucleic acid with which it is naturally associated. Thus, a substantially pure polypeptide is any polypeptide that is removed from its natural environment and is at least 60 percent pure or is any chemically synthesized polypeptide. A substantially pure polypeptide can be at least about 60, 65, 70, 75, 80, 85, 90, 95, or 99 percent pure.

Typically, a substantially pure polypeptide will yield a single major band on a non-reducing polyacrylamide gel.

In some embodiments, a polypeptide provide herein can lack the ability to stimulate production of cGMP in human umbilical vascular endothelial cells (HUVEC). Intracellular cGMP production can be assayed using, for example, the BIOTRACK cGMP enzyme immunoassay kit (Amersham Pharmacia Biotech). In other embodiments, a polypeptide provide herein can lack vasoactivity. Vasoactivity can be assessed by determining responsitivity of a blood vessel (e.g., a carotid artery in an organ chamber) to the polypeptide.

A polypeptide provide herein can be obtained by expression of a recombinant nucleic acid encoding the polypeptide or by chemical synthesis. For example, standard recombinant technology using expression vectors encoding a polypeptide provide herein can be used. The resulting polypeptides then can be purified using, for example, affinity chromatographic techniques and HPLC. The extent of purification can be measured by any appropriate method, including but not limited to: column chromatography, polyacrylamide gel electrophoresis, or high-performance liquid chromatography. A polypeptide provide herein can be designed or engineered to contain a tag sequence that allows the polypeptide to be purified (e.g., captured onto an affinity matrix). For example, a tag such as c-myc, hemagglutinin, polyhistidine, or Flag™ tag (Kodak) can be used to aid polypeptide purification. Such tags can be inserted anywhere within the polypeptide including at either the carboxyl or amino termini. Other fusions that can be used include enzymes that aid in the detection of the polypeptide, such as alkaline phosphatase.

A polypeptide provided herein can be produced that contains two regions, a first region that includes the N-terminus and ring structure of a mature natriuretic polypeptide (e.g., BNP, DNP, ANP, or CNP) and a second region that includes a mutated or truncated version of the C-terminal portion of ASBNP. The N-termini and ring structures of BNP, DNP, ANP, and CNP are described elsewhere. See, e.g., U.S. patent application Ser. No. 10/561,014.

A polypeptide provided herein can be formulated as a pharmaceutical composition by admixture with pharmaceutically acceptable non-toxic excipients or carriers. Such compositions can be administered to a subject in need thereof in an amount effective to treat, for example, heart, liver, kidney, or other sodium retaining conditions. For example, such compositions can be administered to a subject having a renal dysfunction. A renal dysfunction can include, without limitation, acute renal failure, glomerulonephritis, chronic renal failure, azotemia, uremia, immune renal disease; acute nephritic syndrome, rapidly progressive nephritic syndrome, nephrotic syndrome, Berger's Disease, chronic nephritic/proteinuric syndrome, tubulointerstital disease, nephrotoxic disorders, renal infarction, atheroembolic renal disease, renal cortical necrosis, malignant nephroangiosclerosis, renal vein thrombosis, renal tubular acidosis, renal glucosuria, nephrogenic diabetes insipidus, Bartter's Syndrome, Liddle's Syndrome, polycystic renal disease, interstitial nephritis, acute hemolytic uremic syndrome, medullary cystic disease, medullary sponge kidney, hereditary nephritis, and nail-patella syndrome.

Compositions provided herein also can be administered to a subject having a heart dysfunction. A heart dysfunction can include, without limitation, CHF, dilated congestive cardiomyopathy, hypertrophic cardiomyopathy, restrictive cardiomyopathy, mitral valve disease, aortic valve disease, tricuspid valve disease, angina pectoris, myocardial infarction, cardiac arrhythmia, pulmonary hypertension, arterial hypertension, renovascular hypertension, arteriosclerosis, atherosclerosis, and cardiac tumors.

Compositions provided herein also can be administered to a subject having an inflammatory condition. An inflammatory condition can include, without limitation, myocarditis, asthma, chronic inflammation, autoimmune diabetes, tumor angiogenesis, rheumatoid arthritis, rheumatoid spondylitis, osteoarthritis, gouty arthritis and other arthritic conditions, sepsis, septic shock, endotoxic shock, Gram-negative sepsis, toxic shock syndrome, asthma, adult respiratory distress syndrome, stroke, reperfusion injury, CNS injuries such as neural trauma and ischemia, psoriasis restenosis, cerebral malaria, chronic pulmonary inflammatory disease, silicosis, pulmonary sarcosis, bone resorption diseases such as osteoporosis, graft versus host reaction, Crohn's Disease, ulcerative colitis including inflammatory bowel disease (IBD), and pyresis.

Pharmaceutical compositions may be prepared for parenteral administration, particularly in the form of liquid solutions or suspensions in aqueous physiological buffer solutions; for oral administration, particularly in the form of tablets or capsules; or for intranasal administration, particularly in the form of powders, nasal drops, or aerosols. Compositions for other routes of administration may be prepared as desired using standard methods.

Formulations for parenteral administration may contain as common excipients sterile water or saline, polyalkylene glycols such as polyethylene glycol, oils of vegetable origin, hydrogenated naphthalenes, and the like. In particular, biocompatible, biodegradable lactide polymer, lactide/glycolide copolymer, or polyoxethylene-polyoxypropylene copolymers are examples of excipients for controlling the release of the polypeptide in vivo. Other suitable parenteral delivery systems include ethylene-vinyl acetate copolymer particles, osmotic pumps, implantable infusion systems, and liposomes. Formulations for inhalation administration may contain excipients such as lactose, if desired. Inhalation formulations may be aqueous solutions containing, for example, polyoxyethylene-9-lauryl ether, glycocholate and deoxycholate, or they may be oily solutions for administration in the form of nasal drops. If desired, the compounds can be formulated as gels to be applied intranasally. Formulations for parenteral administration may also include glycocholate for buccal administration For oral administration, tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g. magnesium stearate, talc or silica); disintegrants (e.g., potato starch or sodium starch glycolate); or wetting agents (e.g., sodium lauryl sulfate). Tablets can be coated by methods known in the art. Preparations for oral administration can also be formulated to give controlled release of the compound.

Nasal preparations can be presented in a liquid form or as a dry product. Nebulised aqueous suspensions or solutions can include carriers or excipients to adjust pH and/or tonicity.

Polypeptides described herein also can be formulated for topical delivery. Topical application and/or delivery of a polypeptide provided herein can be achieved using known methods, e.g., iontophoresis or lipogels.

Compositions described herein (e.g., including a polypeptide provided herein) can additionally include other active ingredients.

Various clinical parameters can be monitored prior to, during, and/or after administering a polypeptide described herein (e.g., formulated as a pharmaceutical composition) to a subject (e.g., a subject having a renal or heart dysfunction or an inflammatory condition). For example, vital signs, electrolytes, serum creatinine, cystatin, urinary BNP levels, plasma BNP levels, urine output, plasma levels of the administered polypeptide, urine levels of the administered polypeptide, or any combination thereof can be monitored. In some cases, plasma renin activity, glomerular filtration rate, urinary cGMP excretion, plasma cGMP levels, urinary ANP excretion, urinary BNP excretion, cardiac output, systemic vascular resistance, aldosterone levels, or any combination thereof can be monitored. Any appropriate method can be used to monitor clinical parameters including, without limitation, the methods described herein.

Monitoring clinical parameters can allow a clinician to determine whether or not an administered polypeptide is effective, e.g., whether or not the severity of a symptom of a heart or renal dysfunction or inflammatory condition has been reduced. In addition, monitoring clinical parameters before, during, and/or after administration of a polypeptide provided herein can indicate whether the dose of the polypeptide should be increased or decreased, whether administration of the polypeptide should be continued or discontinued, or whether the polypeptide should be re-administered. Monitoring clinical parameters also can indicate the severity of a subject's condition, which, in turn, can provide guidance as to when a polypeptide provided herein should be administered and at what dose.

Nucleic Acids Encoding Polypeptides

This document also provides isolated nucleic acids that encode one or more of the polypeptides provided herein. The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid (e.g., a nucleic acid encoding a polypeptide comprising or consisting of the amino acid sequence set forth in SEQ ID NO:1) can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence. A nucleic acid existing among hundreds to millions of other nucleic acids within, for example, cDNA libraries or genomic libraries, or gel slices containing a genomic DNA restriction digest, is not to be considered an isolated nucleic acid.

As used herein, the term "nucleic acid" refers to both RNA and DNA, including mRNA, cDNA, genomic DNA, synthetic (e.g., chemically synthesized) DNA, and nucleic acid analogs. The nucleic acid can be double-stranded or single-stranded, and where single-stranded, can be the sense strand or the antisense strand. In addition, nucleic acid can be circular or linear. Nucleic acid analogs can be modified at the base moiety, sugar moiety, or phosphate backbone to improve, for example, stability, hybridization, or solubility of a nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety can include modification of the 2' hydroxyl of the ribose sugar to form 2'—O-methyl or 2'—O-allyl sugars. The deoxyribose phosphate backbone can be modified to produce morpholino nucleic acids, in which each base moiety is linked to a six-membered, morpholino ring, or peptide nucleic acids, in which the deoxyphosphate backbone is replaced by a pseudopeptide backbone and the four bases are retained. See, for example, Summerton and Weller *Antisense Nucleic Acid Drug Dev.,* 7:187-195 (1997); and Hyrup et al. *Bioorgan. Med. Chem.,* 4:5-23 (1996). In addition, the deoxyphosphate backbone can be replaced with, for example, a phosphorothioate or phosphorodithioate backbone, a phosphoroamidite, or an alkyl phosphotriester backbone.

A nucleic acid provided herein can comprise or consist of the sequence set forth in SEQ ID NO:5 or 6.

Typically, an isolated nucleic acid provided herein is at least 10 nucleotides in length (e.g., 10, 15, 20, 25, 30, 35, 40, 50, 75, 100, 200, 300, 350, 400, or more nucleotides in length). Nucleic acid molecules that are less than full-length can be useful, for example, as primers or probes for diagnostic purposes. Isolated nucleic acid molecules can be produced by standard techniques, including, without limitation, common molecular cloning and chemical nucleic acid synthesis techniques. For example, polymerase chain reaction (PCR) techniques can be used. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 15 to 50 nucleotides in length, but can range from 10 nucleotides to hundreds of nucleotides in length. For example, a primer can be 12, 15, 16, 17, 18, 19, 20, 21, 22, 23, 24, 25, 26, 27, 28, 29, 30, 35, 40, or 45 nucleotides in length. A primer can be purified from a restriction digest by conventional methods, or can be chemically synthesized. Primers typically are single-stranded for maximum efficiency in amplification, but a primer can be double-stranded. Double-stranded primers are first denatured (e.g., treated with heat) to separate the strands before use in amplification. General PCR techniques are described, for example in *PCR Primer: A Laboratory Manual,* ed. by Dieffenbach and Dveksler, Cold Spring Harbor Laboratory Press, 1995. When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids as described elsewhere (Lewis, *Genetic Engineering News,* 12(9):1 (1992); Guatelli et al., *Proc. Natl. Acad. Sci. USA,* 87:1874-1878 (1990); and Weiss, *Science,* 254:1292 (1991)).

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids also can be obtained by mutagenesis. For example, a nucleic acid sequence encoding a polypeptide having the sequence set forth in SEQ ID NO:1, 2, or 3 can be mutated using standard techniques such as, for example, oligonucleotide-directed mutagenesis and/or site-directed mutagenesis through PCR. See, *Short Protocols in Molecular Biology,* Chapter 8, Green Publishing Associates and John Wiley & Sons, Edited by Ausubel et al., 1992. Such mutations include additions, deletions, substitutions, and combinations thereof.

Vectors and Host Cells

This document also provides vectors containing a nucleic acid provided herein. As used herein, a "vector" is a replicon, such as a plasmid, phage, or cosmid, into which another DNA segment may be inserted so as to bring about the replication of the inserted segment. A vector can be an expression vector. An "expression vector" is a vector that includes one or more expression control sequences, and an "expression control sequence" is a DNA sequence that controls and regulates the transcription and/or translation of another DNA sequence.

In an expression vector provided herein, the nucleic acid can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it can be necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the polypeptide encoded by the coding sequence.

Suitable expression vectors include, without limitation, plasmids and viral vectors derived from, for example, bacteriophage, baculoviruses, tobacco mosaic virus, herpes viruses, cytomegalovirus, retroviruses, poxviruses, adenoviruses, and adeno-associated viruses. Numerous vectors and expression systems are commercially available from such corporations as Novagen (Madison, Wis.), Clonetech (Palo Alto, Calif.), Stratagene (La Jolla, Calif.), and Invitrogen/Life Technologies (Carlsbad, Calif.).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide including at either the carboxyl or amino terminus.

This document also provides host cells containing a nucleic acid molecule and/or nucleic acid vector provided herein. The term "host cell" is intended to include prokaryotic and eukaryotic cells into which a nucleic acid molecule or vector can be introduced. Any method can be used to introduce nucleic acid into a cell. For example, calcium phosphate precipitation, electroporation, heat shock, lipofection, microinjection, and viral-mediated nucleic acid transfer can be used introduce nucleic acid into cells. In addition, naked DNA can be delivered directly to cells in vivo as described elsewhere (U.S. Pat. Nos. 5,580,859 and 5,589,466).

Detecting Polypeptides

This document provides methods and materials for detecting a polypeptide provided herein. Such methods and materials can be used to monitor polypeptide levels within a mammal receiving the polypeptide as a therapeutic. The polypeptide provided herein (e.g., ASBNP.1 and ASBNP.2) can be detected, for example, immunologically using one or more antibodies. As used herein, the term "antibody" includes intact molecules as well as fragments thereof that are capable of binding to an epitopic determinant of a polypeptide provided herein. The term "epitope" refers to an antigenic determinant on an antigen to which the paratope of an antibody binds. Epitopic determinants usually consist of chemically active surface groupings of molecules such as amino acids or sugar side chains, and typically have specific three-dimensional structural characteristics, as well as specific charge characteristics. Epitopes generally have at least five contiguous amino acids (a continuous epitope), or alternatively can be a set of noncontiguous amino acids that define a particular structure (e.g., a conformational epitope). The term "antibody" includes polyclonal antibodies, monoclonal antibodies, humanized or chimeric antibodies, single chain Fv antibody fragments, Fab fragments, and $F(ab)_2$ fragments. Polyclonal antibodies are heterogenous populations of antibody molecules that are contained in the sera of the immunized animals. Monoclonal antibodies are homogeneous populations of antibodies to a particular epitope of an antigen.

Antibody fragments that have specific binding affinity for a polypeptide provided herein (e.g., ASBNP.1 and ASBNP.2) can be generated by known techniques. For example, F(ab')2 fragments can be produced by pepsin digestion of the antibody molecule; Fab fragments can be generated by reducing the disulfide bridges of F(ab')2 fragments. Alternatively, Fab expression libraries can be constructed. See, for example, Huse et al., *Science,* 246:1275 (1989). Once produced, antibodies or fragments thereof are tested for recognition of a polypeptide provided herein by standard immunoassay methods including ELISA techniques, radioimmunoassays, and Western blotting. See, *Short Protocols in Molecular Biology,* Chapter 11, Green Publishing Associates and John Wiley & Sons, Edited by Ausubel, F. M et al., 1992.

In immunological assays, an antibody having specific binding affinity for a polypeptide provided herein or a secondary antibody that binds to such an antibody can be labeled, either directly or indirectly. Suitable labels include, without limitation, radionuclides (e.g. $^{125}$I, $^{131}$I, $^{35}$S, $^{3}$H, $^{32}$P, $^{33}$P, or $^{14}$C), fluorescent moieties (e.g., fluorescein, FITC, PerCP, rhodamine, or PE), luminescent moieties (e.g., Qdot™ nanoparticles supplied by the Quantum Dot Corporation, Palo Alto, Calif.), compounds that absorb light of a defined wavelength, or enzymes (e.g., alkaline phosphatase or horseradish peroxidase). Antibodies can be indirectly labeled by conjugation with biotin then detected with avidin or streptavidin labeled with a molecule described above. Methods of detecting or quantifying a label depend on the nature of the label and are known in the art. Examples of detectors include, without limitation, x-ray film, radioactivity counters, scintillation counters, spectrophotometers, colorimeters, fluorometers, luminometers, and densitometers. Combinations of these approaches (including "multi-layer" assays) familiar to those in the art can be used to enhance the sensitivity of assays.

Immunological assays for detecting a polypeptide provided herein can be performed in a variety of known formats, including sandwich assays, competition assays (competitive RIA), or bridge immunoassays. See, for example, U.S. Pat. Nos. 5,296,347; 4,233,402; 4,098,876; and 4,034,074. Methods of detecting a polypeptide provided herein generally include contacting a biological sample with an antibody that binds to a polypeptide provided herein and detecting binding of the polypeptide to the antibody. For example, an antibody having specific binding affinity for a polypeptide provided herein can be immobilized on a solid substrate by any of a variety of methods known in the art and then exposed to the biological sample. Binding of the polypeptide to the antibody on the solid substrate can be detected by exploiting the phenomenon of surface plasmon resonance, which results in a change in the intensity of surface plasmon resonance upon binding that can be detected qualitatively or quantitatively by an appropriate instrument, e.g., a Biacore apparatus (Biacore International AB, Rapsgatan, Sweden). Alternatively, the antibody is labeled and detected as described above. A standard curve using known quantities of a polypeptide provided herein can be generated to aid in the quantitation of the levels of the polypeptide.

In other embodiments, a "sandwich" assay in which a capture antibody is immobilized on a solid substrate is used to detect the presence, absence, or level of a polypeptide provided herein. The solid substrate can be contacted with the biological sample such that any polypeptide of interest in the sample can bind to the immobilized antibody. The presence, absence, or level of the polypeptide bound to the antibody can be determined using a "detection" antibody having specific binding affinity for the polypeptide. In some embodiments, a capture antibody can be used that has binding affinity for BNP as well as a polypeptide provided herein. In this embodiment, a detection antibody can be used that has specific binding affinity for a particular polypeptide provided herein. It is understood that in sandwich assays, the capture antibody should not bind to the same epitope (or range of epitopes in the case of a polyclonal antibody) as the detection antibody. Thus, if a monoclonal antibody is used as a capture antibody, the detection antibody can be another monoclonal antibody that binds to an epitope that is either completely physically separated from or only partially overlaps with the epitope to which the capture monoclonal antibody binds, or a polyclonal antibody that binds to epitopes other than or in addition to that to which the capture monoclonal antibody binds. If a polyclonal antibody is used as a capture antibody, the detection antibody can be either a monoclonal antibody that binds to an epitope that is either completely physically separated from or partially overlaps with any of the epitopes to which the capture polyclonal antibody binds, or a polyclonal antibody that binds to epitopes other than or in addition to that to which the capture polyclonal antibody binds. Sandwich assays can be performed as sandwich ELISA assays, sandwich Western blotting assays, or sandwich immunomagnetic detection assays.

Suitable solid substrates to which an antibody (e.g., a capture antibody) can be bound include, without limitation, microtiter plates, tubes, membranes such as nylon or nitrocellulose membranes, and beads or particles (e.g., agarose, cellulose, glass, polystyrene, polyacrylamide, magnetic, or magnetizable beads or particles). Magnetic or magnetizable particles can be particularly useful when an automated immunoassay system is used.

Antibodies having specific binding affinity for a polypeptide provided herein can be produced through standard methods. In general, a polypeptide can be recombinantly produced as described above, or can be purified from a biological sample (e.g., a heterologous expression system), and used to immunize host animals, including rabbits, chickens, mice, guinea pigs, or rats. For example, a polypeptide having the amino acid sequence set forth in SEQ ID NOs:1 or 2, or fragments thereof that are at least six amino acids in length, can be used to immunize an animal. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol. Monoclonal antibodies can be prepared using a polypeptide provided herein and standard hybridoma technology. In particular, monoclonal antibodies can be obtained by any technique that provides for the production of antibody molecules by continuous cell lines in culture such as described by Kohler et al., *Nature*, 256:495 (1975), the human B-cell hybridoma technique (Kosbor et al., *Immunology Today*, 4:72 (1983); Cole et al., *Proc. Natl. Acad. Sci. USA*, 80:2026 (1983)), and the EBV-hybridoma technique (Cole et al., "Monoclonal Antibodies and Cancer Therapy," Alan R. Liss, Inc., pp. 77-96 (1983)). Such antibodies can be of any immunoglobulin class including IgG, IgM, IgE, IgA, IgD, and any subclass thereof. The hybridoma producing the monoclonal antibodies can be cultivated in vitro and in vivo.

Alternative techniques for detecting a polypeptide provided herein include mass-spectrophotometric techniques such as electrospray ionization (ESI), and matrix-assisted laser desorption-ionization (MALDI). See, for example, Gevaert et al., *Electrophoresis*, 22(9):1645-51 (2001); Chaurand et al., *J. Am. Soc. Mass Spectrom.*, 10(2):91-103 (1999). Mass spectrometers useful for such applications are available from Applied Biosystems (Foster City, Calif.); Bruker Daltronics (Billerica, Mass.); and Amersham Pharmacia (Sunnyvale, Calif.).

The invention will be further described in the following examples, which do not limit the scope of the invention described in the claims.

EXAMPLES

Example 1

Biological Effects of ASBNP.1 Polypeptides

Figure 1:
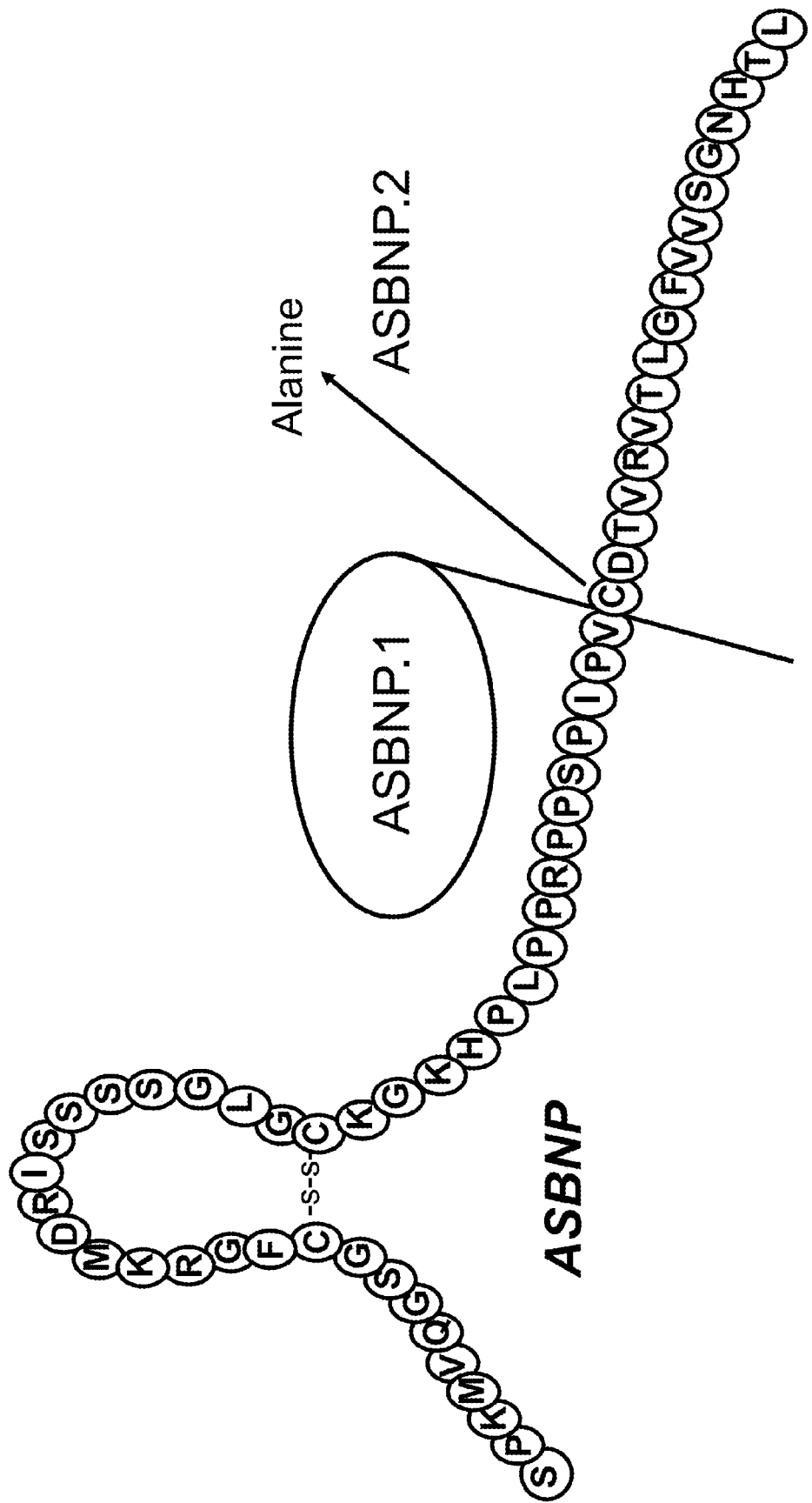
FIG. 1 is a schematic diagram of an ASBNP polypeptide that is 60 amino acid residues in length (SEQ ID NO:4), an ASBNP.1 polypeptide that is 42 amino acid residues in length (SEQ ID NO:1), an ASBNP.2 polypeptide that is 60 amino acid residues in length with an alanine at position 43 (SEQ ID NO:3). The sequence of ASBNP.2 from the alanine at position 43 to the leucine at position 60 is 18 amino acid residues in length (SEQ ID NO:2). ASBNP (also referred to as BNP2) is a variant form of BNP generated by alternative splicing.
Figure 2:
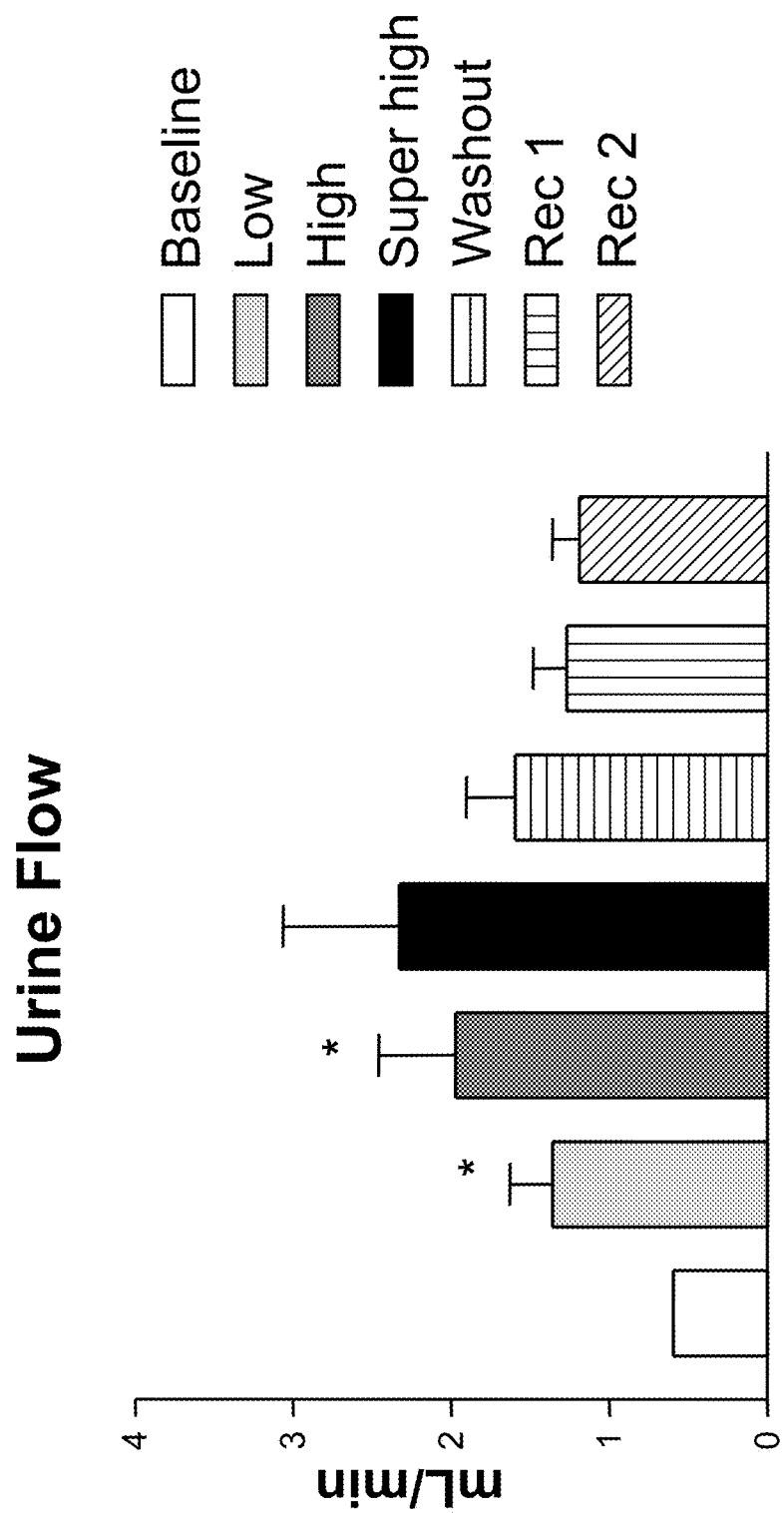
FIG. 2 is a bar graph plotting urine flow rates for dogs treated with ASBNP.1 as indicated. Baseline is prior to administration; low is 2 pmol; high is 10 pmol; super high is 100 pmol; rec 1 is recovery 1; and rec 2 is recovery 2.
Figure 3:
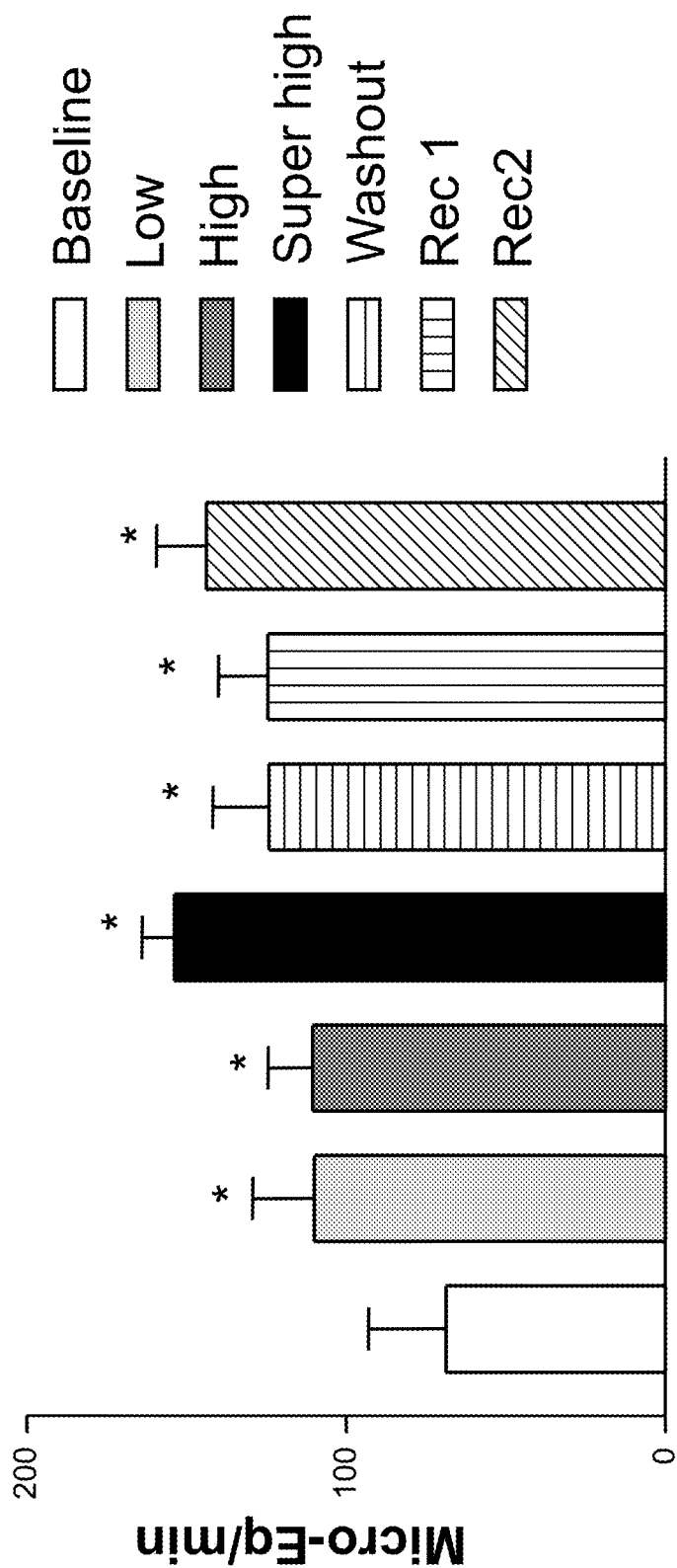
FIG. 3 is a bar graph plotting urinary sodium excretion rates for dogs treated with ASBNP.1 as indicated. Baseline is prior to administration; low is 2 pmol; high is 10 pmol; super high is 100 pmol; rec 1 is recovery 1; and rec 2 is recovery 2.
Figure 4:
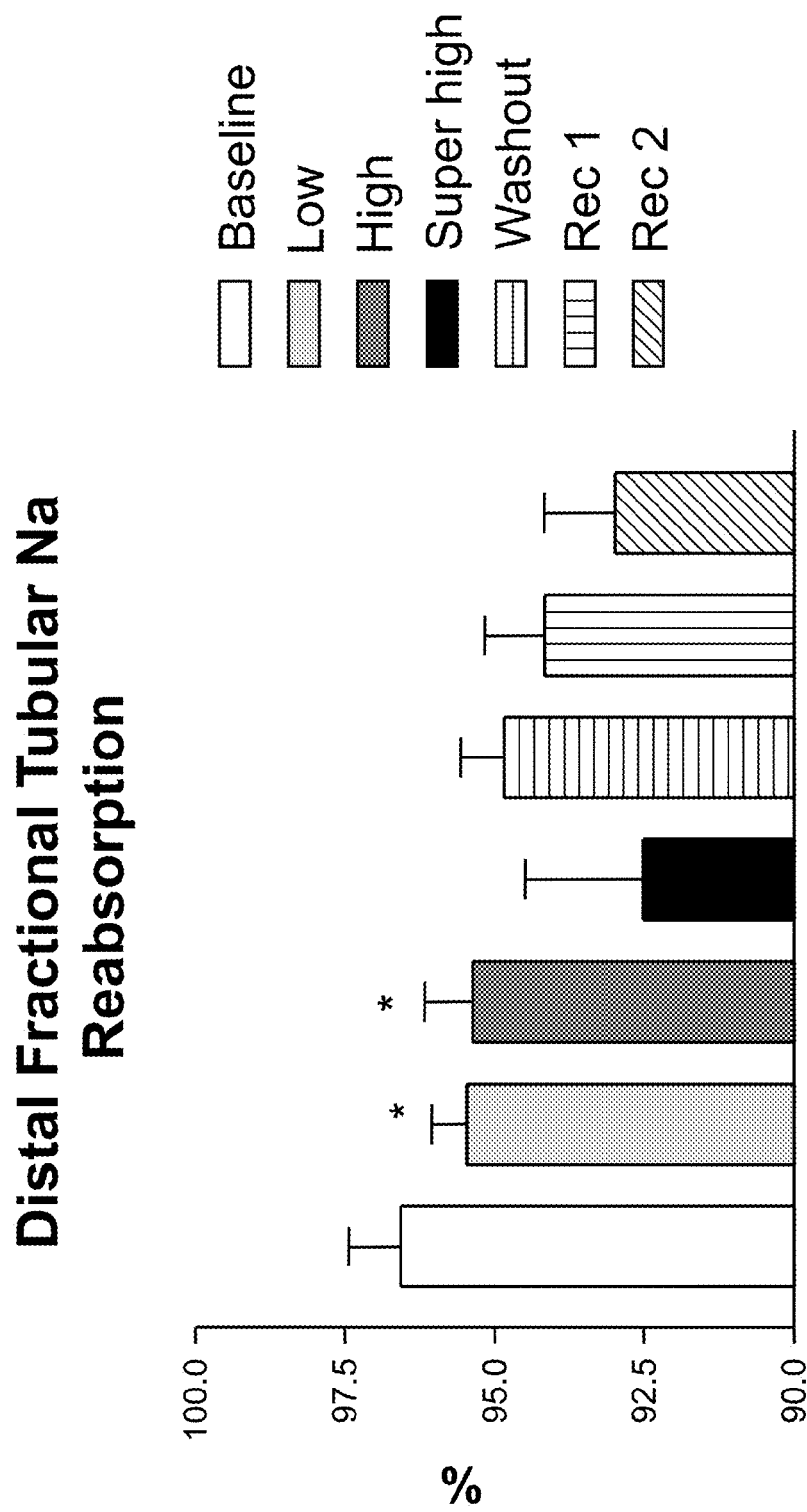
FIG. 4 is a bar graph plotting distal fractional tubular sodium reabsorption rates for dogs treated with ASBNP.1 as indicated. Baseline is prior to administration; low is 2 pmol; high is 10 pmol; super high is 100 pmol; rec 1 is recovery 1; and rec 2 is recovery 2.
Figure 5:
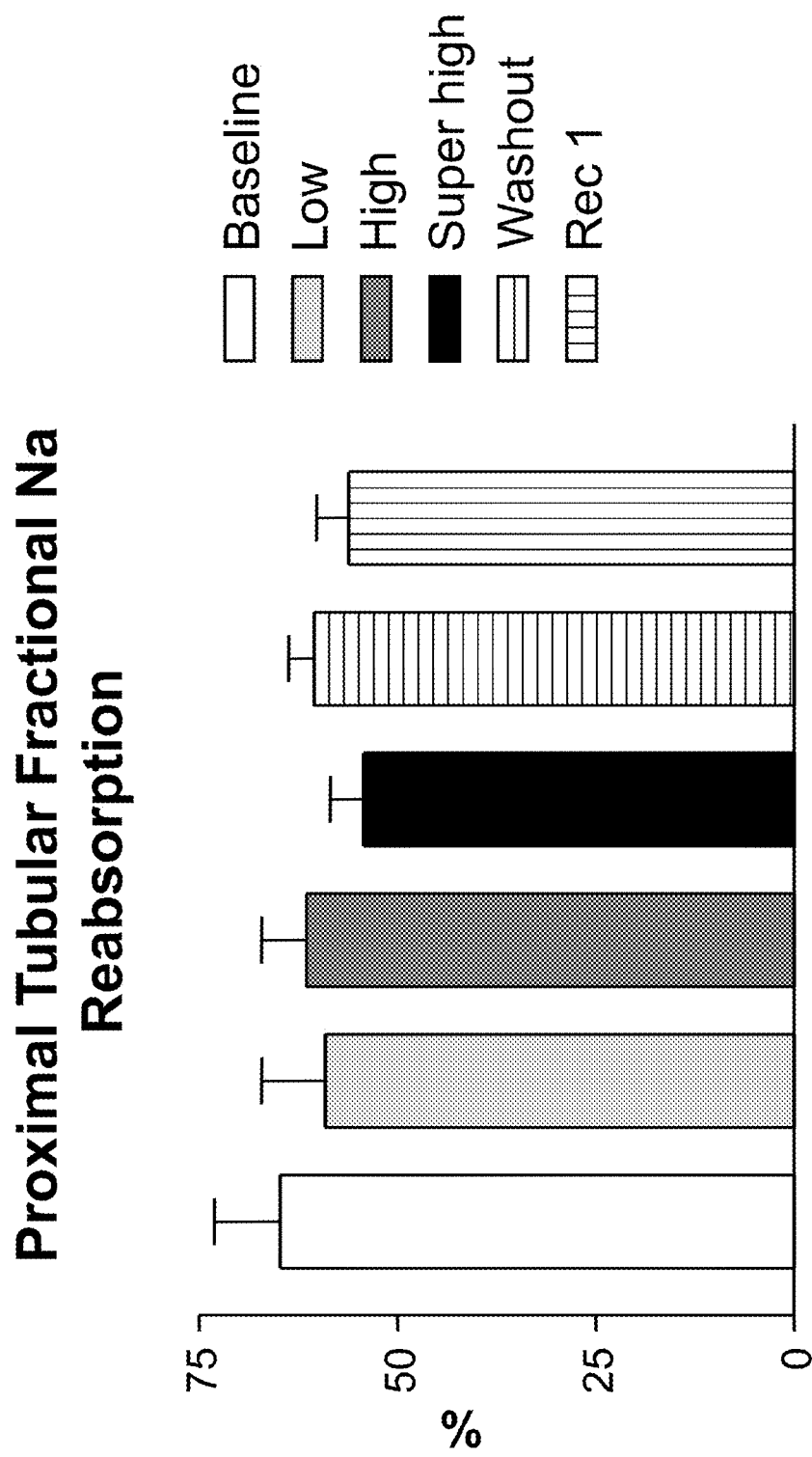
FIG. 5 is a bar graph plotting proximal tubular fractional sodium reabsorption rates for dogs treated with ASBNP.1 as indicated. Baseline is prior to administration; low is 2 pmol; high is 10 pmol; super high is 100 pmol; and rec 1 is recovery 1.
Figure 6:
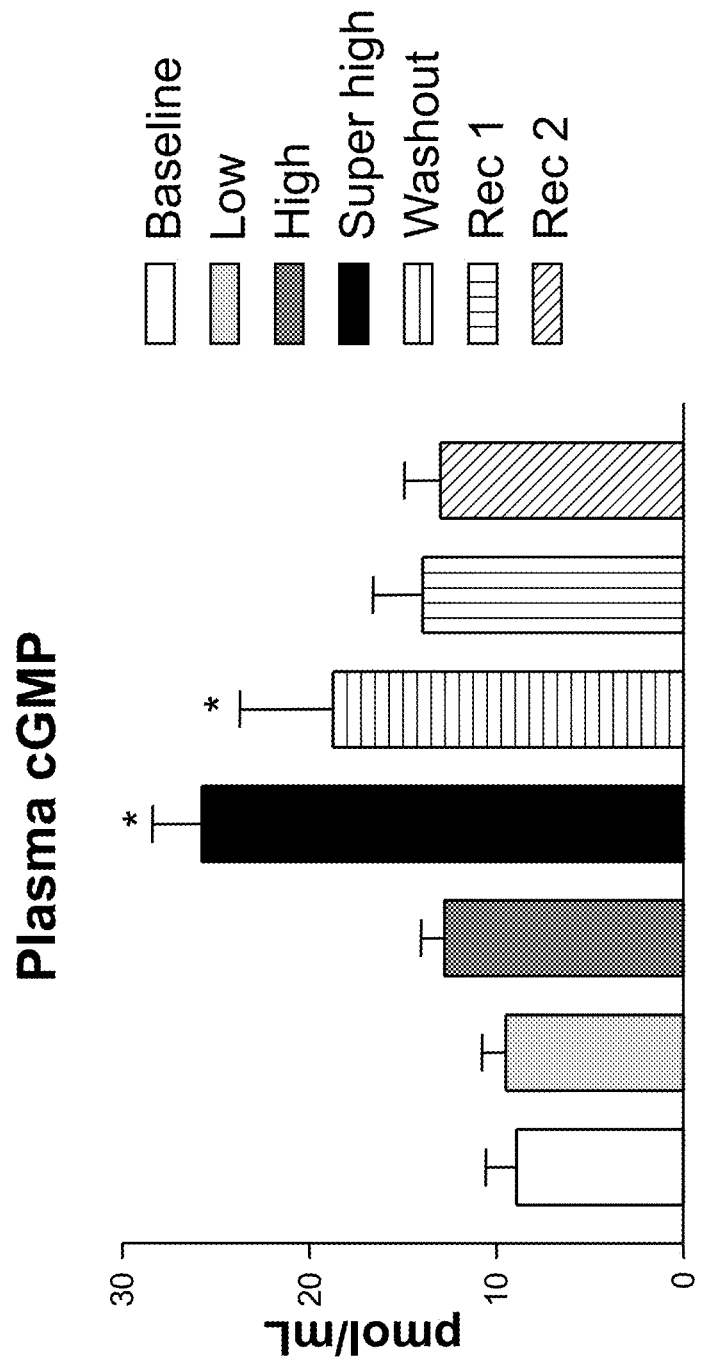
FIG. 6 is a bar graph plotting plasma cGMP levels for dogs treated with ASBNP.1 as indicated. Baseline is prior to administration; low is 2 pmol; high is 10 pmol; super high is 100 pmol; rec 1 is recovery 1; and rec 2 is recovery 2.
Figure 7:
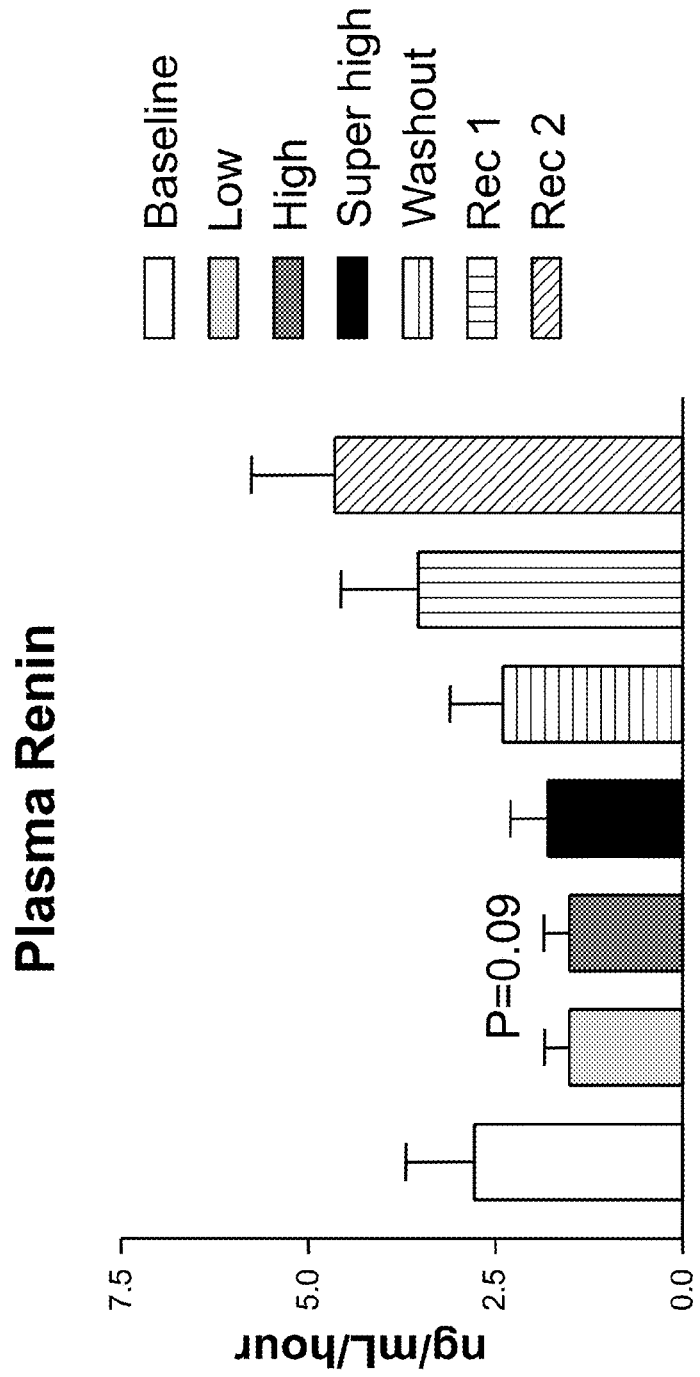
FIG. 7 is a bar graph plotting plasma renin activity for dogs treated with ASBNP.1 as indicated. Baseline is prior to administration; low is 2 pmol; high is 10 pmol; super high is 100 pmol; rec 1 is recovery 1; and rec 2 is recovery 2.
Figure 8:
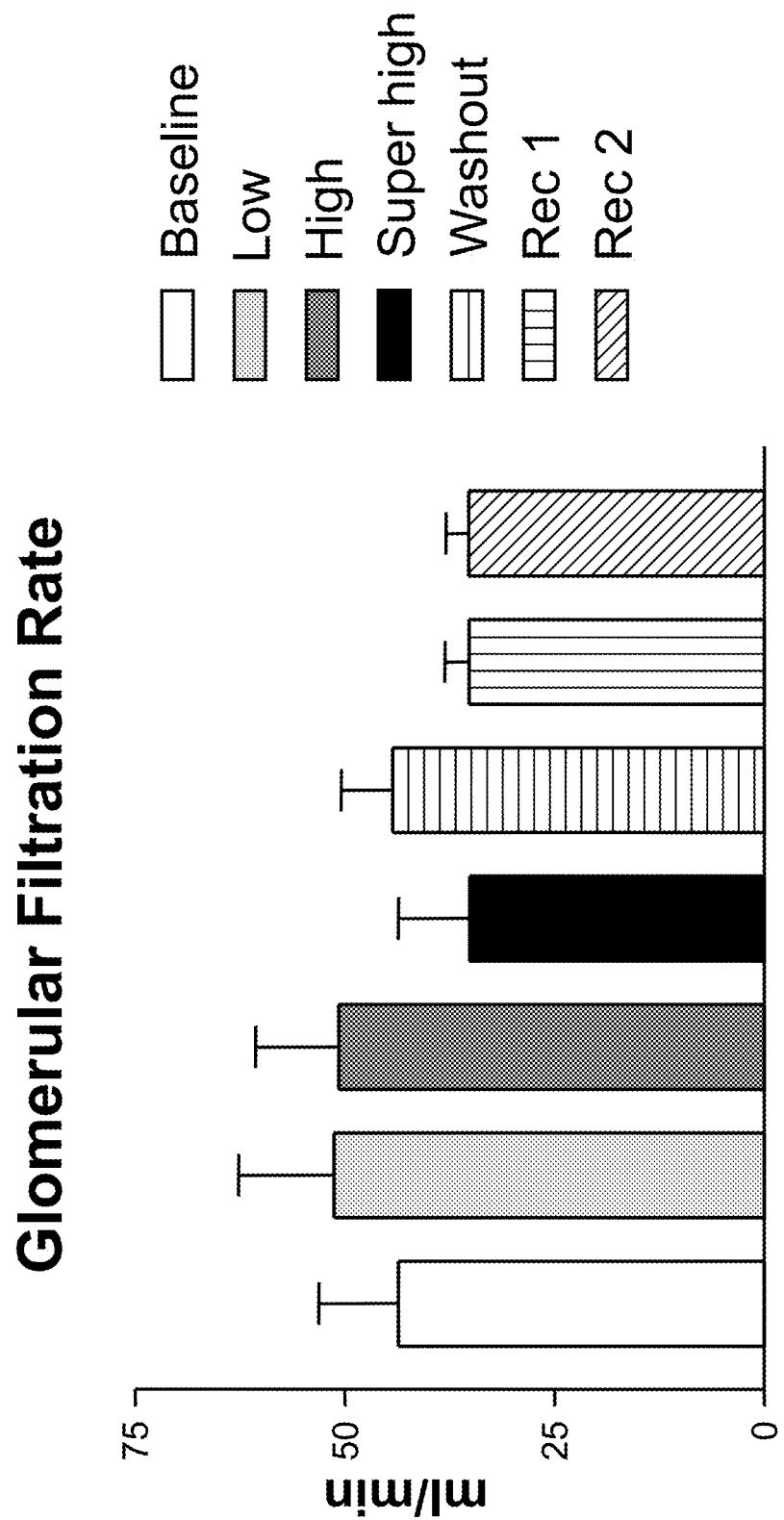
FIG. 8 is a bar graph plotting glomerular filtration rates for dogs treated with ASBNP.1 as indicated. Baseline is prior to administration; low is 2 pmol; high is 10 pmol; super high is 100 pmol; rec 1 is recovery 1; and rec 2 is recovery 2.
Figure 9:
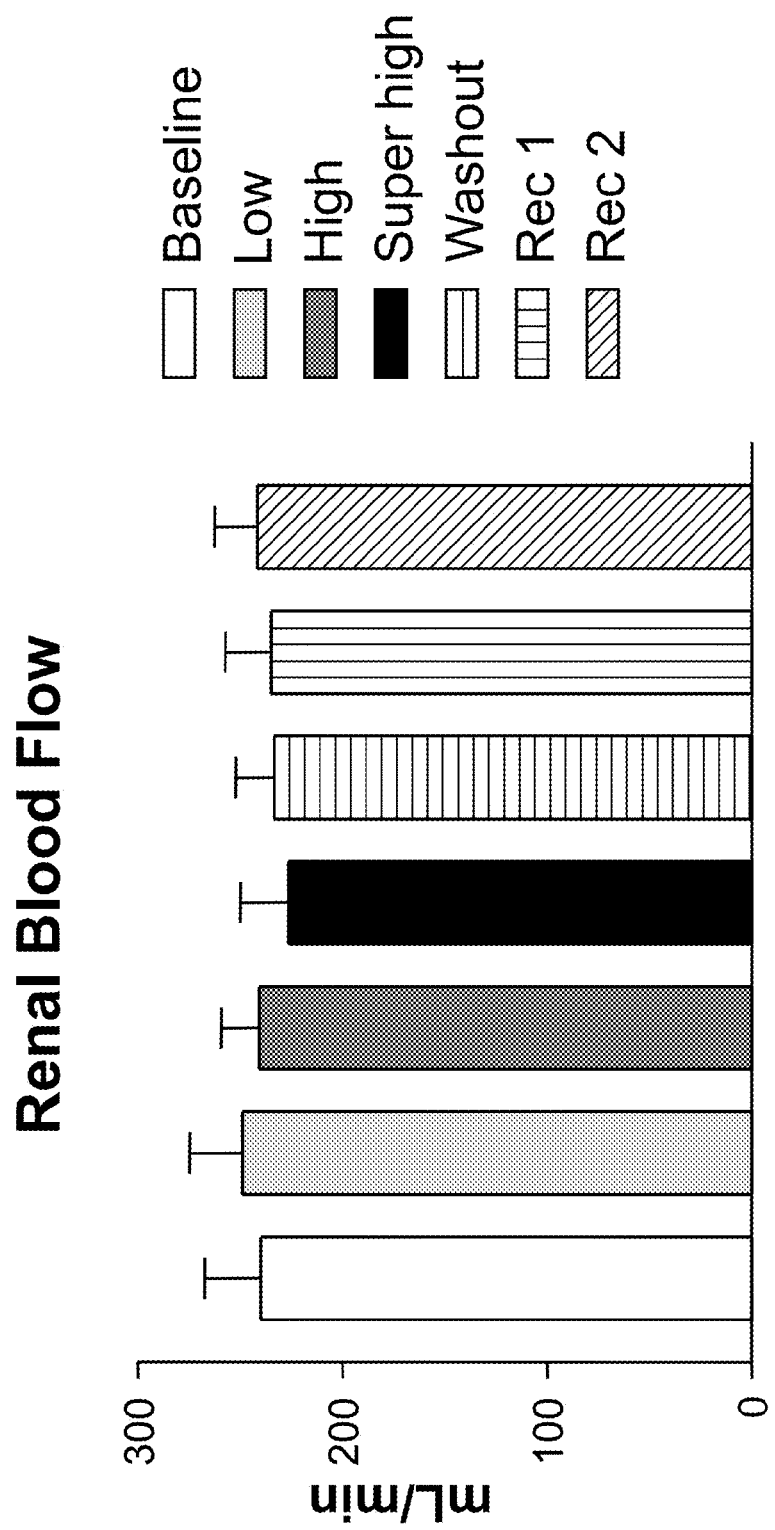
FIG. 9 is a bar graph plotting renal blood flow rates for dogs treated with ASBNP.1 as indicated. Baseline is prior to administration; low is 2 pmol; high is 10 pmol; super high is 100 pmol; rec 1 is recovery 1; and rec 2 is recovery 2.
Figure 10:
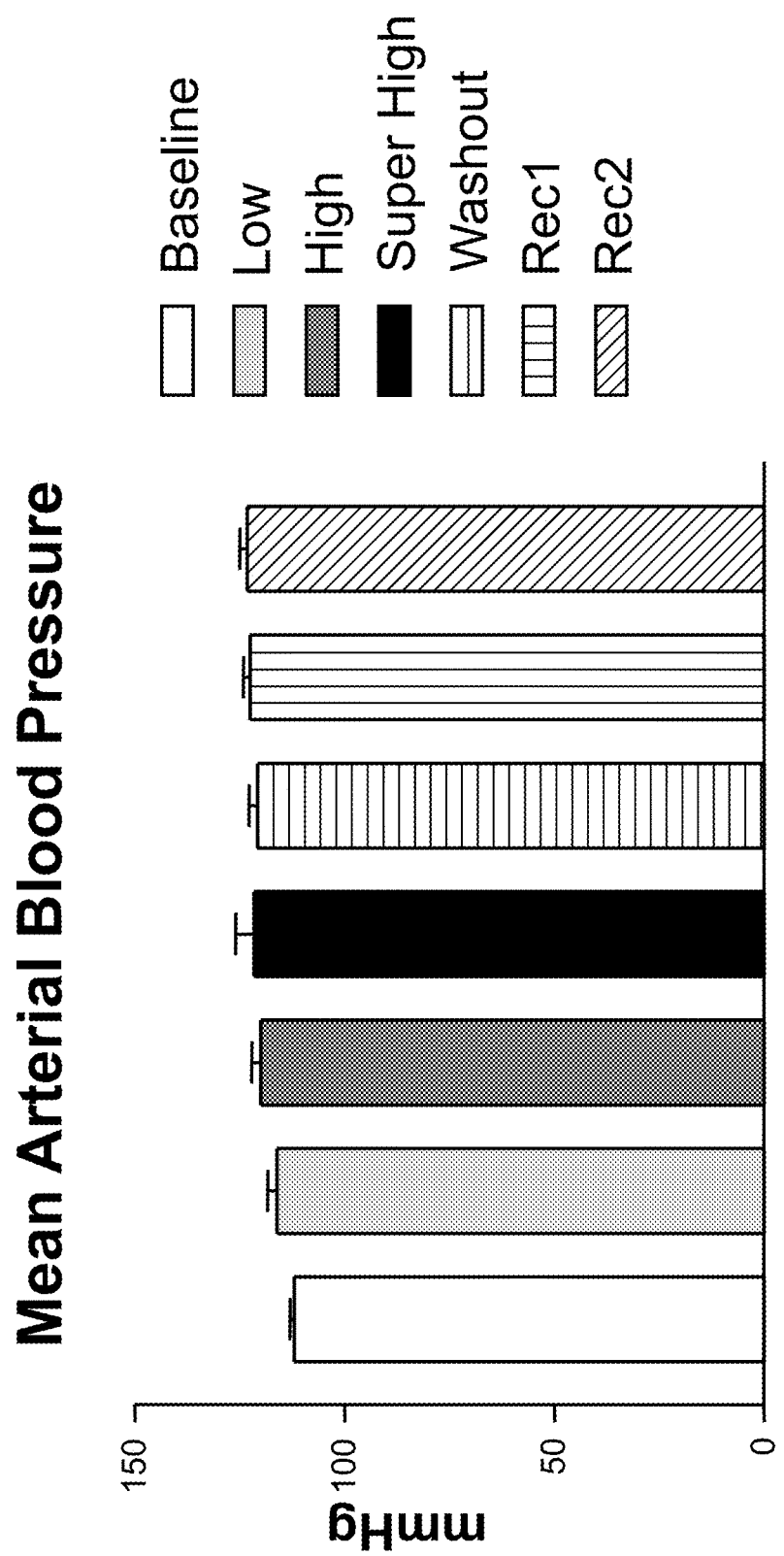
FIG. 10 is a bar graph plotting mean arterial blood pressure levels for dogs treated with ASBNP.1 as indicated. Baseline is prior to administration; low is 2 pmol; high is 10 pmol; super high is 100 pmol; rec 1 is recovery 1; and rec 2 is recovery 2.
Figure 11:
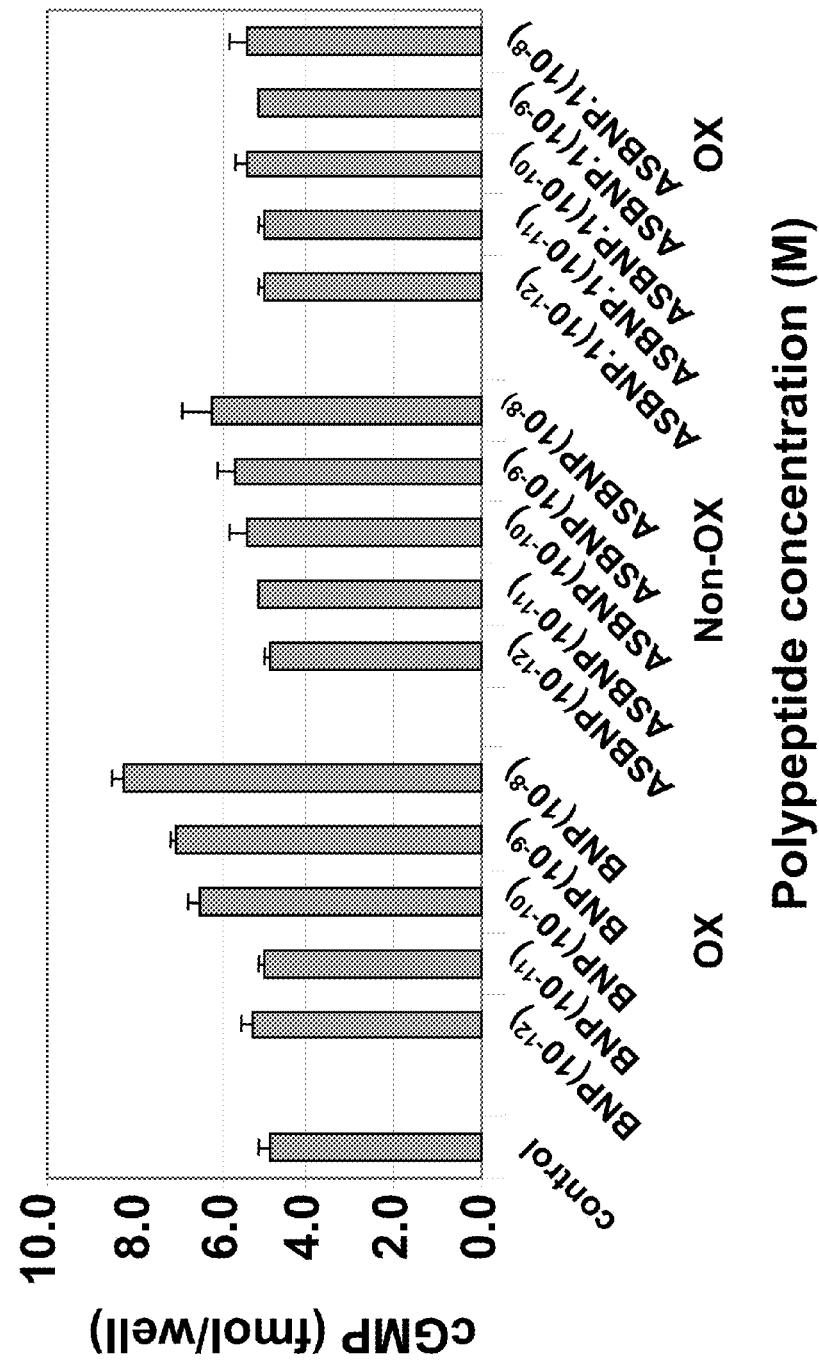
FIG. 11 is a bar graph plotting cGMP levels in HUVECS treated with BNP, ASBNP, or ASBNP.1 at the indicated concentrations. OX represents oxidized, and non-OX represents non-oxidized.
Figure 12:
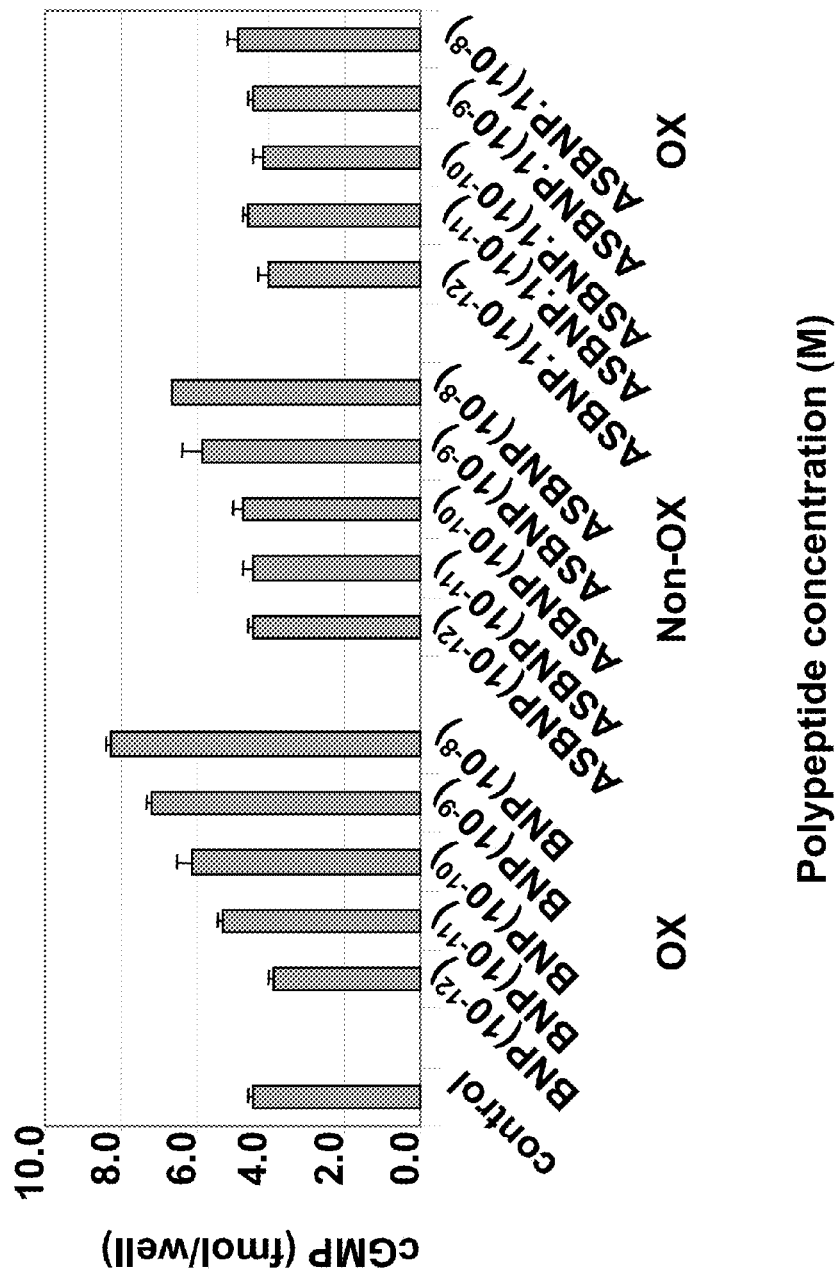
FIG. 12 is a bar graph plotting cGMP levels in HASMCS treated with BNP, ASBNP, or ASBNP.1 at the indicated concentrations. OX represents oxidized, and non-OX represents non-oxidized.

A truncated form of ASBNP that terminates prior to the cysteine and contains a 13 amino acid C-terminus tail was designed and synthesized. This polypeptide is referred to as an ASBNP.1 polypeptide (FIG. 1). The biological effects of intravenous ABNP.1 infusion were tested in normal dogs. Briefly, six normal dogs were infused with 2, 10, and 100 pmol of an ASBNP.1 polypeptide preparation, i.e., each dog received consecutive infusions of 2, 10, and 100 pmol of an ASBNP.1 polypeptide preparation. Urine flow, urinary sodium excretion, distal fractional tubular sodium reabsorption, proximal tubular fractional sodium reabsorption, mean arterial blood pressure, plasma cGMP levels, glomerular filtration rate, renal blood flow, and plasma renin levels were measured as described elsewhere (Chen et al., *Am. J. Physiol. Regul. Integr. Comp. Physiol.,* 288: R1093-R1097 (2005) and Haber et al., *J. Clin. Endocrinol. Metab.,* 29:1349-1355 (2005)). Systemic administration of the ASBNP.1 polypeptide resulted in diuretic and natriuretic effects (FIGS. 2 and 3). The effects of the ASBNP.1 polypeptide targeted distal tubules (FIGS. 4 and 5). Plasma cGMP was elevated at the super high dose. There was a trend towards a decreased renin at the two higher doses (FIGS. 6 and 7). Systemic administration of the ASBNP.1 polypeptide had no effect on glomerular filtration rate, renal blood flow, or mean arterial blood pressure (FIGS. 8-10).

These results demonstrate that the ASBNP.1 polypeptide has distinct renal effects and lacks the ability to affect systemic blood pressure.

Figure 13:
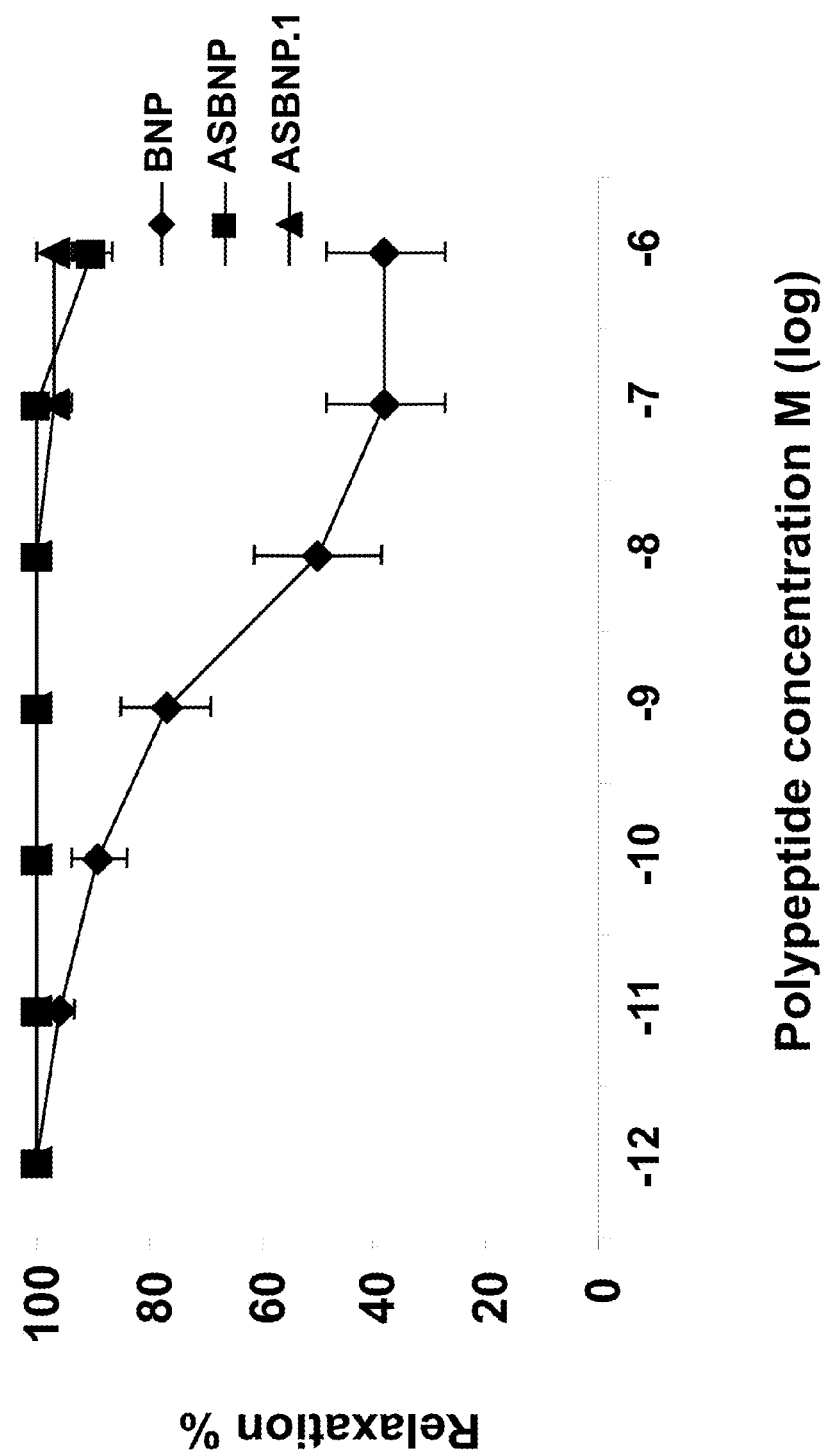
FIG. 13 is a line graph plotting vasoactivity measurements obtained from rabbit vascular rings treated with either BNP, ASBNP, or ASBNP.1 at the indicated concentrations.

The following experiments were performed to compare the activities of BNP, ASBNP, and ASBNP.1 polypeptides. Briefly, synthesized forms of BNP, ASBNP, and ASBNP.1 were administered to HUVECs and HASMCs, and cGMP levels were determined. ASBNP had minimal effects, while ASBNP.1 had no effect on cGMP in these cells. These results demonstrate that ASBNP and ASBNP.1 had no effect when administered to a rabbit artery that was pre-constricted (FIG. 13) compared with BNP.

Example 2

Biological Effects of ASBNP.1 Polypeptides in Mammals with CHF

The biological effects of intravenous ABNP.1 infusion were tested in a paced dog model of congestive heart failure (CHF). Briefly, 10 dogs underwent surgical implantation of a programmable cardiac pacemaker (Medtronic, Minneapolis, Minn.). After postoperative recovery, the animals received 11 days of rapid ventricular pacing (240 beats/minute), which can induce overt congestive heart failure CHF as described elsewhere (Chen et al., *Circulation,* 100:2443-2448 (1999)). The dogs were intravenously infused with 2, 10, and 100 pmol of an ASBNP.1 polypeptide preparation, i.e., each dog received consecutive infusions of 2, 10, and 100 pmol of an ASBNP.1 polypeptide preparation.

Figure 15:
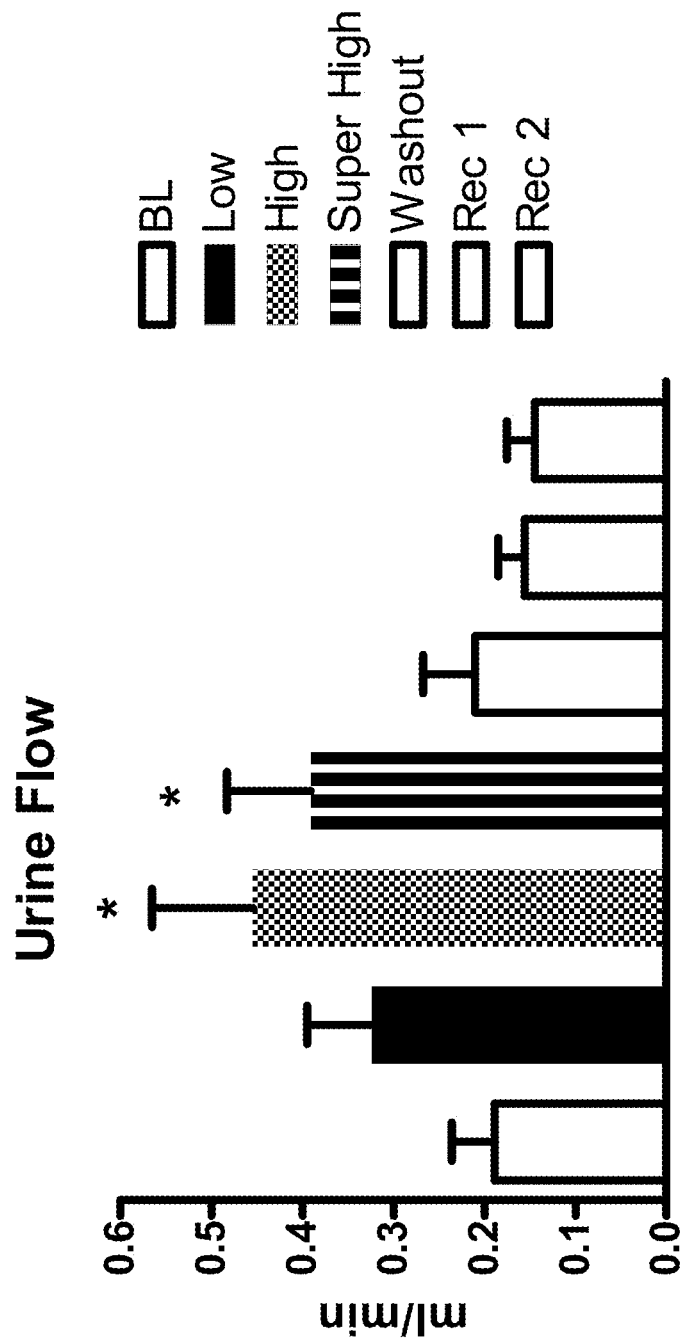
FIG. 15 is a bar graph plotting urine flow rates for paced dogs treated with ASBNP.1 as indicated. Baseline is prior to administration; low is 2 pmol; high is 10 pmol; super high is 100 pmol; rec 1 is recovery 1; and rec 2 is recovery 2.
Figure 16:
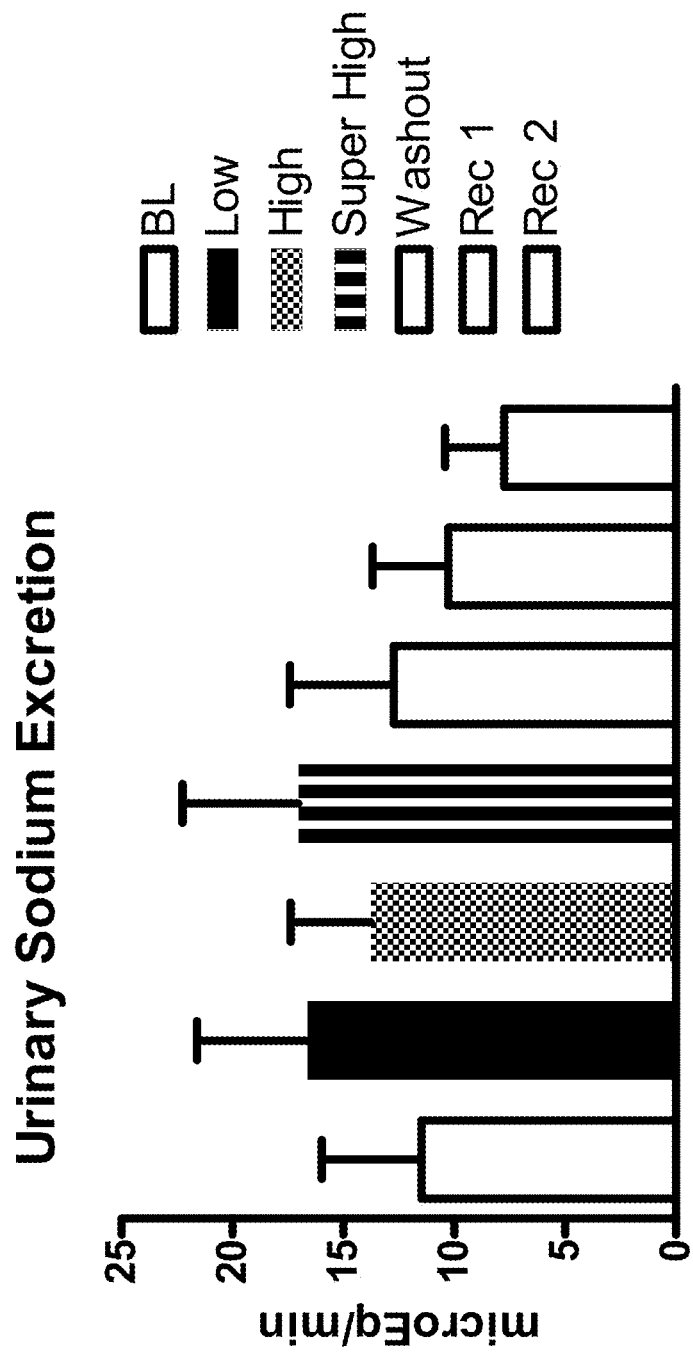
FIG. 16 is a bar graph plotting urinary sodium excretion rates for paced dogs treated with ASBNP.1 as indicated. Baseline is prior to administration; low is 2 pmol; high is 10 pmol; super high is 100 pmol; rec 1 is recovery 1; and rec 2 is recovery 2.
Figure 17:
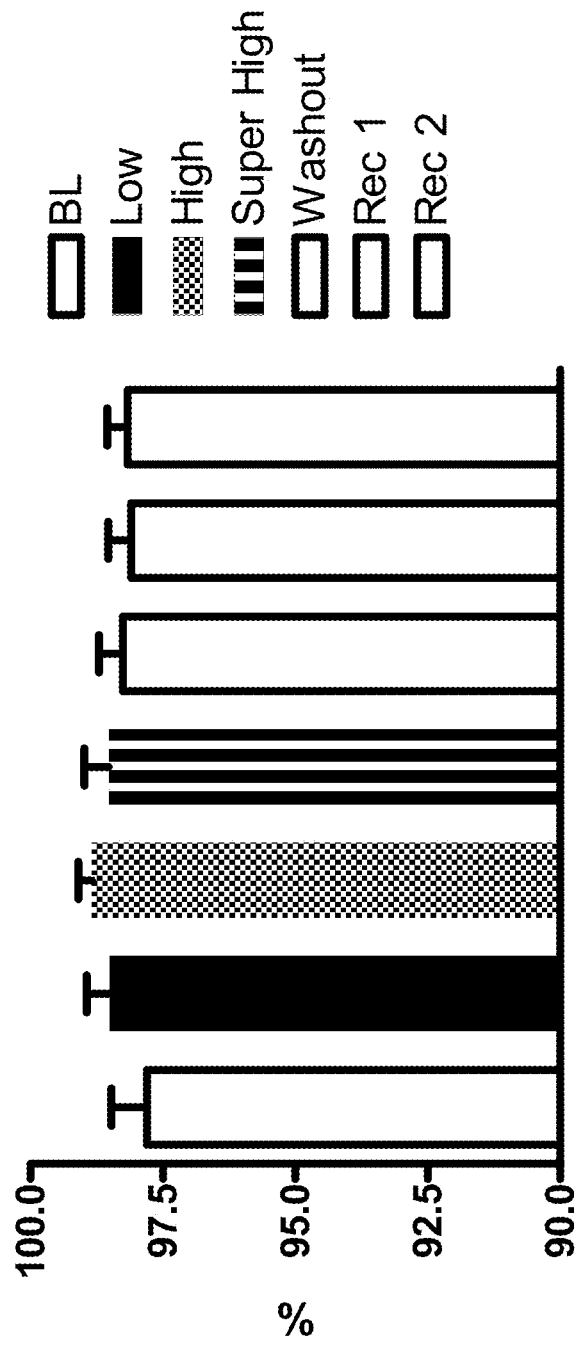
FIG. 17 is a bar graph plotting distal fractional tubular sodium reabsorption rates for paced dogs treated with ASBNP.1 as indicated. Baseline is prior to administration; low is 2 pmol; high is 10 pmol; super high is 100 pmol; rec 1 is recovery 1; and rec 2 is recovery 2.
Figure 18:
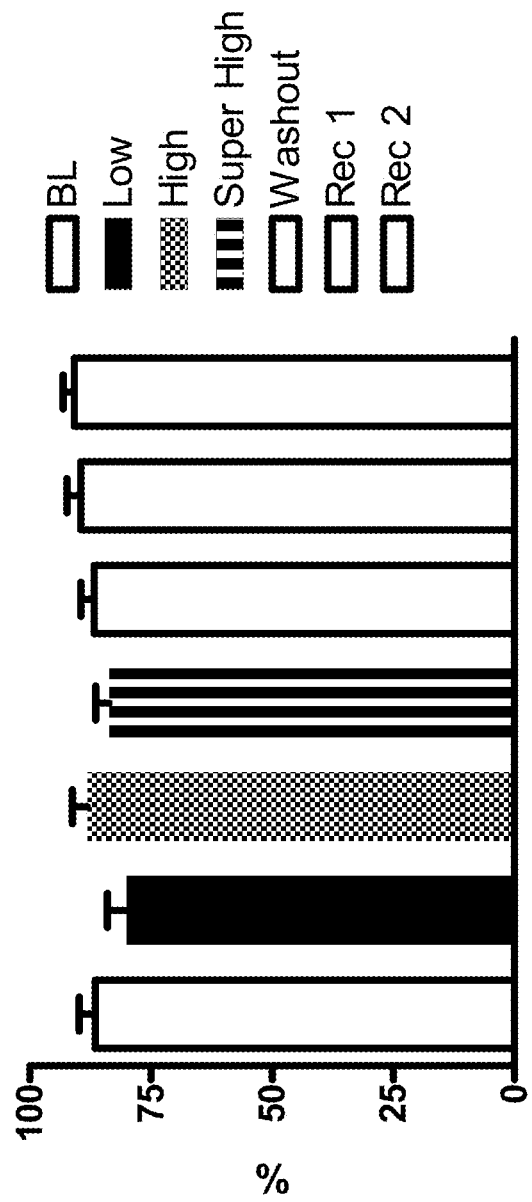
FIG. 18 is a bar graph plotting proximal tubular fractional sodium reabsorption rates for paced dogs treated with ASBNP.1 as indicated. Baseline is prior to administration; low is 2 pmol; high is 10 pmol; super high is 100 pmol; rec 1 is recovery 1; and rec 2 is recovery 2.
Figure 19:
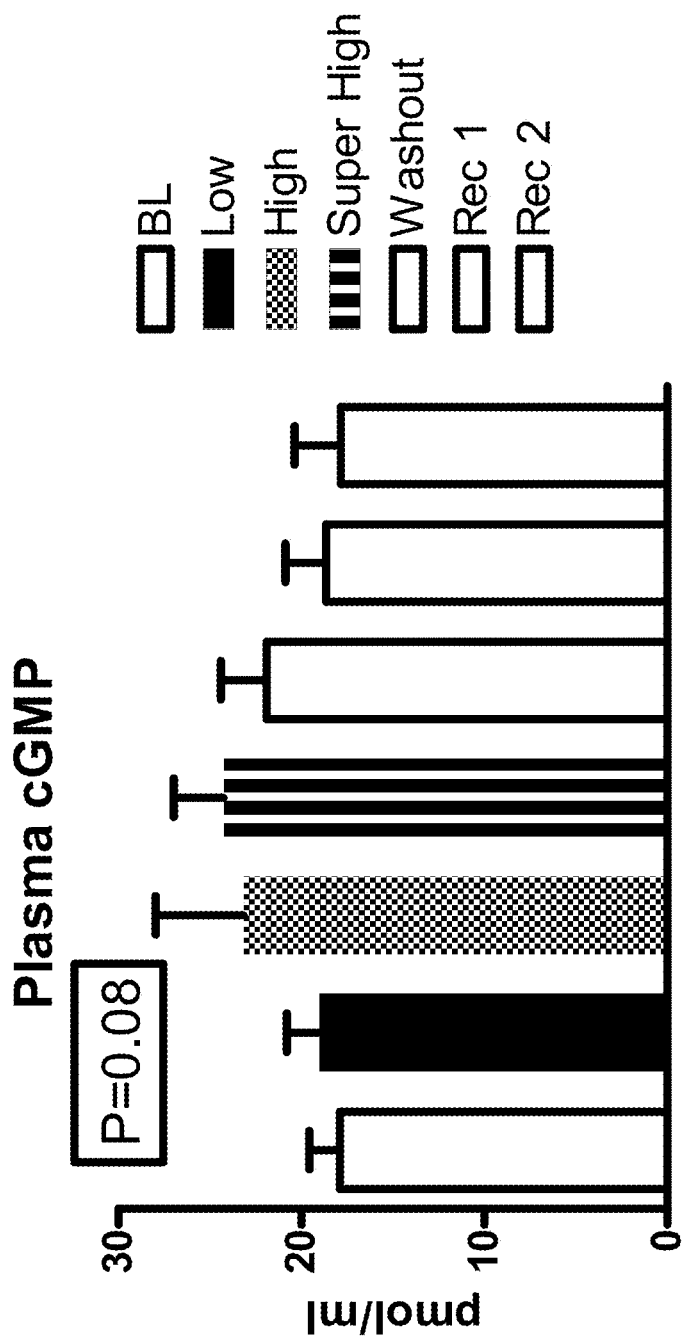
FIG. 19 is a bar graph plotting plasma cGMP levels for paced dogs treated with ASBNP.1 as indicated. Baseline is prior to administration; low is 2 pmol; high is 10 pmol; super high is 100 pmol; rec 1 is recovery 1; and rec 2 is recovery 2.
Figure 20:
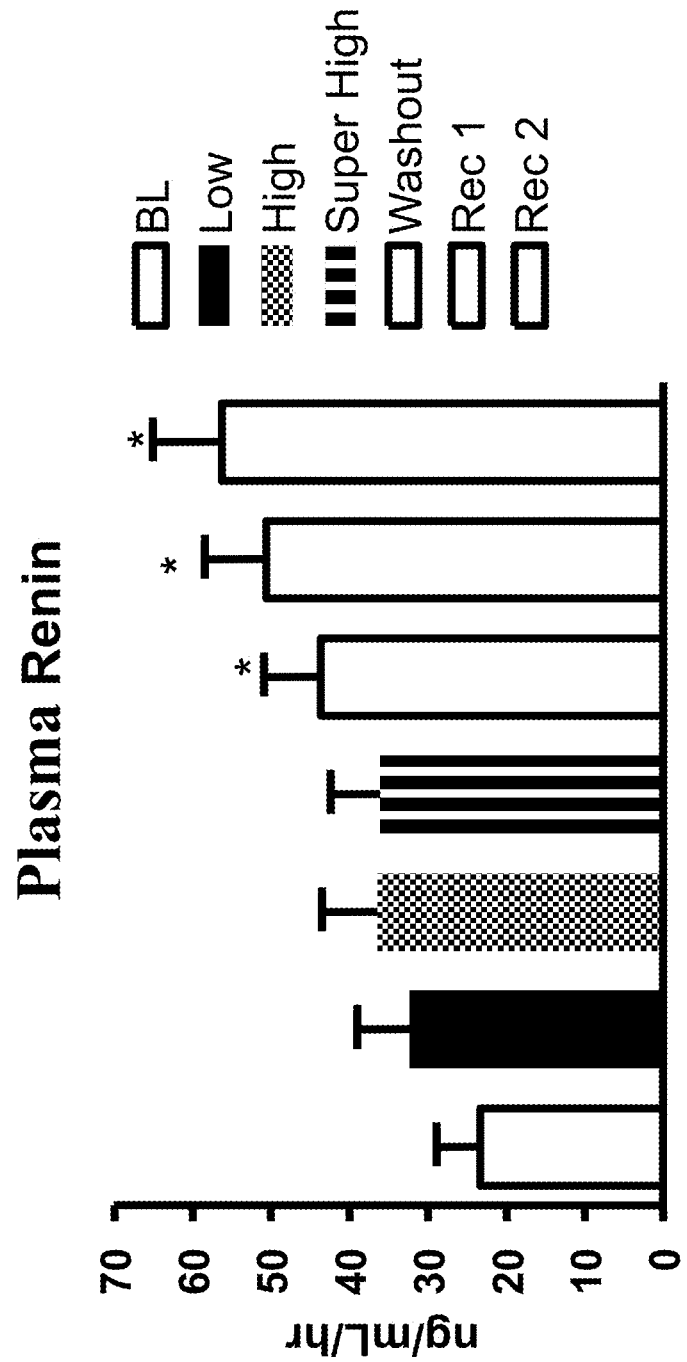
FIG. 20 is a bar graph plotting plasma renin activity (ng/mL/hour) for paced dogs treated with ASBNP.1 as indicated. Baseline is prior to administration; low is 2 pmol; high is 10 pmol; super high is 100 pmol; rec 1 is recovery 1; and rec 2 is recovery 2.
Figure 21:
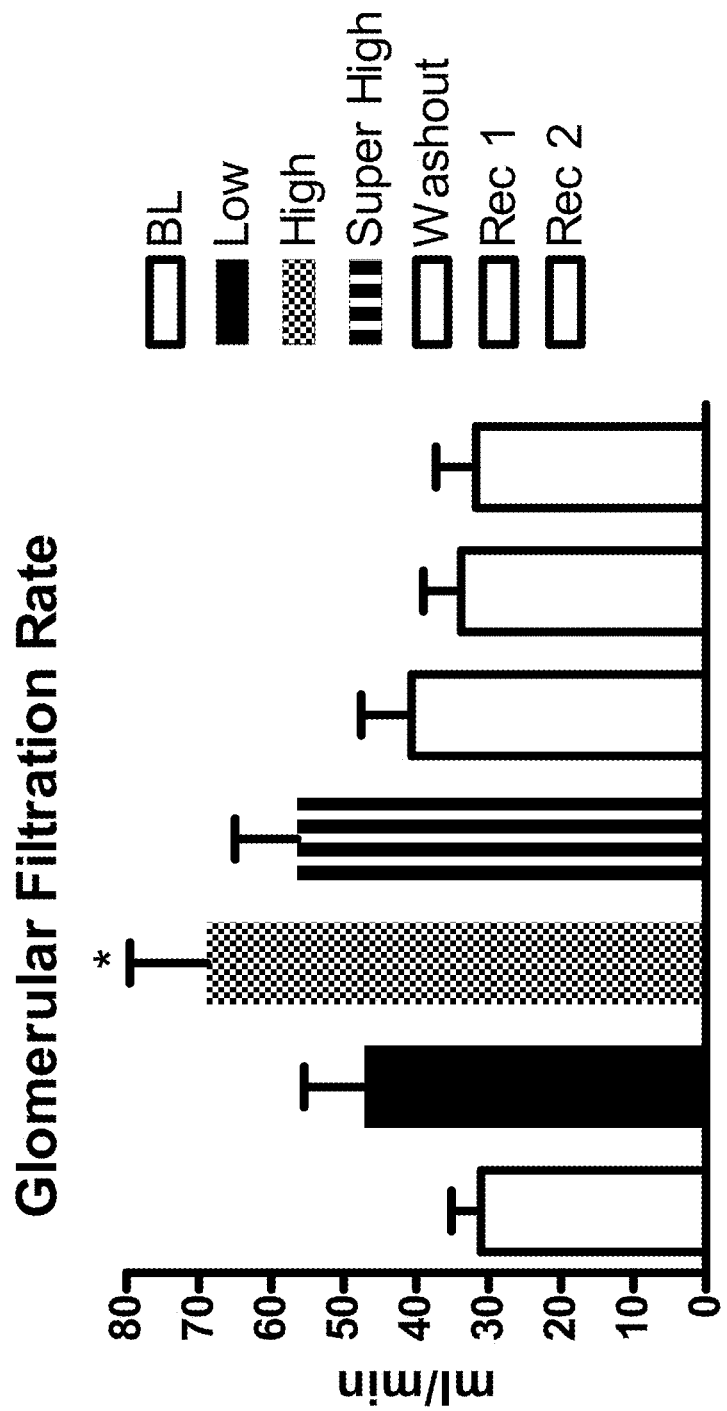
FIG. 21 is a bar graph plotting glomerular filtration rates for paced dogs treated with ASBNP.1 as indicated. Baseline is prior to administration; low is 2 pmol; high is 10 pmol; super high is 100 pmol; rec 1 is recovery 1; and rec 2 is recovery 2.
Figure 22:
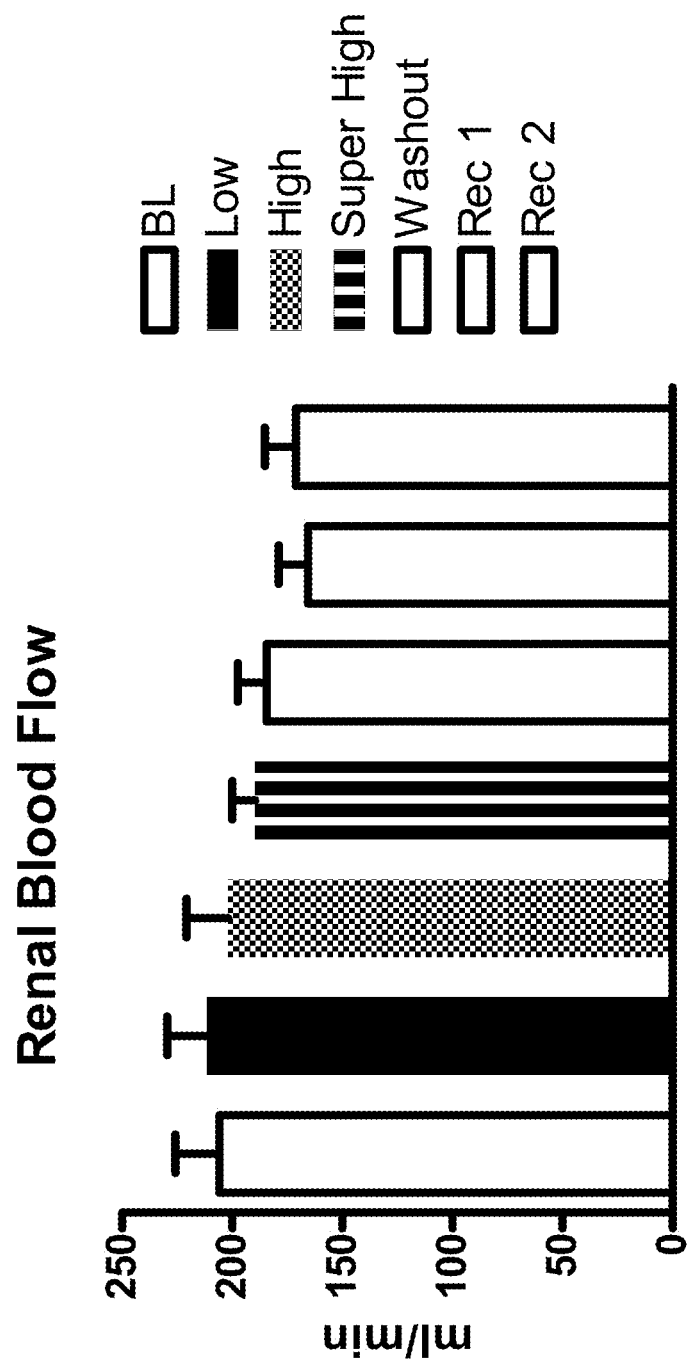
FIG. 22 is a bar graph plotting renal blood flow rates for paced dogs treated with ASBNP.1 as indicated. Baseline is prior to administration; low is 2 pmol; high is 10 pmol; super high is 100 pmol; rec 1 is recovery 1; and rec 2 is recovery 2.
Figure 23:
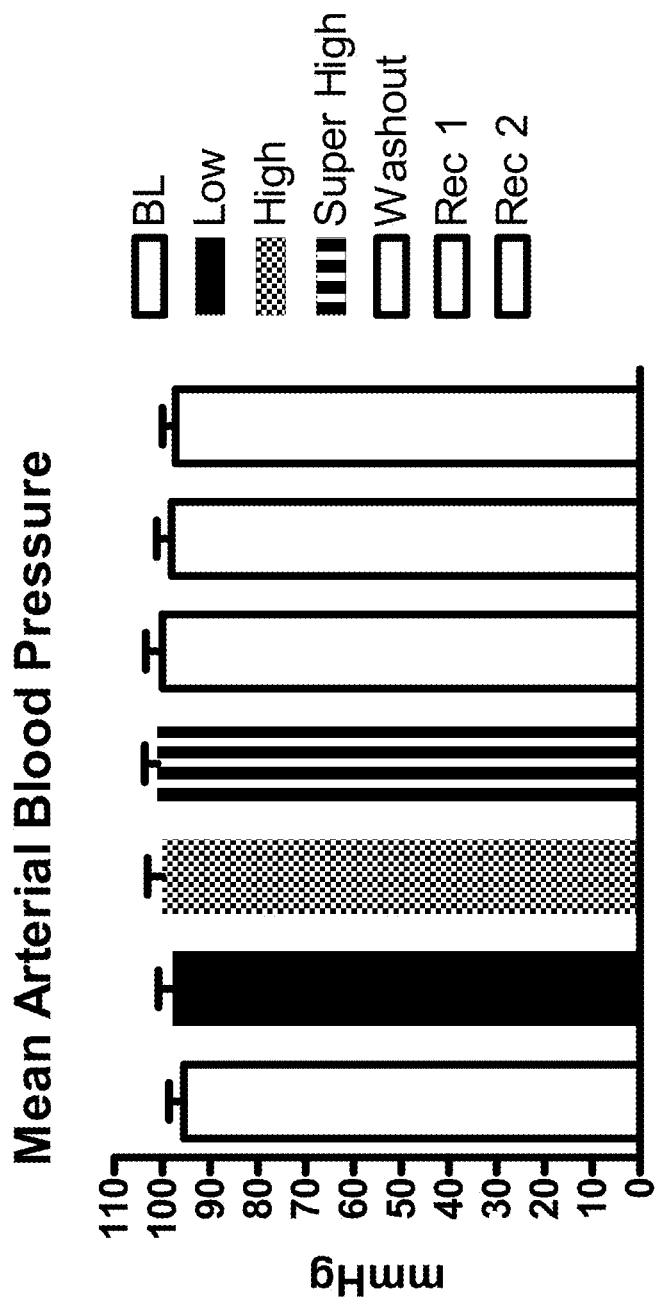
FIG. 23 is a bar graph plotting mean arterial blood pressure levels for paced dogs treated with ASBNP.1 as indicated. Baseline is prior to administration; low is 2 pmol; high is 10 pmol; super high is 100 pmol; rec 1 is recovery 1; and rec 2 is recovery 2.
Figure 24:
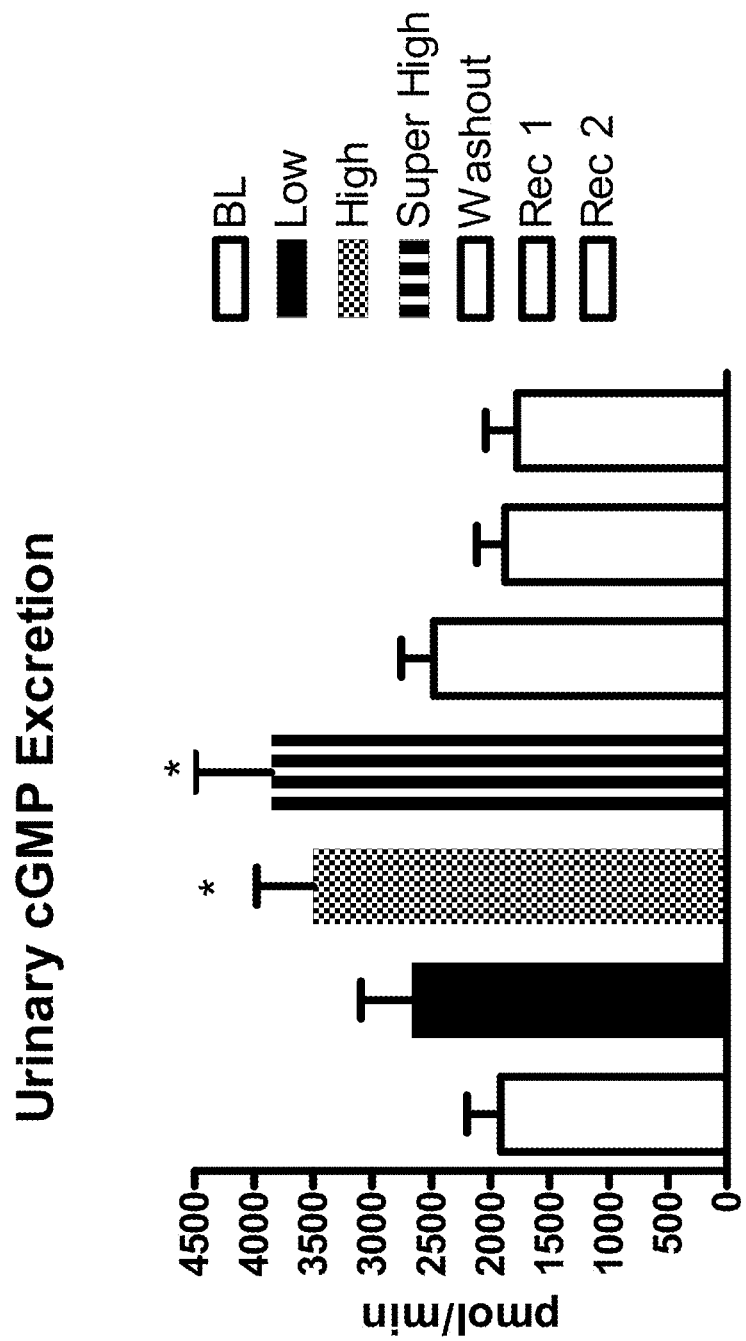
FIG. 24 is a bar graph plotting urinary cGMP excretion for paced dogs treated with ASBNP.1 as indicated. Baseline is prior to administration; low is 2 pmol; high is 10 pmol; super high is 100 pmol; rec 1 is recovery 1; and rec 2 is recovery 2.
Figure 25:
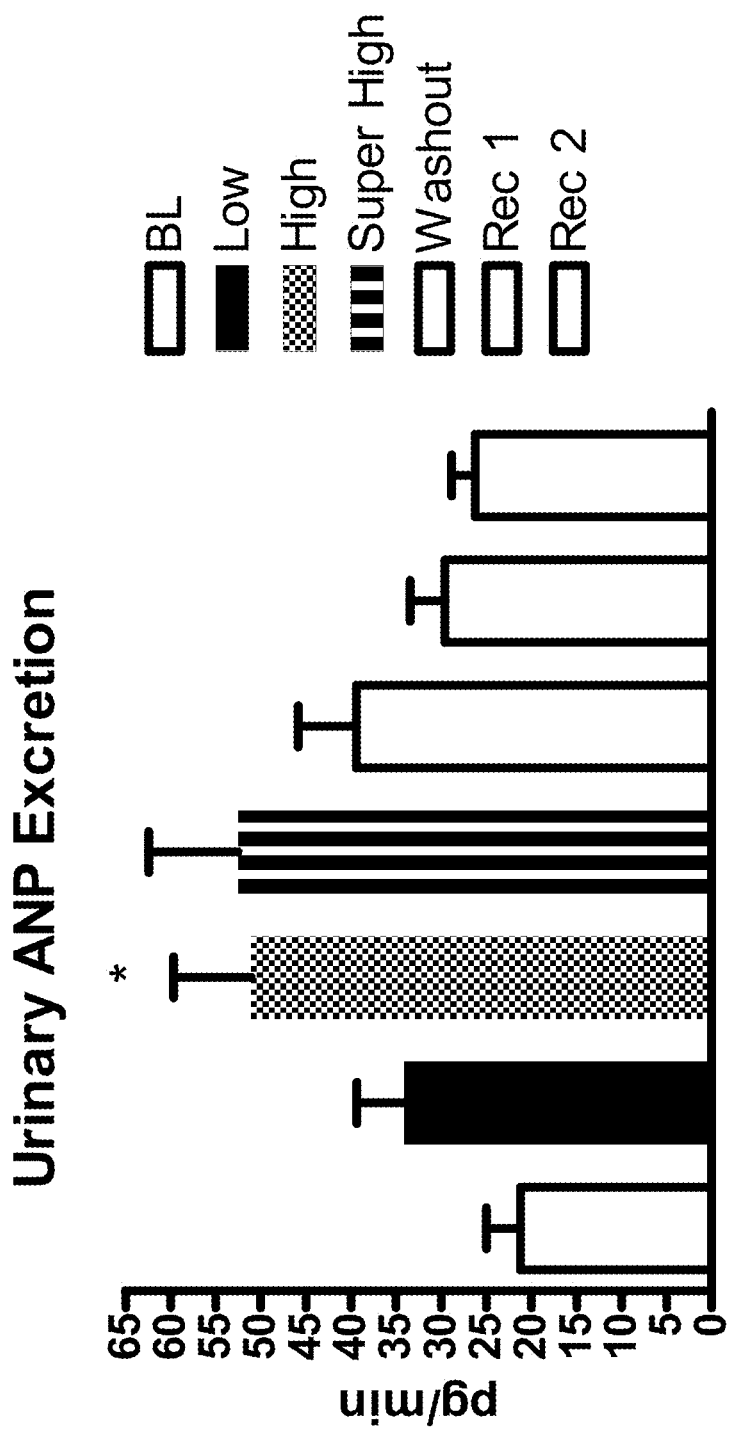
FIG. 25 is a bar graph plotting urinary ANP excretion for paced dogs treated with ASBNP.1 as indicated. Baseline is prior to administration; low is 2 pmol; high is 10 pmol; super high is 100 pmol; rec 1 is recovery 1; and rec 2 is recovery 2.
Figure 26:
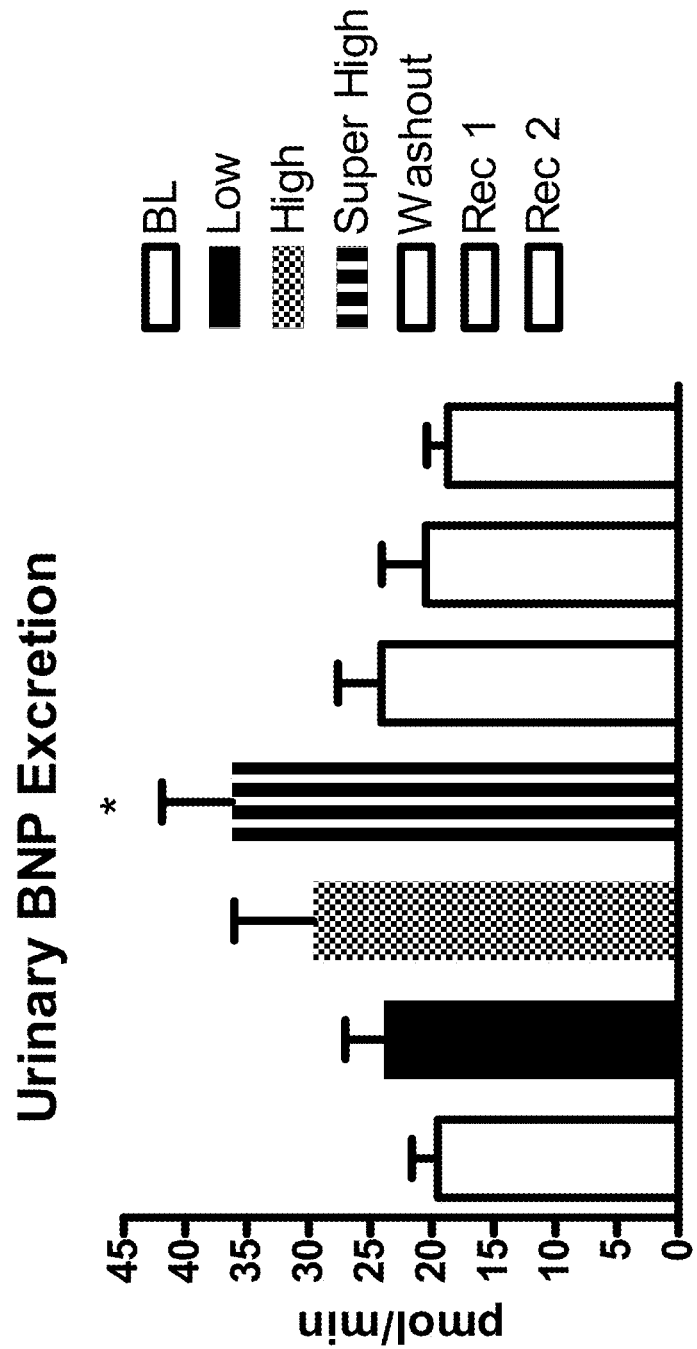
FIG. 26 is a bar graph plotting urinary BNP excretion for paced dogs treated with ASBNP.1 as indicated. Baseline is prior to administration; low is 2 pmol; high is 10 pmol; super high is 100 pmol; rec 1 is recovery 1; and rec 2 is recovery 2.
Figure 27:
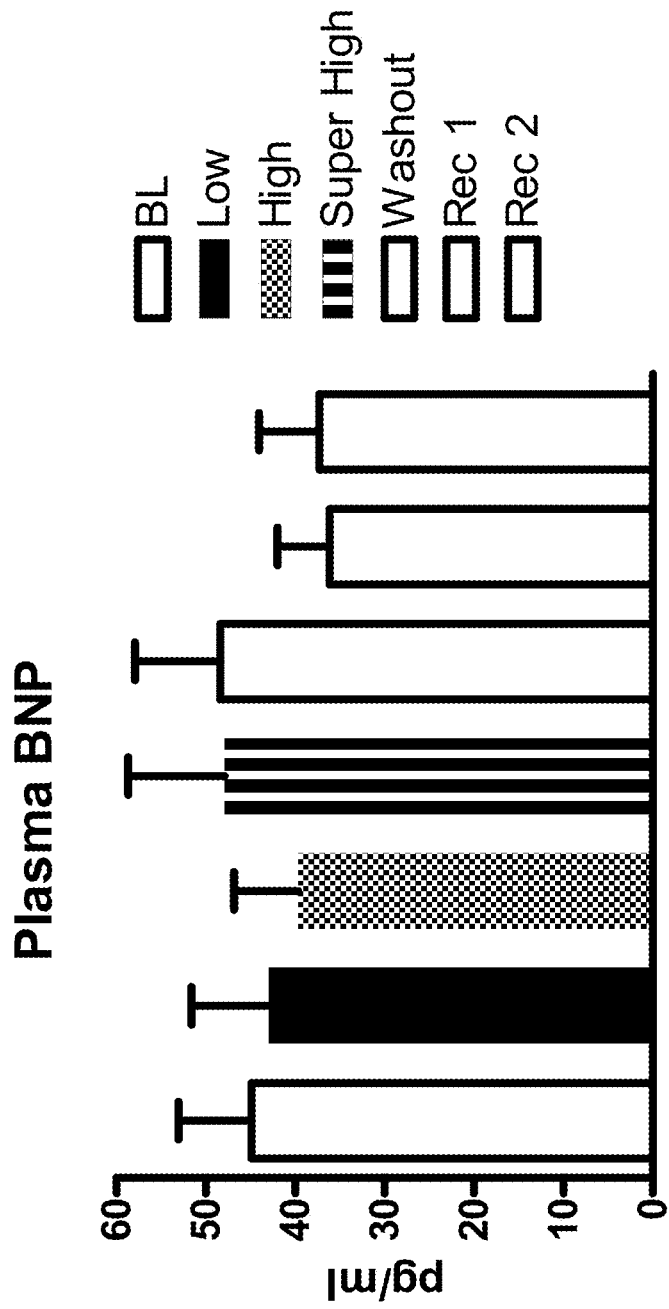
FIG. 27 is a bar graph plotting plasma BNP levels for paced dogs treated with ASBNP.1 as indicated. Baseline is prior to administration; low is 2 pmol; high is 10 pmol; super high is 100 pmol; rec 1 is recovery 1; and rec 2 is recovery 2.
Figure 28:
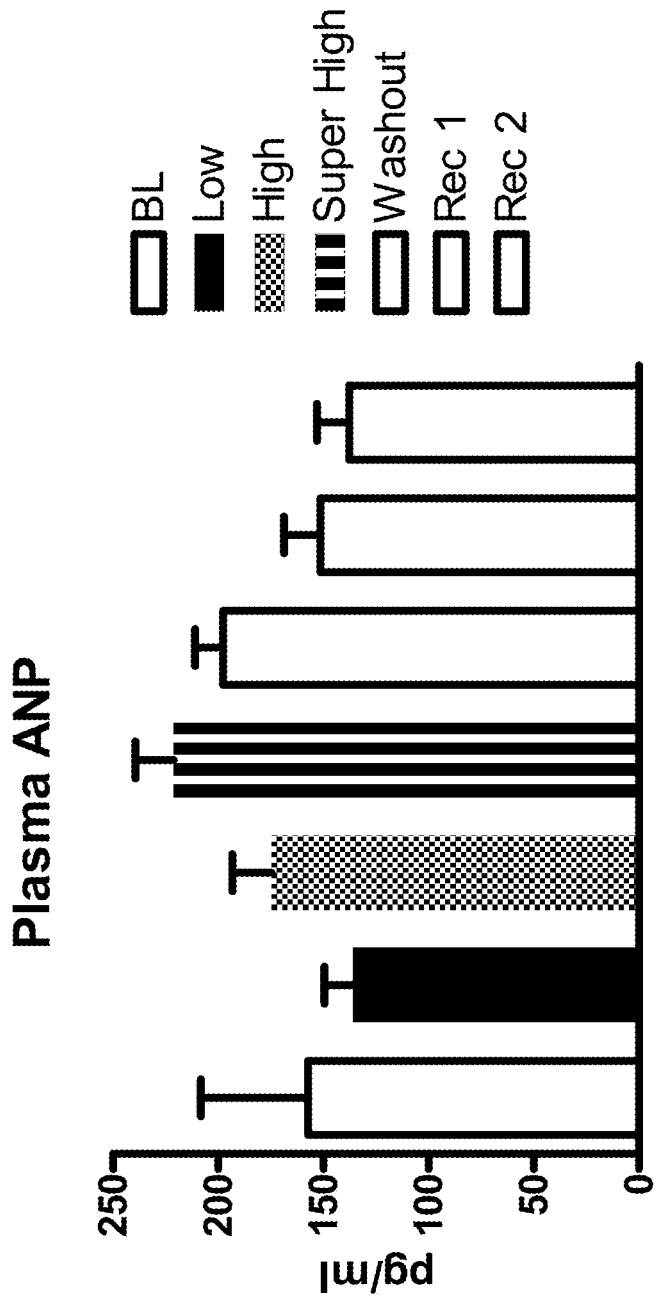
FIG. 28 is a bar graph plotting plasma ANP levels for paced dogs treated with ASBNP.1 as indicated. Baseline is prior to administration; low is 2 pmol; high is 10 pmol; super high is 100 pmol; rec 1 is recovery 1; and rec 2 is recovery 2.
Figure 29:
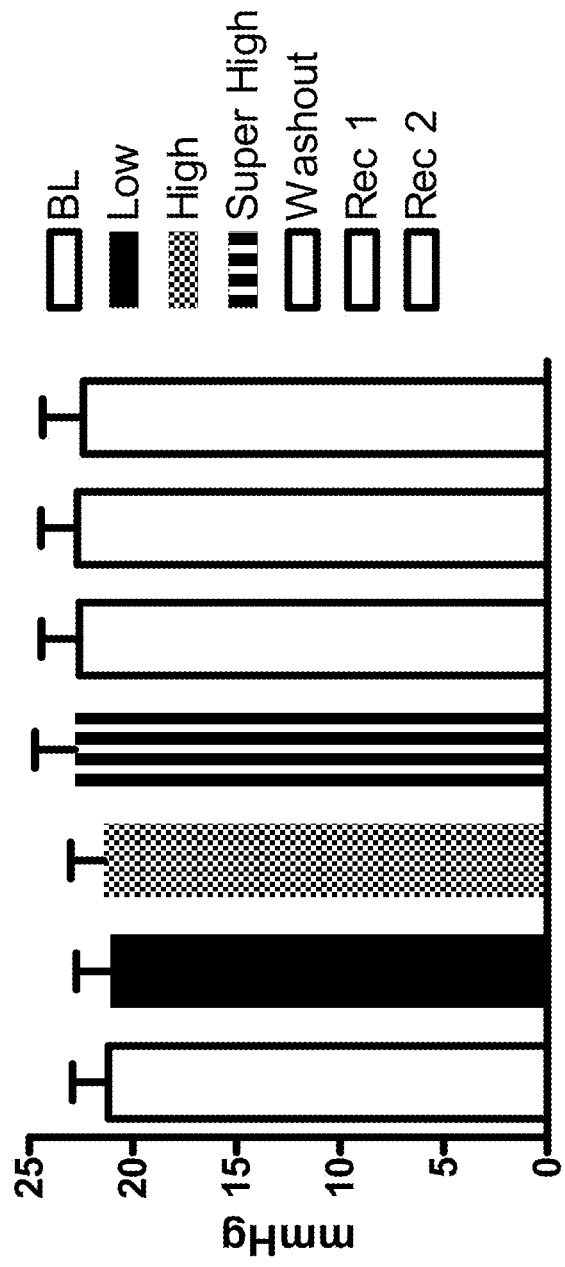
FIG. 29 is a bar graph plotting pulmonary capillary wedge pressure for paced dogs treated with ASBNP.1 as indicated. Baseline is prior to administration; low is 2 pmol; high is 10 pmol; super high is 100 pmol; rec 1 is recovery 1; and rec 2 is recovery 2.
Figure 30:
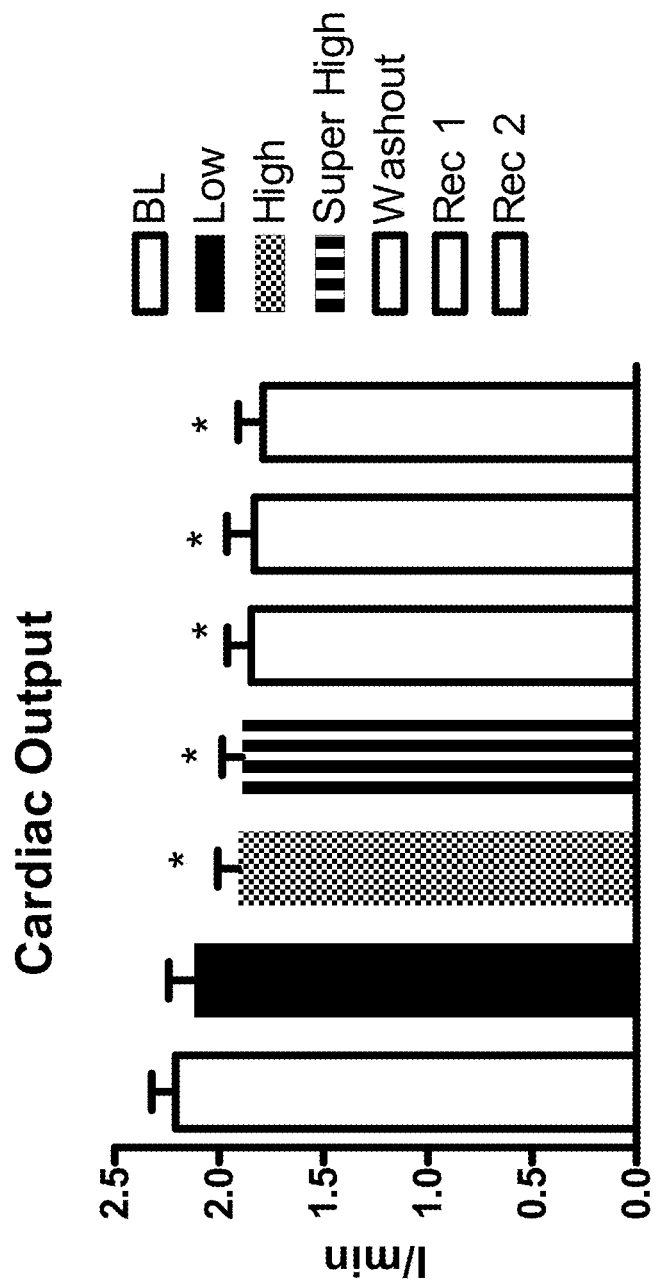
FIG. 30 is a bar graph plotting cardiac output for paced dogs treated with ASBNP.1 as indicated. Baseline is prior to administration; low is 2 pmol; high is 10 pmol; super high is 100 pmol; rec 1 is recovery 1; and rec 2 is recovery 2.
Figure 31:
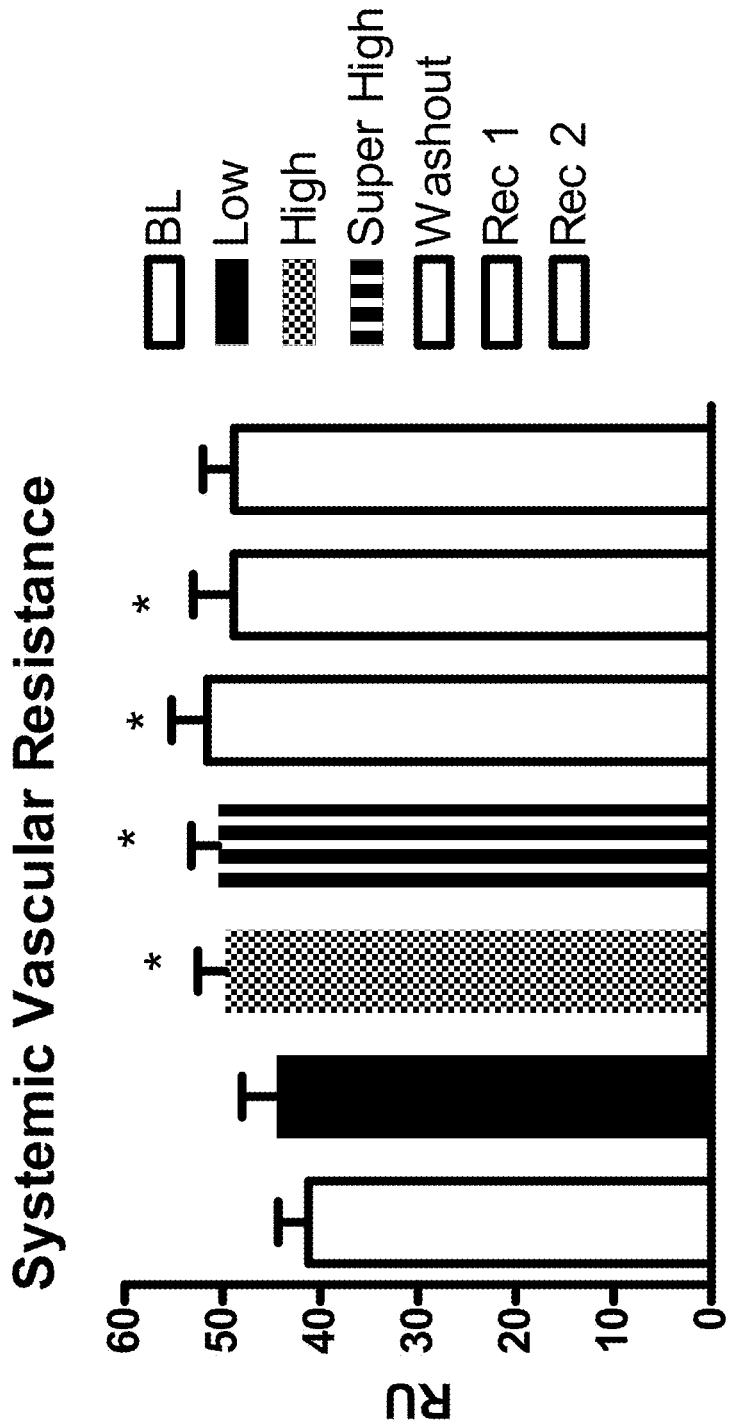
FIG. 31 is a bar graph plotting systemic vascular resistance for paced dogs treated with ASBNP.1 as indicated. Baseline is prior to administration; low is 2 pmol.

Acute hemodynamic studies were performed at the time of infusion, and comparisons were made between groups and among dogs at baseline and during each infusion. Urine flow, urinary sodium excretion, distal fractional tubular sodium reabsorption, proximal tubular fractional sodium reabsorption, plasma cGMP levels, rennin levels, glomerular filtration rate, renal blood flow, mean arterial blood pressure, urinary cGMP excretion, urinary ANP excretion, urinary BNP excretion, plasma BNP levels, plasma ANP levels, pulmonary capillary wedge pressure, cardiac output, systemic vascular resistance, angiotensin II levels, and aldosterone levels were measured as described elsewhere (Chen et al., *Am. J. Physiol. Regul. Integr. Comp. Physiol.,* 288: R1093-R1097 (2005) and Haber et al., *J. Clin. Endocrinol. Metab.,* 29:1349-1355 (2005)). Systemic administration of the ASBNP.1 polypeptide to the paced dogs resulted in diuretic but not natriuretic effects (FIGS. 15 and 16). Renin rate increased throughout the washout period (FIG. 20). Systemic administration of the ASBNP.1 polypeptide increased glomerular filtration rate at the high level (FIG. 21). Systemic administration of the ASBNP.1 polypeptide increased urinary cGMP excretion at the high and super high levels (FIG. 24). The high level also increased urinary ANP excretion (FIG. 25). The super high level also increased urinary BNP excretion (FIG. 26). Cardiac output was decreased from the administration of the high level of polypeptide and remained decrease throughout the remainder of the experiment (FIG. 30). Systemic vascular resistance was increased during the high, super high, washout, and recovery 1 phases (FIG. 31). Aldosterone was increased from the administration of the low level of polypeptide and continued to increase throughout the remainder of the experiment (FIG. 33). There was no effect on distal tubular fractional sodium reabsorption, proximal tubular fractional sodium reabsorption renal blood flow, plasma cGMP, mean arterial blood pressure, plasma BNP, plasma ANP, pulmonary capillary wedge pressure, or angiotensin II levels (FIGS. 17, 18, 19, 22, 23, 28, 29, and 32).

These results demonstrate that the ASBNP.1 polypeptide has renal effects (including enhanced GFR) and lacks the ability to affect systemic blood pressure in CHF animals.

In another experiment, an ASBNP.1 polypeptide preparation was administered to dogs (100 pmol/kg/minute for 90 minutes). Urinary sodium excretion, urine flow, mean arterial blood pressure, renal blood flow, pulmonary capillary wedge pressure, and cardiac output were measured after 30, 60, and 90 minutes of administering the ASBNP.1 polypeptide. Administration of ASBNP.1 polypeptide was followed by a washout period of 30 minutes. The washout was performed by administering normal saline. Urinary sodium excretion, urine flow, mean arterial blood pressure, renal blood flow, pulmonary capillary wedge pressure, and cardiac output were measured again after the washout period, and after each of two recovery periods at 60 minutes (Rec 1) and 90 minutes (Rec 2) after administration of the ASBNP.1 polypeptide. The results are presented in FIGS. 34-39. Administration of ASBNP.1 polypeptide at a dose of 100 pmol/kg/minute for 90 minutes was observed to increase urinary sodium excretion as well as urine flow (FIGS. 34 and 35). No significant effect was observed on mean arterial blood pressure, renal blood flow, or cardiac output (FIGS. 36, 37, and 39). A decrease in pulmonary capillary wedge pressure was observed 60 minutes after administration of ASBNP.1 polypeptide (FIG. 38), without a change in PAP (pulmonary arterial pressure) or RAP (right arterial pressure).

Example 3

Biological Effects of ASBNP.1 Polypeptides Using Animal Models

The effects of ASBNP.1 infusion is further assessed in the TIVCC model (a dog model of sodium retention which mimics cirrhosis and nephrosis). The TIVCC model of sodium-retention and ascites without concurrent increases in cardiac filling pressure as described elsewhere (Wei et al., *Am. J. Physiol.,* 273:R838-844 (1997)). The ASBNP.1 polypeptide is tested in the TIVCC model using increasing doses up to 100 pmol.kg/minute administered intravenously.

Example 4

Induction Radiocontrast-induced Nephropathy in Dogs with Heart Failure Produced by Rapid Ventricular Pacing Under pentobarbital anesthesia (30 mg/kg) and via a left thoracotomy and pericardiectomy, the heart is exposed and a screw-in epicardial pacemaker lead is implanted into the right ventricle. The pacemaker lead is connected to a pacemaker implanted subcutaneously in the chest. In addition, at the time of pacemaker implantation, a polyethylene catheter (PE 240, Clay Adams, Parsippany, N.J., USA) is placed via a femoral artery into the aorta at least 6 cm above the renal arteries. Dogs are allowed to recover over a three day period, during which time they receive prophylactic antibiotic treatment with clindamycin and Combater. Following recovery from surgery, the pacemaker is programmed to 250 beats per minute and pacing continues at this rate for 10 days to produce heart failure.

On the day of an acute experiment 11 days after starting pacing, radiocontrast agent (Vascoray®, Mallinkrodt, Inc., St. Louis, Mo., USA) is infused intravenously at a dose of 7 mL/kg over a 10-minute period. Dogs are returned to metabolic cages for a series of six consecutive 24-hour urine collections for monitoring of radiocontrast induced nephropathy as described elsewhere (Margulies et al., *Kidney International*, 38(6):1101-8 (1990)).

In some experiments, ASBNP.1 polypeptide is administered to paced dogs prior to administering radiocontrast agent. Each dog is administered consecutive infusions of 2, 10, and 100 pmol of ASBNP.1 polypeptide or one 90 minute infusion with 100 pmol of ASBNP.1 polypeptide. Urinary sodium excretion, urine flow, mean arterial blood pressure, renal blood flow, pulmonary capillary wedge pressure, and cardiac output were measured 30, 60, and 90 minutes after administering the ASBNP.1 polypeptide, after a washout period, and during each of two recovery periods following the washout period. Measurements of the clinical parameters are compared to measurements taken in control dogs that were not administered ASBNP.1 prior to administration of radiocontrast agent.

Example 5

Prevention of Contrast Induced Renal Failure in High Risk Patients Including Patients with CHF Patients at high risk of CIN (e.g., elderly patients and patients at risk for chronic renal insufficiency, diabetes, and heart failure) who require contrast for imaging (e.g., angiography or CT) are treated prophylactically with IV infusions of ASBNP polypeptide or ASBNP.1 polypeptide prior to administration of contrast media. Prior to the infusion, vital signs are taken and laboratory tests are performed to measure electrolytes, serum creatinine, cystatin, and BNP polypeptide levels. BNP polypeptide levels are obtained using the Biosite BNP assay, which detects ASBNP polypeptide, and/or using an assay specific for ASBNP polypeptide. Baseline urine output is measured and urine electrolytes are assessed. An intravenous infusion of ASBNP polypeptide, ASBNP.1 polypeptide, or a derivative is initiated prior to contrast administration. Vital signs and urine output are assessed every 2 hours during the infusion. At a predetermined time following initiation, the patient undergoes contrast administration. This time may coincide with achievement of a polypeptide level of a certain concentration as determined by a specific assay for the polypeptides. Following contrast administration, the infusion continues for 8 to 24 hours or until serum creatinine and/or cystatin is noted to be unchanged from baseline.

Example 6

Treatment of Cardiorenal Syndrome

Patients who develop worsening renal function with diuretic resistance in the setting of acute decompensated heart failure are treated prospectively with IV infusions of ASBNP polypeptide or ASBNP.1 polypeptide. Prior to the infusion, vital signs are taken and laboratory tests are performed to measure electrolytes, serum creatinine, cystatin, and BNP polypeptide levels. Baseline urine output is measured and urine electrolytes are assessed. An intravenous infusion of ASBNP polypeptide, ASBNP.1 polypeptide, or a derivative thereof is initiated. Vital signs and urine output are assessed every 2 hours during the infusion, which is 12 to 72 hours in duration. Drug levels, BNP polypeptide levels, serum creatinine, cystatin, and plasma and urine electrolytes are assessed daily throughout the infusion.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a mammal having a renal dysfunction, wherein said method comprises administering to said mammal a polypeptide between 37 and 47 amino acid residues in length, wherein said polypeptide comprises an amino acid sequence that aligns to the sequence set forth in SEQ ID NO:1 with five, four, three, two, or one amino acid addition(s), deletion(s), substitution(s), or combinations thereof, and wherein said polypeptide is administered in an amount effective to reduce the severity of a symptom of said renal dysfunction.

2. The method of claim 1, wherein said mammal is a human.

3. The method of claim 1, wherein said renal dysfunction comprises renal failure.

4. The method of claim 1, wherein said renal dysfunction comprises renal failure accompanied with congestive heart failure.

5. The method of claim 1, wherein said polypeptide is between 40 and 44 amino acid residues in length and comprises an amino acid sequence that aligns to the sequence set forth in SEQ ID NO:1 with one or two amino acid additions, deletions, substitutions, or combinations thereof.

6. The method of claim 1, wherein said symptom comprises an abnormal serum creatinine level, urine flow, renin level, glomerular filtration rate, urinary cGMP excretion rate, urinary ANP excretion rate, urinary BNP excretion rate, cardiac output, systemic vascular resistance, or aldosterone level.

* * * * *